(12) United States Patent
Dill

(10) Patent No.: US 10,596,127 B2
(45) Date of Patent: Mar. 24, 2020

(54) COMPOSITION FOR REDUCING THE FREQUENCY OF URINATION, METHOD OF MAKING AND USE THEREOF

(71) Applicant: WELLESLEY PHARMACEUTICALS, LLC, Newtown, PA (US)

(72) Inventor: David A. Dill, Newtown, PA (US)

(73) Assignee: WELLESLEY PHARMACEUTICALS, LLC, Newtown, PA (US)

( * ) Notice: Subject to any disclaimer, the term of this patent is extended or adjusted under 35 U.S.C. 154(b) by 39 days.

(21) Appl. No.: 14/870,676

(22) Filed: Sep. 30, 2015

(65) Prior Publication Data

US 2016/0015660 A1    Jan. 21, 2016

Related U.S. Application Data

(63) Continuation-in-part of application No. 14/815,416, filed on Jul. 31, 2015, which is a continuation of application No. 13/828,778, filed on Mar. 14, 2013, now Pat. No. 9,119,878.

(51) Int. Cl.
| | |
|---|---|
| *A61K 31/167* | (2006.01) |
| *A61K 31/192* | (2006.01) |
| *A61K 45/06* | (2006.01) |
| *A61K 31/616* | (2006.01) |
| *A61K 31/18* | (2006.01) |
| *A61K 31/56* | (2006.01) |
| *A61K 9/28* | (2006.01) |
| *A61K 31/58* | (2006.01) |
| *A61K 31/405* | (2006.01) |
| *A61K 31/12* | (2006.01) |

(52) U.S. Cl.
CPC .......... *A61K 31/167* (2013.01); *A61K 9/284* (2013.01); *A61K 9/2846* (2013.01); *A61K 9/2866* (2013.01); *A61K 31/12* (2013.01); *A61K 31/18* (2013.01); *A61K 31/192* (2013.01); *A61K 31/405* (2013.01); *A61K 31/56* (2013.01); *A61K 31/58* (2013.01); *A61K 31/616* (2013.01); *A61K 45/06* (2013.01)

(58) Field of Classification Search
CPC ...... A61K 31/167; A61K 31/12; A61K 31/58; A61K 9/2866; A61K 31/405; A61K 9/284; A61K 9/2846; A61K 31/18; A61K 31/56; A61K 31/192; A61K 31/616; A61K 45/06

See application file for complete search history.

(56) References Cited

U.S. PATENT DOCUMENTS

| | | | |
|---|---|---|---|
| 5,474,786 A | 12/1995 | Kotwal et al. | |
| 6,544,554 B1 | 4/2003 | Maeda et al. | |
| 7,678,821 B2 | 3/2010 | Paborji | |
| 2003/0191172 A1 | 10/2003 | Versi | |
| 2003/0194428 A1 | 10/2003 | Miller et al. | |
| 2004/0054008 A1 | 3/2004 | Araki | |
| 2004/0067908 A1* | 4/2004 | Nakade .................. A61K 31/00 514/54 |
| 2004/0198822 A1 | 10/2004 | Fraser et al. | |
| 2005/0008702 A1 | 1/2005 | Faour et al. | |
| 2006/0035923 A1 | 2/2006 | Van Meeteren et al. | |
| 2006/0100195 A1 | 5/2006 | Maruyama et al. | |
| 2007/0197666 A1 | 8/2007 | Baiker et al. | |
| 2008/0009538 A1 | 1/2008 | Skolnick | |
| 2008/0085314 A1 | 4/2008 | Shalaby | |
| 2008/0095843 A1 | 4/2008 | Nutalapati et al. | |
| 2008/0166407 A1 | 7/2008 | Shalaby et al. | |
| 2009/0202634 A1* | 8/2009 | Jans ..................... A61K 9/2018 424/468 |
| 2012/0010294 A1 | 1/2012 | Dill | |
| 2012/0244221 A1 | 9/2012 | Dill | |
| 2015/0044284 A1 | 2/2015 | Santus et al. | |

FOREIGN PATENT DOCUMENTS

| | | | |
|---|---|---|---|
| CN | 1658858 | 8/2005 | |
| CN | 101889996 A | 11/2010 | |
| EP | 1053752 | 11/2000 | |
| EP | 1552825 | 7/2005 | |
| EP | 1627876 | 2/2006 | |
| WO | 0119350 | 3/2001 | |
| WO | 03070233 | 8/2003 | |
| WO | 2004093864 | 11/2004 | |
| WO | 2006138609 A2 | 12/2006 | |
| WO | 2007072503 | 6/2007 | |
| WO | 2010138441 | 12/2010 | |
| WO | WO 2010138441 A1 * | 12/2010 | ........... A61K 9/2027 |
| WO | 2011107755 | 9/2011 | |
| WO | PCT/US2013/031617 | 3/2013 | |

(Continued)

OTHER PUBLICATIONS

Therapy' Sep. 2004 VHA Pharmacy Benefits Management Strategic Healthcare Group and the Medical Advisory Panel.*
U.S. Appl. No. 13/828,778, filed Mar. 14, 2013, Patented.
U.S. Appl. No. 14/815,416, filed Jul. 31, 2015, Pending.
U.S. Appl. No. 14/870,676, filed Sep. 30, 2015, Pending.
International Search Report and Written Opinion of the International Searching Authority on Patent Application No. PCT/US2016/049246, dated Nov. 4, 2016.
European Search Report issued in European Patent Application No. 13823428.1 dated Mar. 27, 2015.

(Continued)

*Primary Examiner* — Sarah Pihonak
*Assistant Examiner* — Jason Deck
(74) *Attorney, Agent, or Firm* — Ping Wang; Morris, Manning & Martin, LLP

(57) ABSTRACT

A method for manufacturing a pharmaceutical composition for reducing the frequency of urination is disclosed. The pharmaceutical composition comprises (1) an analgesic agent and (2) an α-blocker, a 5α-reductase inhibitor or both.

20 Claims, 1 Drawing Sheet

(56) References Cited

FOREIGN PATENT DOCUMENTS

WO      2013142274 A1      9/2013

OTHER PUBLICATIONS

Al-Waili, "Increased urinary nitrite excretion in primary enuresis: effects of indomethacin treatment on urinary and serum osmolality and electrolytes, urinary volumes and nitrite excretion", BJU International, vol. 90, No. 3, pp. 294-301, XP55177413, (Aug. 2002).
Deshpande, et al., "Medical management of nocturnal enuresis", Pediatric Drugs, New Zealand, vol. 14, No. 2, pp. 71-77, XP009183275, (Apr. 2002).
International Preliminary Report on Patentability and Written Opinion of the International Searching Authority of Application No. PCT/US2013/031617, dated Oct. 2, 2014.
Bisordi et al., "Interaction of Vasopressin and Prostaglandins in the Toad Urinary Bladder," Journal of Clinical Investigation, Dec. 1980, pp. 1200-1210, vol. 66.
Nusynowitz et al., "The Antidiuretic Action of Acetaminophen," The American Journal of the Medical Sciences, Oct. 1966, 77/429-83/435.
Alon et al., "Hydrochlorothiazide-Amiloride in the Treatment of Congenital Nephrogenic Diabetes insipidus" American Journal of Nephrology, 1985, pp. 9-13, vol. 5.
Asplund, "Nocturia in relation to steep, health, and medical treatment in the elderly," BJU International, 2005, pp. 15-21, vol. 96—Supplement 1.
International Search Report and Written Opinion of the International Searching Authority issued in International Patent Application No. PCT/US2012/051888 dated Jan. 17, 2013.
International Search Report and Written Opinion of the International Searching Authority, issued in International Patent Application No. PCT/US2010/061606 dated Sep. 21, 2011.
File history of U.S. Appl. No. 13/343,332, filed Jan. 4, 2012.
File history of U.S. Appl. No. 13/424,000, filed Mar. 19, 2012.
File history of U.S. Appl. No. 13/487,348, filed Jun. 4, 2012.
File history of U.S. Appl. No. 12/956,634, filed Nov. 30, 2010.
File history of U.S. Appl. No. 13/828,778, filed Mar. 14, 2013.
Painful Urination Practice, "Benign Prostatic Hyperplasia (BPH) and Nocturia (Night Urination)", 2010, vol. 18, No. 1n, pp. 32-37.
Journal published by Japan Academy of Urology, "PP-402 (0906) Effects of α1 Receptor-Blocker and 5α-Reductase Inhibitor on Canine Urination-Disorder Model", 2002, vol. 93, No. 2, p. 348.
Pinna, et al., "Altered Neurogenic and Mechanical Responses to Acetylcholine, ATP and Substance P in Detrusor From Rat with Outlet Obstruction", Life Sciences, vol. 79, No. 13, Aug. 2006, pp. 1301-1306 (Abstract Only).
Addla, et al., "Diclofenac for Treatment of Nocturia Caused by Nocturnal Polyuria: a Prospective, Randomised, Double-Blind, Placebo-Controlled Crossover Study", European Urology, vol. 49, No. 4, Apr. 2006, pp. 720-725 (Abstract Only).
Wein, et al., "Overactive Bladder: a Better Understanding of Pathophysiology, Diagnosis and Management", Journal of Urology, vol. 175, No. 3, Mar. 2006, pp. S5-S10 (Abstract Only).
Weiss, et al., "Nocturia", Journal of Urology, vol. 163, No. 1, Jan. 2000, pp. 5-12 (Abstract Only).
Matthiesen, et al., "Nocturnal Polyuria and Natriuresis in Male Patients with Nocturia and Lower Urinary Tract Symptoms", Journal of Urology, vol. 156, No. 4, Oct. 1996, pp. 1292-1299 (Abstract Only).
Smith, et al., "Outcomes of Pharmacological Management of Nocturia with Non-Antidiuretic Agents: Does Statistically Significant Equal Clinically Significant?", BJU International, vol. 107, No. 10, Aug. 2011, pp. 1550-1554 (Abstract Only).

Johnson, et al., "Changes in Nocturia from Medical Treatment of Benign Prostatic Hyperplasia: Secondary Analysis of the Department of Veterans Affairs Cooperative Study Trial", Journal of Urology, vol. 170, No. 1, Jul. 2003, pp. 145-148 (Abstract Only).
European Search Report issued in Application No. 13763665 dated Sep. 16, 2015.
Miwa, et al., "Efficacy of Combination Therapy with Tamsulosin and Zolpidem on Nocturia in Patients with Benign Prostatic Hyperplasia", Central European Journal of Urology, vol. 64, No. 4, Apr. 2011, pp. 232-235 (Abstract Only).
Yokoyama, et al., "Zolpidem Increases Bladder Capacity and Decreases Urine Excretion in Rats", Neurourology and Urodynamics, vol. 29, No. 4, Apr. 2010, pp. 587-591 (Abstract Only).
European Search Report of Application No. 13763764 dated Sep. 16, 2015.
File history of U.S. Appl. No. 14/815,416, filed Jul. 31, 2015.
Nusynowitz, M. L. et al., "Effect on vasopressin action of analgesic drugs in vitro", The American Journal of the Medical Sciences, Oct. 1966, vol. 252(4), pp. 424-428.
Tie, Y., "Encyclopedia of Family Medical Treatment", Hualing Press, Jan. 1997, p. 151. (English Abstract).
Cai, M., "TCM Perspective of Clinical Diseases: A handbook of Common Internal Diseases", Henan Science and Technology Press, Jan. 2012, pp. 126-127. (English Abstract).
Satoru Takahashi et.al., "Diagnosis and Treatment of Overactive Bladder Syndrome", Gerontology, New Horizon, 2005, vol. 17, No. 2, pp. 76-81.
Osamu Yamaguchi, "Latest Treatment for Lower Urinary Tract Dysfunction: Therapeutic Agents and Mechanism of Action", International Journal of Urology, 2013, vol. 20, pp. 28-39.
Kaplan et al., "Urinary Retention and Post-Void Residual Urine in Men: Separating Truth From Tradition", The Journal of Urology, May 2008, vol. 180, issue. 1, pp. 47-54.
Song et al., "Zolpidem Pharmacotherapy Combined with Alpha-Blocker Therapy for Nocturia Unresponsive to Alpha-Blocker Monotherapy in Men with Lower Urinary Tract Symptoms: a Preliminary Study", International Urology Nephrology, 2007, vol. 39, pp. 1147-1152.
Robinson et al., "A Randomized Double-Blind Placebo-controlled Multicentre Study to Explore the Efficacy and Safety of Tamsulosin and Tolterodine in Women with Overactive Bladder Syndrome", BJU International, Oct. 2007, vol. 100, issue. 4, pp. 840-845.
Ozdemir et al., "Combination Therapy With Doxazosin and Tenoxicam for the Management of Lower Urinary Tract Symptoms", Urology, Aug. 2009, vol. 74, issue. 2, pp. 431-435.
Johnson et al., "The Effect of Doxazosin, Finasteride and Combination Therapy on Nocturia in Men With Benign Prostatic Hyperplasia", The Journal of Urology, Nov. 2007, vol. 178, issue. 5, pp. 2045-2051.
Smith et al., "Outcomes of Pharmacological Management of Nocturia with Non-autidiuretic Agents: Does Statistically Significant Equal Clinically Significant", BJU International, May 2011, vol. 107, issue. 10, pp. 1550-1554.
Johnson et al., "Changes in Nocturia from Medical Treatment of Benign Prostatic Hyperplasia: Secondary Analysis of the Department of Veterans Affairs Cooperative Study Trial", Journal of Urology, Jul. 2013, vol. 170, issue 1, pp. 145-148.
Search Report and Written Opinion of the Intellectual Property Office of Singapore, Application No. 11201500409S, dated Feb. 10, 2016.
Lopatkin N.A., "Urology", "Geotar-Media", 2002, pp. 216.
Pushkar. D.Yu et al., "Therapy with Alpha-Blockers: Procedure of Choice in the Treatment of Obstructive Urination in Men and Women", Pharmatheka, 2002, No. 10, pp. 12-22.
Mazo E.B. et al., "Tonocardin (Doxazosin) in Treating Lower Urinary Tract Symptoms", "Urologiia", 2003, vol. 3. May-June, pp. 15-16, abstract.

* cited by examiner

COMPOSITION FOR REDUCING THE FREQUENCY OF URINATION, METHOD OF MAKING AND USE THEREOF

This application is a continuation-in-part of U.S. patent application Ser. No. 14/815,416, filed on Jul. 31, 2015, which is a continuation application of U.S. patent application Ser. No. 13/828,778, filed on Mar. 14, 2013, now U.S. Pat. No. 9,119,878. The entirety of the aforementioned applications is incorporated herein by reference.

FIELD

The present application generally relates to methods and compositions for inhibiting the contraction of muscles and, in particular, to methods and compositions for inhibiting the contraction of smooth muscles of the urinary bladder.

BACKGROUND

The detrusor muscle is a layer of the urinary bladder wall made of smooth muscle fibers arranged in spiral, longitudinal, and circular bundles. When the bladder is stretched, this signals the parasympathetic nervous system to contract the detrusor muscle. This encourages the bladder to expel urine through the urethra.

For the urine to exit the bladder, both the autonomically controlled internal sphincter and the voluntarily controlled external sphincter must be opened. Problems with these muscles can lead to incontinence. If the amount of urine reaches 100% of the urinary bladder's absolute capacity, the voluntary sphincter becomes involuntary and the urine will be ejected instantly.

The human adult urinary bladder usually holds about 300-350 ml of urine (the working volume), but a full adult bladder may hold up to about 1000 ml (the absolute volume), varying among individuals. As urine accumulates, the ridges produced by folding of the wall of the bladder (rugae) flatten and the wall of the bladder thins as it stretches, allowing the bladder to store larger amounts of urine without a significant rise in internal pressure.

In most individuals, the desire to urinate usually starts when the volume of urine in the bladder reaches around 200 ml. At this stage it is easy for the subject, if desired, to resist the urge to urinate. As the bladder continues to fill, the desire to urinate becomes stronger and harder to ignore. Eventually, the bladder will fill to the point where the urge to urinate becomes overwhelming, and the subject will no longer be able to ignore it. In some individuals, this desire to urinate starts when the bladder is less than 100% full in relation to its working volume. Such increased desire to urinate may interfere with normal activities, including the ability to sleep for sufficient uninterrupted periods of rest. In some cases, this increased desire to urinate may be associated with medical conditions such as benign prostate hyperplasia or prostate cancer in men, or pregnancy in women. However, increased desire to urinate also occurs in individuals, both male and female, who are not affected by another medical condition.

Accordingly, there exists a need for compositions and methods for the treatment of male and female subjects who suffer from a desire to urinate when the bladder is less than 100% full of urine in relation to its working volume. Said compositions and methods are needed for the inhibition of muscle contraction in order to allow in said subjects the desire to urinate to start when the volume of urine in the bladder exceeds around 100% of its working volume.

SUMMARY

One aspect of the present application relates to methods of manufacturing extended-release pharmaceutical compositions for reducing the frequency of urination. In some embodiments, the method comprises the steps of forming a first mixture having a first active ingredient formulated for immediate release and a second active ingredient formulated for extended release; coating the first mixture with a delayed release coating to form a core structure; and then coating the core structure with a second mixture comprising a third active ingredient formulated for immediate release and a fourth active ingredient formulated for extended release, wherein at least one of the first, second, third and fourth active ingredients comprises an analgesic agent and at least one of the first, second, third and fourth active ingredients comprises an α-blocker, a 5α-reductase inhibitor or both.

Another aspect of the present application relates to a method for manufacturing a pharmaceutical composition for reducing the frequency of urination. The method comprises the steps of forming a core structure comprising a first active ingredient formulated for immediate release and a second active ingredient formulated for extended release; coating the core structure with a delayed release coating to form a coated core structure; coating the coated core structure with a third active ingredient formulated for extended release to form an extended-release layer coated core structure, and coating the extended-release layer coated core structure with a fourth active ingredient, wherein at least one of the first, second, third and fourth active ingredients comprises an analgesic agent and at least one of the first, second, third and fourth active ingredients comprises an α-blocker, a 5α-reductase inhibitor or both.

Another aspect of the present application relates to a method for manufacturing a pharmaceutical composition for reducing the frequency of urination. The method comprises the steps of forming a core structure comprising a first active ingredient formulated for immediate release and a second active ingredient formulated for extended release; coating the core structure with a delayed release coating to form a coated core structure; coating the coated core structure with a third active ingredient formulated for immediate release to form a double-coated core structure, wherein at least one of the first, second and third active ingredients comprises an analgesic agent and at least one of the first, second and third active ingredients comprises an α-blocker, a 5α-reductase inhibitor or both.

Another aspect of the present application relates to a pharmaceutical composition, comprising: a first component comprising an immediate-release subcomponent and an extended-release subcomponent, wherein the first component is formulated to release the subcomponents immediately after administration; and a second component comprising an immediate-release subcomponent and an extended-release subcomponent, wherein the second component is formulated for a delayed-release of the subcomponents, wherein the immediate-release subcomponent and the extended-release subcomponent in the first component each comprises an active ingredient comprising one or more agents selected from the group consisting of analgesic agents, α-blockers and 5α-reductase inhibitors' wherein the immediate-release subcomponent and the extended-release subcomponent in the second component each comprises an active ingredient comprising one or more agents selected from the group consisting of analgesic agents, α-blockers and 5α-reductase inhibitors.

Another aspect of the present application relates to a pharmaceutical composition, comprising: a first component comprising an immediate-release subcomponent, wherein the immediate-release subcomponent comprises an active ingredient comprising one or more agents selected from the group consisting of analgesic agents, α-blockers and 5α-reductase inhibitors, wherein the first component is formulated to release its subcomponent immediately after oral administration; and a second component comprising an immediate-release subcomponent and an extended-release subcomponent, wherein the second component is formulated to release its subcomponent after gastric emptying of the second component, wherein the immediate-release subcomponent and the extended-release subcomponent in the second component each comprises an active ingredient comprising one or more agents selected from the group consisting of analgesic agents, α-blockers and 5α-reductase inhibitors.

Another aspect of the present application relates to a pharmaceutical composition for reducing the frequency of urination, comprising: a first component comprising an immediate-release subcomponent and an extended-release subcomponent, wherein the first component is formulated to release the subcomponents immediately after administration; and a second component comprising an immediate-release subcomponent and an extended-release subcomponent, wherein the second component is formulated for a delayed-release of the subcomponents, wherein the immediate-release subcomponent and the extended-release subcomponent in the first component each comprises an active ingredient comprising (1) acetaminophen, and (2) tamsulosin or finasteride or both, wherein the immediate-release subcomponent and the extended-release subcomponent in the second component each comprises an active ingredient comprising (1) acetaminophen, and (2) tamsulosin or finasteride or both, wherein the pharmaceutical composition reduces the frequency of urination in patients in need thereof.

Another aspect of the present application relates to a pharmaceutical composition, comprising: an immediate-release component comprising acetaminophen and an NSAID, each in an amount of 5-2000 mg; and an extended-release component comprising acetaminophen and an NSAID, each in an amount of 5-2000 mg, wherein the immediate-release component, or the extended-release component, or both, further comprise one or more agent selected from the group consisting of α-blockers and 5α-reductase inhibitors.

DETAILED DESCRIPTION

Figure 1A:
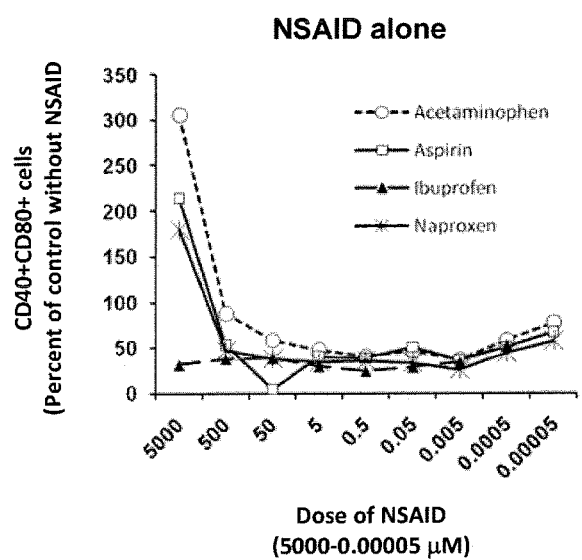
FIGS. 1A and 1B are diagrams showing that analgesics regulate expression of co-stimulatory molecules by Raw 264 macrophage cells in the absence (FIG. 1A) or presence (FIG. 1B) of LPS. Cells were cultures for 24 hrs in the presence of analgesic alone or together with *Salmonella typhimurium* LPS (0.05 μg/ml). Results are mean relative % of CD40+ CD80+ cells.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the broadest possible scope consistent with the principles and features disclosed herein.

As used herein, the term "an effective amount" means an amount necessary to achieve a selected result.

As used herein, the term "analgesic" refers to agents, compounds or drugs used to relieve pain and inclusive of anti-inflammatory compounds. Exemplary analgesic and/or anti-inflammatory agents, compounds or drugs include, but are not limited to, the following substances: non-steroidal anti-inflammatory drugs (NSAIDs), salicylates, aspirin, salicylic acid, methyl salicylate, diflunisal, salsalate, olsalazine, sulfasalazine, para-aminophenol derivatives, acetanilide, acetaminophen, phenacetin, fenamates, mefenamic acid, meclofenamate, sodium meclofenamate, heteroaryl acetic acid derivatives, tolmetin, ketorolac, diclofenac, propionic acid derivatives, ibuprofen, naproxen sodium, naproxen, fenoprofen, ketoprofen, flurbiprofen, oxaprozin; enolic acids, oxicam derivatives, piroxicam, meloxicam, tenoxicam, ampiroxicam, droxicam, pivoxicam, pyrazolon derivatives, phenylbutazone, oxyphenbutazone, antipyrine, aminopyrine, dipyrone, coxibs, celecoxib, rofecoxib, nabumetone, apazone, indomethacin, sulindac, etodolac, isobutylphenyl propionic acid, lumiracoxib, etoricoxib, parecoxib, valdecoxib, tiracoxib, etodolac, darbufelone, dexketoprofen, aceclofenac, licofelone, bromfenac, loxoprofen, pranoprofen, piroxicam, nimesulide, cizolirine, 3-formylamino-7-methylsulfonylamino-6-phenoxy-4H-1-benzopyran-4-one, meloxicam, lornoxicam, d-indobufen, mofezolac, amtolmetin, pranoprofen, tolfenamic acid, flurbiprofen, suprofen, oxaprozin, zaltoprofen, alminoprofen, tiaprofenic acid, pharmacological salts thereof, hydrates thereof, and solvates thereof.

As used herein, the terms "coxib" and "COX inhibitor" refer to a composition of compounds that is capable of inhibiting the activity or expression of COX1 and/or COX2 enzymes or is capable of inhibiting or reducing the severity, including pain and swelling, of a severe inflammatory response.

As used herein, the term "derivative" refers to a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

As used herein, the term "analogue" refers to a compound which comprises a chemically modified form of a specific compound or class thereof, and which maintains the pharmaceutical and/or pharmacological activities characteristic of said compound or class.

As used herein "subject" or "patient" encompasses mammals. In one aspect, the mammal is a human. In another aspect, the mammal is a non-human primate such as chimpanzee, and other apes and monkey species. In one aspect, the mammal is a domestic animal such as rabbit, dog, or cat. In another aspect, the mammal is a farm animal such as cattle, horse, sheep, goat, or swine. In another aspect, the mammal is a laboratory animal, including rodents, such as rats, mice and guinea pigs, and the like.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluensulfonic, methanesulfonic, ethane dislfonic, oxalic, isethionic, and the like.

As used herein, the phrase "pharmaceutically acceptable" is used with reference to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The urinary bladder has two important functions: storage of urine and emptying. Storage of urine occurs at low pressure, which implies that the detrusor muscle relaxes during the filling phase. Emptying of the bladder requires a coordinated contraction of the detrusor muscle and relaxation of the sphincter muscles of the urethra. Disturbances of the storage function may result in lower urinary tract symptoms, such as urgency, frequency, and urge incontinence, the components of the overactive bladder syndrome. The overactive bladder syndrome, which may be due to involuntary contractions of the smooth muscle of the bladder (detrusor) during the storage phase, is a common and underreported problem, the prevalence of which has only recently been assessed.

One aspect of the present application relates to a method for reducing the frequency of urination. The method comprises administering to a subject in need thereof an effective amount of one or more analgesic agents, and an effective amount of an α-blocker. In some embodiments, the one or more analgesic agents and the α-blocker are administered separately in different dosage forms. In other embodiments, the one or more analgesic agents and the α-blocker are administered simultaneously in a single dosage form (e.g., in a single pill or tablet). In some embodiments, both the one or more analgesic agents and the α-blocker are formulated for immediate release after administration. In other embodiments, both the one or more analgesic agents and the α-blocker are formulated for delayed-release after administration. In other embodiments, both the one or more analgesic agents and the α-blocker are formulated for extended release after administration. In other embodiments, both the one or more analgesic agents and the α-blocker are formulated for delayed-extended release after administration. In other embodiments, the one or more analgesic agents are formulated for delayed-release, extended release or delayed extended release, and the α-blocker is formulated for immediate release. In yet other embodiments, the one or more analgesic agents are formulated for immediate release, and the α-blocker is formulated for delayed-release, extended release or delayed extended release. The method can be used for the treatment of nocturia or overactive bladder. Another aspect of the present application relates to a pharmaceutical composition comprising an active ingredient comprising one or more analgesic agents, an α-blocker, and a pharmaceutically acceptable carrier.

Alpha-blockers, also called α-adrenergic-antagonists or α-blockers, are pharmacological agents that act as receptor antagonists of α-adrenergic receptors, which are further divided into α1-adrenergic receptors and α2-adrenergic receptors. Alpha blockers can be classified as selective blockers that selectively act at α1-adrenoceptors or α2-adrenoceptors, and non-selective alpha blockers that act at both types of α-adrenergic receptors.

Examples of selective α1-adrenergic blockers include, but are not limited to, alfuzosin, prazosin, doxazosin, tamsulosin, terazosin, carvedilol, labetalol and silodosin. Examples of selective α2-adrenergic blockers include, but are not limited to, atipamezole, idazoxane and yohimbine. Examples of non-selective α-adrenergic blockers include: phenoxybenzamine, phentolamine, tolazoline, trazodone, typical and atypical antipsychotics.

In some embodiments, the one or more analgesic agents are administered orally in an individual or combined daily dose of 50-2000 mg, 50-1500 mg, 50-1200 mg, 50-1000 mg, 50-800 mg, 50-600 mg, 50-500 mg, 50-400 mg, 50-300 mg, 50-250 mg, 50-200 mg, 50-100 mg, 100-2000 mg, 100-1500 mg, 100-1200 mg, 100-1000 mg, 100-800 mg, 100-600 mg, 100-500 mg, 100-400 mg, 100-300 mg, 100-200 mg, 200-2000 mg, 200-1500 mg, 200-1200 mg, 200-1000 mg, 200-800 mg, 200-600 mg, 200-400 mg, 400-2000 mg, 400-1500 mg, 400-1200 mg, 400-1000 mg, 400-800 mg, 400-600 mg, 600-2000 mg, 600-1500 mg, 600-1200 mg, 600-1000 mg, 600-800 mg, 800-2000 mg, 800-1500 mg, 800-1200 mg, 800-1000 mg, 1000-2000 mg, 1000-1500 mg, 1000-1200 mg, 1200-2000 mg, 1200-1500 mg or 1500-2000 mg; and the one or more α-blockers are administered orally in an individual or combined daily dose of between 0.01-100 mg, 0.01-30 mg, 0.01-10 mg, 0.01-3 mg, 0.01-1 mg, 0.01-0.3 mg, 0.01-0.1 mg, 0.01-0.03 mg, 0.03-100 mg, 0.03-30 mg, 0.03-10 mg, 0.03-3 mg, 0.03-1 mg, 0.03-0.3 mg, 0.03-0.1 mg, 0.1-100 mg, 0.1-30 mg, 0.1-10 mg, 0.1-3 mg, 0.1-1 mg, 0.1-0.3 mg, 0.3-100 mg, 0.3-30 mg, 0.3-10 mg, 0.3-3 mg, 0.3-1 mg and 0.2-1 mg.

In some embodiments, the α-blocker is a non-selective α-blocker. In other embodiments, the α-blocker is a selective α1-adrenergic blocker. In other embodiments, the α-blocker is a selective α2-adrenergic blocker. In other embodiments, the α-blocker is tamsulosin.

Another aspect of the present application relates to a pharmaceutical composition comprising: one or more analgesic agents; one or more α-blockers; and a pharmaceutically acceptable carrier. In some embodiments, the one or more analgesic agents are selected from the group consisting of aspirin, ibuprofen, naproxen, naproxen sodium, indomethacin, nabumetone, and acetaminophen.

In some embodiments, the pharmaceutical composition comprises one or more analgesic agent(s), individually or in combination, in an amount between 50-2000 mg, 50-1500 mg, 50-1200 mg, 50-1000 mg, 50-800 mg, 50-600 mg, 50-500 mg, 50-400 mg, 50-300 mg, 50-250 mg, 50-200 mg, 50-100 mg, 100-2000 mg, 100-1500 mg, 100-1200 mg, 100-1000 mg, 100-800 mg, 100-600 mg, 100-500 mg, 100-400 mg, 100-300 mg, 100-200 mg, 200-2000 mg, 200-1500 mg, 200-1200 mg, 200-1000 mg, 200-800 mg, 200-600 mg, 200-400 mg, 400-2000 mg, 400-1500 mg, 400-1200 mg, 400-1000 mg, 400-800 mg, 400-600 mg, 600-2000 mg, 600-1500 mg, 600-1200 mg, 600-1000 mg, 600-800 mg, 800-2000 mg, 800-1500 mg, 800-1200 mg, 800-1000 mg, 1000-2000 mg, 1000-1500 mg, 1000-1200 mg, 1200-2000 mg, 1200-1500 mg or 1500-2000 mg; and one or more α-blockers in an amount between 0.01-100 mg, 0.01-30 mg, 0.01-10 mg, 0.01-3 mg, 0.01-1 mg, 0.01-0.3 mg, 0.01-0.1 mg, 0.01-0.03 mg, 0.03-100 mg, 0.03-30 mg, 0.03-10 mg, 0.03-3 mg, 0.03-1 mg, 0.03-0.3 mg, 0.03-0.1 mg, 0.1-100 mg, 0.1-30 mg, 0.1-10 mg, 0.1-3 mg, 0.1-1 mg, 0.1-0.3 mg, 0.3-100 mg, 0.3-30 mg, 0.3-10 mg, 0.3-3 mg, 0.3-1 mg and 0.2-1 mg.

In some embodiments, the α-blocker is a non-selective α-blocker. In other embodiments, the α-blocker is a selective α1-adrenergic blocker. In other embodiments, the α-blocker is a selective α2-adrenergic blocker. In other embodiments, the α-blocker is tamsulosin.

In some embodiments, the pharmaceutical composition comprises acetaminophen in an amount between 100-200 mg, 200-400 mg, 400-600 mg, 600-800 mg, 800-1000 mg, or 1000-1200 mg and tamsulosin in an amount between 0.1-0.3 mg, 0.3-0.6 mg, 0.6-0.9 mg, 0.9-1.2 mg or 1.2-1.5 mg.

In other embodiments, both the one or more analgesic agents and the one or more α-blockers are formulated for immediate release. In other embodiments, the one or more analgesic agents are formulated for immediate release and the one or more α-blockers are formulated for extended release.

In other embodiments, the one or more analgesic agents are formulated for extended release and the one or more α-blockers are formulated for immediate release. In some embodiments, the one or more analgesic agents are released continuously, or at a steady rate, over a period or 5-24 hours, 5-8 hours, 8-16 hours or 16-24 hours. In some embodiments, at least 90% of the one or more analgesic agents are released continuously, or at a steady rate, over a period or 5-24 hours, 5-8 hours, 8-16 hours or 16-24 hours.

In some other embodiments, the one or more analgesic agents are released within 2 hours of administration and the remainder are released continuously, or at a steady rate, over a period of 5-24 hours, 5-8 hours, 8-16 hours or 16-24 hours.

In other embodiments, both the one or more analgesic agents and the one or more α-blockers are formulated for extended release. In some embodiments, both the one or more analgesic agents and the one or more α-blockers are formulated for extended release such that the one or more analgesic agents and the one or more α-blockers are released continuously, or at a steady rate, over a period or 5-24 hours, 5-8 hours, 8-16 hours or 16-24 hours. In some other embodiments, both the one or more analgesic agents and the one or more α-blockers are formulated for extended release with a two-phase release profile in which 20-60% of the that the one or more analgesic agents and the one or more α-blockers are released within 2 hours of administration and the remainder are released continuously, or at a steady rate, over a period of 5-24 hours, 5-8 hours, 8-16 hours or 16-24 hours.

In some embodiments, the pharmaceutical composition comprises acetaminophen in amount between 50-1000 mg, 50-250 mg, 250-400 mg, 400-600 mg, 600-800 mg or 800-1000 mg in combination with tamsulosin in an amount between 0.1-1.2 mg, 0.1-0.3 mg, 0.3-0.6 mg, 0.6-0.9 mg or 0.9-1.2 mg, wherein the composition is formulated for extended release of both acetaminophen and tamsulosin with a drug release profile in which at least 90% of the acetaminophen and tamsulosin is released, continuously, or at a steady rate, over a period of 5-24 hours, 5-8 hours, 8-16 hours or 16-24 hours.

In other embodiments, the pharmaceutical composition comprises acetaminophen in an amount between 500-1000 mg, 50-200 mg, 50-400 mg, 100-400 mg, 100-300 mg, 200-400 mg, 400-600 mg, 600-800 mg, 800-1000 mg, or 1000-1200 mg and tamsulosin in an amount between 0.1-1.2 mg, 0.1-0.3 mg, 0.3-0.6 mg, 0.6-0.9 mg or 0.9-1.2 mg, wherein the composition is formulated for extended release with a two-phase release profile in which 20-60% of the acetaminophen and tamsulosin are released within 2 hours of administration, and the remainder are released, continuously, or at a steady rate, in a period of 5-24 hours, 5-8 hours, 8-16 hours or 16-24 hours.

"Extended-release," also known as sustained-release (SR), sustained-action (SA), time-release (TR), controlled-release (CR), modified release (MR), or continuous-release (CR), is a mechanism used in medicine tablets or capsules to dissolve slowly and release the active ingredient over time. The advantages of extended-release tablets or capsules are that they can often be taken less frequently than immediate-release formulations of the same drug, and that they keep steadier levels of the drug in the bloodstream, thus extending the duration of the drug action and lowering the peak amount of drug in the bloodstream. For example, an extended-release analgesic may allow a person to sleep through the night without getting up for the bathroom.

In one embodiment, the pharmaceutical composition is formulated for extended-release by embedding the active ingredient in a matrix of insoluble substance(s) such as acrylics or chitin. An extended-release form is designed to release the analgesic compound at a predetermined rate by maintaining a constant drug level for a specific period of time. This can be achieved through a variety of formulations, including, but not limited to, liposomes and drug-polymer conjugates, such as hydrogels.

An extended-release formulation can be designed to release the active agents at a predetermined rate so as to maintain a constant drug level for a specified, extended period of time, such as up to about 24 hours, about 20 hours, about 16 hours, about 12 hours, about 10 hours, about 9 hours, about 8 hours, about 7 hours, about 6 hours, about 5 hours, about 4 hours, about 3 hours, about 2 hours, or about 1 hour following administration or following a lag period associated with delayed-release of the drug.

In certain preferred embodiments, the active agents are released over a time interval of between about 2 to about 10 hours. Alternatively, the active agents may be released over about 3 hours, about 4 hours, about 5 hours, about 6 hours, about 7 hours, about 8 hours, about 9, about 10 hours, about 12 hours, about 16 hours, about 20 hours or about 24 hours. In yet other embodiments, the active agents are released over a time period between about three to about eight hours following administration.

In some embodiments, the extended-release formulation comprises an active core comprised of one or more inert particles, each in the form of a bead, pellet, pill, granular particle, microcapsule, microsphere, microgranule, nanocapsule, or nanosphere coated on its surfaces with drugs in the form of e.g., a drug-containing coating or film-forming composition using, for example, fluid bed techniques or other methodologies known to those of skill in the art. The inert particle can be of various sizes, so long as it is large enough to remain poorly dissolved. Alternatively, the active core may be prepared by granulating and milling and/or by extrusion and spheronization of a polymer composition containing the drug substance.

The active agents may be introduced to the inert carrier by techniques known to one skilled in the art, such as drug layering, powder coating, extrusion/spheronization, roller compaction or granulation. The amount of drug in the core will depend on the dose that is required, and typically varies from about 5 to 90 weight %. Generally, the polymeric coating on the active core will be from about 1 to 50% based on the weight of the coated particle, depending on the lag time required and/or the polymers and coating solvents chosen. Those skilled in the art will be able to select an appropriate amount of drug for coating onto or incorporating into the core to achieve the desired dosage. In one embodiment, the inactive core may be a sugar sphere or a buffer crystal or an encapsulated buffer crystal such as calcium carbonate, sodium bicarbonate, fumaric acid, tartaric acid, etc. which alters the microenvironment of the drug to facilitate its release.

Another aspect of the present application relates to a method for reducing the frequency of urination. The method comprises administering to a subject in need thereof an effective amount of one or more analgesic agents, and an effective amount of a 5α-reductase inhibitor. Examples of 5α-reductase inhibitors include, but are not limited to, finasteride, bexlosteride, epristeride, izonsteride, lapisteride, and turosteride. In some embodiments, the 5α-reductase inhibitor is finasteride.

In some embodiments, the one or more analgesic agents and the 5α-reductase inhibitor are administered separately in different dosage forms. In other embodiments, the one or more analgesic agents and the α-blocker are administered simultaneously in a single dosage form (e.g., in a single pill or tablet). In some embodiments, both the one or more analgesic agents and the 5α-reductase inhibitor are formulated for immediate release after administration. In other embodiments, both the one or more analgesic agents and the 5α-reductase inhibitor are formulated for delayed-release after administration. In other embodiments, both the one or more analgesic agents and the 5α-reductase inhibitor are formulated for extended release after administration. In other embodiments, both the one or more analgesic agents and the 5α-reductase inhibitor are formulated for delayed-extended release after administration. In other embodiments, the one or more analgesic agents are formulated for delayed-release, extended release or delayed extended release, and the 5α-reductase inhibitor is formulated for immediate release. In yet other embodiments, the one or more analgesic agents are formulated for immediate release, and the 5α-reductase inhibitor is formulated for delayed-release, extended release or delayed extended release. The method can be used for the treatment of nocturia or overactive bladder. Another aspect of the present application relates to a pharmaceutical composition comprising an active ingredient comprising one or more analgesic agents, a 5α-reductase inhibitor, and a pharmaceutically acceptable carrier.

In some embodiments, the one or more analgesic agents are administered orally in an individual or combined daily dose of 50-2000 mg, 50-1500 mg, 50-1200 mg, 50-1000 mg, 50-800 mg, 50-600 mg, 50-500 mg, 50-400 mg, 50-300 mg, 50-250 mg, 50-200 mg, 50-100 mg, 100-2000 mg, 100-1500 mg, 100-1200 mg, 100-1000 mg, 100-800 mg, 100-600 mg, 100-500 mg, 100-400 mg, 100-300 mg, 100-200 mg, 200-2000 mg, 200-1500 mg, 200-1200 mg, 200-1000 mg, 200-800 mg, 200-600 mg, 200-400 mg, 400-2000 mg, 400-1500 mg, 400-1200 mg, 400-1000 mg, 400-800 mg, 400-600 mg, 600-2000 mg, 600-1500 mg, 600-1200 mg, 600-1000 mg, 600-800 mg, 800-2000 mg, 800-1500 mg, 800-1200 mg, 800-1000 mg, 1000-2000 mg, 1000-1500 mg, 1000-1200 mg, 1200-2000 mg, 1200-1500 mg or 1500-2000 mg; and the one or more 5α-reductase inhibitors are administered orally in an individual or combined daily dose of between 0.1-250 mg, 0.1-100 mg, 0.1-30 mg, 0.1-10 mg, 0.1-3 mg, 0.1-1 mg, 0.3-250 mg, 0.3-100 mg, 0.3-30 mg, 0.3-10 mg, 0.3-3 mg, 0.3-1 mg, 1-100 mg, 1-30 mg, 1-10 mg, 1-3 mg, 3-7 mg and 4-6 mg.

In some embodiments, the 5α-reductase inhibitor is tamsulosin.

Another aspect of the present application relates to a pharmaceutical composition comprising: one or more analgesic agents; one or more 5α-reductase inhibitors; and a pharmaceutically acceptable carrier. In some embodiments, the one or more analgesic agents are selected from the group consisting of aspirin, ibuprofen, naproxen, naproxen sodium, indomethacin, nabumetone, and acetaminophen.

In some embodiments, the pharmaceutical composition comprises one or more analgesic agent(s), individually or in combination, in an amount between 50-2000 mg, 50-1500 mg, 50-1200 mg, 50-1000 mg, 50-800 mg, 50-600 mg, 50-500 mg, 50-400 mg, 50-300 mg, 50-250 mg, 50-200 mg, 50-100 mg, 100-2000 mg, 100-1500 mg, 100-1200 mg, 100-1000 mg, 100-800 mg, 100-600 mg, 100-500 mg, 100-400 mg, 100-300 mg, 100-200 mg, 200-2000 mg, 200-1500 mg, 200-1200 mg, 200-1000 mg, 200-800 mg, 200-600 mg, 200-400 mg, 400-2000 mg, 400-1500 mg, 400-1200 mg, 400-1000 mg, 400-800 mg, 400-600 mg, 600-2000 mg, 600-1500 mg, 600-1200 mg, 600-1000 mg, 600-800 mg, 800-2000 mg, 800-1500 mg, 800-1200 mg, 800-1000 mg, 1000-2000 mg, 1000-1500 mg, 1000-1200 mg, 1200-2000 mg, 1200-1500 mg or 1500-2000 mg; and one or more 5α-reductase inhibitor in an amount between 0.1-250 mg, 0.1-100 mg, 0.1-30 mg, 0.1-10 mg, 0.1-3 mg, 0.1-1 mg, 0.3-250 mg, 0.3-100 mg, 0.3-30 mg, 0.3-10 mg, 0.3-3 mg, 0.3-1 mg, 1-100 mg, 1-30 mg, 1-10 mg, 1-3 mg, 3-7 mg and 4-6 mg.

In some embodiments, the α-blocker is a non-selective α-blocker. In other embodiments, the α-blocker is a selective α1-adrenergic blocker. In other embodiments, the α-blocker is a selective α2-adrenergic blocker. In other embodiments, the α-blocker is tamsulosin.

In some embodiments, the pharmaceutical composition comprises acetaminophen in an amount between 100-200 mg, 200-400 mg, 400-600 mg, 600-800 mg, 800-1000 mg, or 1000-1200 mg and finasteride in an amount between 0.1-0.3 mg, 0.3-0.6 mg, 0.6-0.9 mg, 0.9-1.2 mg or 1.2-1.5 mg.

In other embodiments, both the one or more analgesic agents and the one or more 5α-reductase inhibitors are formulated for immediate release. In other embodiments, the one or more analgesic agents are formulated for immediate release and the one or more α-blockers are formulated for extended release.

In other embodiments, the one or more analgesic agents are formulated for extended release and the one or more 5α-reductase inhibitors are formulated for immediate release. In some embodiments, the one or more analgesic agents are released continuously, or at a steady rate, over a period or 5-24 hours, 5-8 hours, 8-16 hours or 16-24 hours. In some embodiments, at least 90% of the one or more analgesic agents are released continuously, or at a steady rate, over a period or 5-24 hours, 5-8 hours, 8-16 hours or 16-24 hours.

In some other embodiments, the one or more analgesic agents are released within 2 hours of administration and the remainder are released continuously, or at a steady rate, over a period of 5-24 hours, 5-8 hours, 8-16 hours or 16-24 hours.

In other embodiments, both the one or more analgesic agents and the one or more 5α-reductase inhibitors are formulated for extended release. In some embodiments, both the one or more analgesic agents and the one or more 5α-reductase inhibitors are formulated for extended release such that the one or more analgesic agents and the one or more 5α-reductase inhibitors are released continuously, or at a steady rate, over a period or 5-24 hours, 5-8 hours, 8-16 hours or 16-24 hours. In some other embodiments, both the one or more analgesic agents and the one or more 5α-reductase inhibitors are formulated for extended release with a two-phase release profile in which 20-60% of the that the one or more analgesic agents and the one or more 5α-reductase inhibitors are released within 2 hours of administration and the remainder are released continuously, or at a steady rate, over a period of 5-24 hours, 5-8 hours, 8-16 hours or 16-24 hours.

In some embodiments, the pharmaceutical composition comprises acetaminophen in amount between 50-1000 mg, 50-250 mg, 250-400 mg, 400-600 mg, 600-800 mg or 800-1000 mg in combination with finasteride in an amount between 1-20 mg, 1-3 mg, 3-7 mg, 7-10 mg, 10-15 mg or 15-20 mg, wherein the composition is formulated for extended release of both acetaminophen and finasteride with a drug release profile in which at least 90% of the acetaminophen and finasteride is released, continuously, or at a steady rate, over a period of 5-24 hours, 5-8 hours, 8-16 hours or 16-24 hours.

In other embodiments, the pharmaceutical composition comprises acetaminophen in an amount between 50-1000 mg, 50-100 mg, 50-200 mg, 50-300 mg, 50-400 mg, 50-600 mg, 50-800 mg, 100-200 mg, 100-300 mg, 100-400 mg, 100-600 mg, 100-800 mg, 100-1000 mg, 200-400 mg, 200-600 mg, 200-800 mg, 200-1000 mg, 400-600 mg, 400-800 mg, 400-1000 mg, 600-800 mg, 600-1000 mg, 800-1000 mg, or 1000-1200 mg and finasteride in an amount between 1-20 mg, 1-3 mg, 1-7 mg, 1-10 mg, 1-15 mg, 3-7 mg, 3-10 mg, 3-15 mg, 3-20 mg, 7-10 mg, 7-15 mg, 7-20 mg, 10-15 mg, 10-20 mg or 15-20 mg, wherein the composition is formulated for extended release with a two-phase release profile in which 20-60% of the acetaminophen and finasteride are released within 2 hours of administration, and the remainder are released, continuously, or at a steady rate, in a period of 5-24 hours, 5-8 hours, 8-16 hours or 16-24 hours.

"Extended-release," also known as sustained-release (SR), sustained-action (SA), time-release (TR), controlled-release (CR), modified release (MR), or continuous-release (CR), is a mechanism used in medicine tablets or capsules to dissolve slowly and release the active ingredient over time. The advantages of extended-release tablets or capsules are that they can often be taken less frequently than immediate-release formulations of the same drug, and that they keep steadier levels of the drug in the bloodstream, thus extending the duration of the drug action and lowering the peak amount of drug in the bloodstream. For example, an extended-release analgesic may allow a person to sleep through the night without getting up for the bathroom.

In one embodiment, the pharmaceutical composition is formulated for extended-release by embedding the active ingredient in a matrix of insoluble substance(s) such as acrylics or chitin. An extended-release form is designed to release the analgesic compound at a predetermined rate by maintaining a constant drug level for a specific period of time. This can be achieved through a variety of formulations, including, but not limited to, liposomes and drug-polymer conjugates, such as hydrogels.

An extended-release formulation can be designed to release the active agents at a predetermined rate so as to maintain a constant drug level for a specified, extended period of time, such as up to about 24 hours, about 20 hours, about 16 hours, about 12 hours, about 10 hours, about 9 hours, about 8 hours, about 7 hours, about 6 hours, about 5 hours, about 4 hours, about 3 hours, about 2 hours, or about 1 hour following administration or following a lag period associated with delayed-release of the drug.

In certain preferred embodiments, the active agents are released over a time interval of between about 2 to about 10 hours. Alternatively, the active agents may be released over about 3 hours, about 4 hours, about 5 hours, about 6 hours, about 7 hours, about 8 hours, about 9, about 10 hours, about 12 hours, about 16 hours, about 20 hours or about 24 hours. In yet other embodiments, the active agents are released over a time period between about three to about eight hours following administration.

In some embodiments, the extended-release formulation comprises an active core comprised of one or more inert particles, each in the form of a bead, pellet, pill, granular particle, microcapsule, microsphere, microgranule, nanocapsule, or nanosphere coated on its surfaces with drugs in the form of e.g., a drug-containing coating or film-forming composition using, for example, fluid bed techniques or other methodologies known to those of skill in the art. The inert particle can be of various sizes, so long as it is large enough to remain poorly dissolved. Alternatively, the active core may be prepared by granulating and milling and/or by extrusion and spheronization of a polymer composition containing the drug substance.

The active agents may be introduced to the inert carrier by techniques known to one skilled in the art, such as drug layering, powder coating, extrusion/spheronization, roller compaction or granulation. The amount of drug in the core will depend on the dose that is required, and typically varies from about 5 to 90 weight %. Generally, the polymeric coating on the active core will be from about 1 to 50% based on the weight of the coated particle, depending on the lag time required and/or the polymers and coating solvents chosen. Those skilled in the art will be able to select an appropriate amount of drug for coating onto or incorporating into the core to achieve the desired dosage. In one embodiment, the inactive core may be a sugar sphere or a buffer crystal or an encapsulated buffer crystal such as calcium carbonate, sodium bicarbonate, fumaric acid, tartaric acid, etc. which alters the microenvironment of the drug to facilitate its release.

Extended-release formulations may utilize a variety of extended-release coatings or mechanisms facilitating the gradual release of active agents over time. In some embodiments, the extended-release agent comprises a polymer controlling release by dissolution controlled release. In a particular embodiment, the active agent(s) are incorporated in a matrix comprising an insoluble polymer and drug particles or granules coated with polymeric materials of varying thickness. The polymeric material may comprise a lipid barrier comprising a waxy material, such as carnauba wax, beeswax, spermaceti wax, candellila wax, shallac wax, cocoa butter, cetostearyl alcohol, partially hydrogenated vegetable oils, ceresin, paraffin wax, ceresine, myristyl alcohol, stearyl alcohol, cetyl alcohol and stearic acid, along with surfactants, such as polyoxyethylene sorbitan monooleate. When contacted with an aqueous medium, such as biological fluids, the polymer coating emulsifies or erodes after a predetermined lag-time depending on the thickness of the polymer coating. The lag time is independent of gastrointestinal motility, pH, or gastric residence.

In other embodiments, the extended-release agent comprises a polymeric matrix effecting diffusion controlled release. The matrix may comprise one or more hydrophilic and/or water-swellable, matrix forming polymers, pH-dependent polymers, and/or pH-independent polymers.

In one embodiment, the extended-release formulation comprises a water soluble or water-swellable matrix-forming polymer, optionally containing one or more solubility-enhancing excipients and/or release-promoting agents. Upon solubilization of the water soluble polymer, the active agent(s) dissolve (if soluble) and gradually diffuse through the hydrated portion of the matrix. The gel layer grows with time as more water permeates into the core of the matrix, increasing the thickness of the gel layer and providing a diffusion barrier to drug release. As the outer layer becomes fully hydrated, the polymer chains become completely relaxed and can no longer maintain the integrity of the gel layer, leading to disentanglement and erosion of the outer hydrated polymer on the surface of the matrix. Water continues to penetrate towards the core through the gel layer, until it has been completely eroded. Whereas soluble drugs are released by this combination of diffusion and erosion mechanisms, erosion is the predominant mechanism for insoluble drugs, regardless of dose.

Similarly, water-swellable polymers typically hydrate and swell in biological fluids forming a homogenous matrix structure that maintains its shape during drug release and serves as a carrier for the drug, solubility enhancers and/or release promoters. The initial matrix polymer hydration phase results in slow-release of the drug (lag phase). Once the water swellable polymer is fully hydrated and swollen, water within the matrix can similarly dissolve the drug substance and allow for its diffusion out through the matrix coating.

Additionally, the porosity of the matrix can be increased due to the leaching out of pH-dependent release promoters so as to release the drug at a faster rate. The rate of the drug release then becomes constant and is a function of drug diffusion through the hydrated polymer gel. The release rate from the matrix is dependent upon various factors, including polymer type and level; drug solubility and dose; polymer:drug ratio; filler type and level; polymer to filler ratio; particle size of drug and polymer; and porosity and shape of the matrix.

Exemplary hydrophilic and/or water-swellable, matrix forming polymers include, but are not limited to, cellulosic polymers, including hydroxyalkyl celluloses and carboxyalkyl celluloses, such as hydroxypropylmethylcellulose (HPMC), hydroxypropylcellulose (HPC), hydroxyethylcellulose (HEC), methylcellulose (MC), carboxymethylcellulose (CMC), powdered cellulose such as microcrystalline cellulose, cellulose acetate, ethylcellulose, salts thereof, and combinations thereof; alginates, gums, including heteropolysaccharide gums and homopolysaccharide gums, such as xanthan, tragacanth, pectin, acacia, karaya, alginates, agar, guar, hydroxypropyl guar, veegum, carrageenan, locust bean gum, gellan gum, and derivatives thereofrom; acrylic resins, including polymers and copolymers of acrylic acid, methacrylic acid, methyl acrylate and methyl methacrylate and cross-linked polyacrylic acid derivatives such as Carbomers (e.g., CARBOPOL®, such as including CARBOPOL® 71G NF, available in various molecular weight grades from Noveon, Inc., Cincinnati, Ohio); carageenan; polyvinyl acetate (e.g., KOLLIDON® SR); polyvinyl pyrrolidone and its derivatives such as crospovidone; polyethylene oxides; and polyvinyl alcohol. Preferred hydrophilic and water-swellable polymers include the cellulosic polymers, especially HPMC.

The extended-release formulation may further comprise at least one binder that is capable of cross-linking the hydrophilic compound to form a hydrophilic polymer matrix (i.e., a gel matrix) in an aqueous medium, including biological fluids.

Exemplary binders include homopolysaccharides, such as galactomannan gums, guar gum, hydroxypropyl guar gum, hydroxypropylcellulose (HPC; e.g., Klucel EXF) and locust bean gum. In other embodiments, the binder is an alginic acid derivative, HPC or microcrystallized cellulose (MCC). Other binders include, but are not limited to, starches, microcrystalline cellulose, hydroxypropyl cellulose, hydroxyethyl cellulose, hydroxypropylmethyl cellulose and polyvinylpyrrolidone.

In one embodiment, the introduction method is drug layering by spraying a suspension of active agent(s) and a binder onto the inert carrier.

The binder may be present in the bead formulation in an amount of from about 0.1% to about 15% by weight, and preferably of from about 0.2% to about 10% by weight.

In some embodiments, the hydrophilic polymer matrix may further include an ionic polymer, a non-ionic polymer, or water-insoluble hydrophobic polymer to provide a stronger gel layer and/or reduce pore quantity and dimensions in the matrix so as to slow diffusion and erosion rates and concomitant release of the active agent(s). This may additionally suppress the initial burst effect and produce a more steady, "zero order release" of active agent(s).

Exemplary ionic polymers for slowing dissolution rate include both anionic and cationic polymers. Exemplary anionic polymers include, for example, sodium carboxymethylcellulose (Na CMC), sodium alginate, polymers of acrylic acid or carbomers (e.g., CARBOPOL® 934, 940, 974P NF); enteric polymers, such as polyvinyl acetate phthalate (PVAP), methacrylic acid copolymers (e.g., EUDRAGIT® L100, L 30D 55, A, and FS 30D), hypromellose acetate succinate (AQUAT HPMCAS); and xanthan gum. Exemplary cationic polymers include, for example, dimethylaminoethyl methacrylate copolymer (e.g., EUDRAGIT® E 100). Incorporation of anionic polymers, particularly enteric polymers, is useful for developing a pH-independent release profile for weakly basic drugs as compared to hydrophilic polymer alone.

Exemplary non-ionic polymers for slowing dissolution rate, include, for example, hydroxypropylcellulose (HPC) and polyethylene oxide (PEO) (e.g., POLYOX™)

Exemplary hydrophobic polymers include ethylcellulose (e.g., ETHOCEL™, SURELEASE®), cellulose acetate, methacrylic acid copolymers (e.g., EUDRAGIT® NE 30D), ammonio-methacrylate copolymers (e.g., EUDRAGIT® RL 100 or PO RS100), polyvinyl acetate, glyceryl monostearate, fatty acids, such as acetyl tributyl citrate, and combinations and derivatives thereof.

The swellable polymer can be incorporated in the formulation in proportion from 1% to 50% by weight, preferably from 5% to 40% by weight, most preferably from 5% to 20% by weight. The swellable polymers and binders may be incorporated in the formulation either prior to or after granulation. The polymers can also be dispersed in organic solvents or hydro-alcohols and sprayed during granulation.

Exemplary release-promoting agents include pH-dependent enteric polymers that remain intact at pH value lower than about 4.0 and dissolve at pH values higher than 4.0, preferably higher than 5.0, most preferably about 6.0, are considered useful as release-promoting agents for this invention. Exemplary pH-dependent polymers include, but are not limited to, methacrylic acid copolymers, methacrylic acid-methyl methacrylate copolymers (e.g., EUDRAGIT® L100 (Type A), EUDRAGIT® S100 (Type B), Rohm GmbH, Germany; methacrylic acid-ethyl acrylate copolymers (e.g., EUDRAGIT® L100-55 (Type C) and EUDRAGIT® L30D-55 copolymer dispersion, Rohm GmbH, Germany); copolymers of methacrylic acid-methyl methacrylate and methyl methacrylate (EUDRAGIT® FS); terpolymers of methacrylic acid, methacrylate, and ethyl acrylate; cellulose acetate phthalates (CAP); hydroxypropyl methylcellulose phthalate (HPMCP) (e.g., HP-55, HP-50, HP-55S, Shinetsu Chemical, Japan); polyvinyl acetate phthalates (PVAP) (e.g., COATERIC®, OPADRY® enteric white OY-P-7171); polyvinylbutyrate acetate; cellulose acetate succinates (CAS); hydroxypropyl methylcellulose acetate succinate (HPM-CAS), e.g., HPMCAS LF Grade, MF Grade, HF Grade, including AQOAT® LF and AQOAT® MF (Shin-Etsu Chemical, Japan); Shinetsu Chemical, Japan); shellac (e.g., MARCOAT™ 125 & MARCOAT™ 125N); vinyl acetate-maleic anhydride copolymer; styrene-maleic monoester copolymer; carboxymethyl ethylcellulose (CMEC, Freund Corporation, Japan); cellulose acetate phthalates (CAP) (e.g., AQUATERIC®); cellulose acetate trimellitates (CAT); and mixtures of two or more thereof at weight ratios between about 2:1 to about 5:1, such as, for instance, a mixture of EUDRAGIT® L 100-55 and EUDRAGIT® S 100 at a weight ratio of about 3:1 to about 2:1, or a mixture of EUDRAGIT® L 30 D-55 and EUDRAGIT® FS at a weight ratio of about 3:1 to about 5:1.

These polymers may be used either alone or in combination, or together with polymers other than those mentioned above. Preferred enteric pH-dependent polymers are the pharmaceutically acceptable methacrylic acid copolymers. These copolymers are anionic polymers based on methacrylic acid and methyl methacrylate and, preferably, have a mean molecular weight of about 135,000. A ratio of free carboxyl groups to methyl-esterified carboxyl groups in these copolymers may range, for example, from 1:1 to 1:3, e.g. around 1:1 or 1:2. Such polymers are sold under the trade name Eudragit® such as the Eudragit L series e.g., Eudragit L 12.5®, Eudragit L 12.5P®, Eudragit L100®, Eudragit L 100-55®, Eudragit L-30D®, Eudragit L-30 D-55®, the Eudragit S® series e.g., Eudragit S 12.5®, Eudragit S 12.5P®, Eudragit S100®. The release promoters are not limited to pH dependent polymers. Other hydrophilic molecules that dissolve rapidly and leach out of the dosage form quickly leaving a porous structure can be also be used for the same purpose.

The release-promoting agent can be incorporated in an amount from 10% to 90%, preferably from 20% to 80% and most preferably from 30% to 70% by weight of the dosage unit. The agent can be incorporated into the formulation either prior to or after granulation. The release-promoting agent can be added into the formulation either as a dry material, or it can be dispersed or dissolved in an appropriate solvent, and dispersed during granulation.

In some embodiments, the matrix may include a combination of release promoters and solubility enhancers. The solubility enhancers can be ionic and non-ionic surfactants, complexing agents, hydrophilic polymers, pH modifiers, such as acidifying agents and alkalinizing agents, as well as molecules that increase the solubility of poorly soluble drug through molecular entrapment. Several solubility enhancers can be utilized simultaneously.

Solubility enhancers may include surface active agents, such as sodium docusate, sodium lauryl sulfate, sodium stearyl fumarate, Tweens® and Spans® (PEO modified sorbitan monoesters and fatty acid sorbitan esters), poly(ethylene oxide)-polypropylene oxide-poly(ethylene oxide) block copolymers (aka PLURONICS™); complexing agents such as low molecular weight polyvinyl pyrrolidone and low molecular weight hydroxypropyl methyl cellulose; molecules that aid solubility by molecular entrapment such as cyclodextrins, and pH modifying agents, including acidifying agents such as citric acid, fumaric acid, tartaric acid, and hydrochloric acid; and alkalizing agents such as meglumine and sodium hydroxide.

Solubility enhancing agents typically constitute from 1% to 80% by weight, preferably from 1% to 60%, more preferably from 1% to 50%, of the dosage form and can be incorporated in a variety of ways. They can be incorporated in the formulation prior to granulation in dry or wet form. They can also be added to the formulation after the rest of the materials are granulated or otherwise processed. During granulation, solubilizers can be sprayed as solutions with or without a binder.

In some embodiments, the extended-release formulation comprises a polymeric matrix that can provide for release of the drug after a certain time, independent of the pH. For purposes of the present invention, "pH independent" is defined as having characteristics (e.g., dissolution) which are substantially unaffected by pH. pH independent polymers are often referred to in the context of "time-controlled" or "time-dependent" release profiles.

A pH independent polymer may be used to coat the active agent and/or provide a polymer for a hydrophilic matrix in the extended-release coating thereover. The pH independent polymer may be water-insoluble or water soluble. Exemplary water insoluble pH independent polymers include, but are not limited to, neutral methacrylic acid esters with a small portion of trimethylammonioethyl methacrylate chloride (e.g., EUDRAGIT® RS and EUDRAGIT® RL; neutral ester dispersions without any functional groups (e.g., EUDRAGIT® NE30D and EUDRAGIT® NE30); cellulosic polymers, such as ethylcellulose, hydroxyl ethyl cellulose, cellulose acetate or mixtures and other pH independent coating products. Exemplary water soluble pH independent polymers include hydroxyalkyl cellulose ethers, such as hydroxypropyl methylcellulose (HPMC), and hydroxypropyl cellulose (HPC); polyvinylpyrrolidone (PVP), methylcellulose, OPADRY® amb, guar gum, xanthan gum, gum arabic, hydroxyethyl cellulose and ethyl acrylate and methyl methacrylate copolymer dispersion or combinations thereof.

In one embodiment, the extended-release formulation comprises a water-insoluble water-permeable polymeric coating or matrix comprising one or more water-insoluble water-permeable film-forming over the active core. The coating may additionally include one or more water soluble polymers and/or one or more plasticizers. The water-insoluble polymer coating comprises a barrier coating for release of active agents in the core, wherein lower molecular weight (viscosity) grades exhibit faster release rates as compared to higher viscosity grades.

In preferred embodiments, the water-insoluble film-forming polymers include one or more alkyl cellulose ethers, such as ethyl celluloses and mixtures thereof, (e.g., ethyl cellulose grades PR100, PR45, PR20, PR10 and PR7; ETHOCEL®, Dow).

An exemplary water-soluble polymer such as polyvinylpyrrolidone (POVIDONE®), hydroxypropyl methylcellulose, hydroxypropyl cellulose and mixtures thereof.

In some embodiments, the water-insoluble polymer provides suitable properties (e.g., extended-release characteristics, mechanical properties, and coating properties) without the need for a plasticizer. For example, coatings comprising polyvinyl acetate (PVA), neutral copolymers of acrylate/ methacrylate esters such as commercially available Eudragit NE30D from Evonik Industries, ethyl cellulose in combination with hydroxypropylcellulose, waxes, etc. can be applied without plasticizers.

In yet another embodiment, the water-insoluble polymer matrix may further include a plasticizer. The amount of plasticizer required depends upon the plasticizer, the properties of the water-insoluble polymer, and the ultimate desired properties of the coating. Suitable levels of plasticizer range from about 1% to about 20%, from about 3% to about 20%, about 3% to about 5%, about 7% to about 10%, about 12% to about 15%, about 17% to about 20%, or about 1%, about 2%, about 3%, about 4%, about 5%, about 6%, about 7%, about 8%, about 9%, about 10%, about 15%, or about 20% by weight relative to the total weight of the coating, inclusive of all ranges and sub-ranges therebetween.

Exemplary plasticizers include, but are not limited to, triacetin, acetylated monoglyceride, oils (castor oil, hydrogenated castor oil, rape seed oil, sesame oil, olive oil, etc.); citrate esters, triethyl citrate, acetyltriethyl citrate acetyltributyl citrate, tributyl citrate, acetyl tri-n-butyl citrate, diethyl phthalate, dibutyl phthalate, dioctyl phthalate, methyl paraben, propyl paraben, propyl paraben, butyl paraben, diethyl sebacate, dibutyl sebacate, glyceroltributyrate, substituted triglycerides and glycerides, monoacetylated and diacetylated glycerides (e.g., MYVACET® 9-45), glyceryl monostearate, glycerol tributyrate, polysorbate 80, polyethyleneglycol (such as PEG-4000, PEG-400), propyleneglycol, 1,2-propyleneglycol, glycerin, sorbitol, diethyl oxalate, diethyl malate, diethyl fumarate, diethylmalonate, dibutyl succinate, fatty acids, glycerin, sorbitol, diethyl oxalate, diethyl malate, diethyl maleate, diethyl fumarate, diethyl succinate, diethyl malonate, dioctyl phthalate, dibutyl sebacate, and mixtures thereof. The plasticizer can have surfactant properties, such that it can act as a release modifier. For example, non-ionic detergents such at Brij 58 (polyoxyethylene (20) cetyl ether), and the like, can be used.

Plasticizers can be high boiling point organic solvents used to impart flexibility to otherwise hard or brittle polymeric materials and can affect the release profile for the active agent(s). Plasticizers generally cause a reduction in the cohesive intermolecular forces along the polymer chains resulting in various changes in polymer properties including a reduction in tensile strength, and increase in elongation and a reduction in the glass transition or softening temperature of the polymer. The amount and choice of the plasticizer can affect the hardness of a tablet, for example, and can even affect its dissolution or disintegration characteristics, as well as its physical and chemical stability. Certain plasticizers can increase the elasticity and/or pliability of a coat, thereby decreasing the coat's brittleness.

In another embodiment, the extended-release formulation comprises a combination of at least two gel-forming polymers, including at least one non-ionic gel-forming polymer and/or at least one anionic gel-forming polymer. The gel formed by the combination of gel-forming polymers provides controlled release, such that when the formulation is ingested and comes into contact with the gastrointestinal fluids, the polymers nearest the surface hydrate to form a viscous gel layer. Because of the high viscosity, the viscous layer dissolves away only gradually, exposing the material below to the same process. The mass thus dissolves away slowly, thereby slowly releasing the active ingredient into the gastrointestinal fluids. The combination of at least two gel-forming polymers enables properties of the resultant gel, such as viscosity, to be manipulated in order to provide the desired release profile.

In a particular embodiment, the formulation comprises at least one non-ionic gel-forming polymer and at least one anionic gel-forming polymer. In another embodiment, the formulation comprises two different non-ionic gel-forming polymers. In yet another embodiment, the formulation comprises a combination of non-ionic gel-forming polymers of the same chemistry, but having different solubilities, viscosities, and/or molecular weights (for example a combination of hydroxyproplyl methylcellulose of different viscosity grades, such as HPMC K100 and HPMC K15M or HPMC K100M).

Exemplary anionic gel forming polymers include, but are not limited to, sodium carboxymethylcellulose (Na CMC), carboxymethyl cellulose (CMC), anionic polysaccharides such as sodium alginate, alginic acid, pectin, polyglucuronic acid (poly-α- and -β-1,4-glucuronic acid), polygalacturonic acid (pectic acid), chondroitin sulfate, carrageenan, furcellaran, anionic gums such as xanthan gum, polymers of acrylic acid or carbomers (Carbopol® 934, 940, 974P NF), Carbopol® copolymers, a Pemulen® polymer, polycarbophil, and others.

Exemplary non-ionic gel-forming polymers include, but are not limited to, Povidone (PVP: polyvinyl pyrrolidone), polyvinyl alcohol, copolymer of PVP and polyvinyl acetate, HPC (hydroxypropyl cellulose), HPMC (hydroxypropyl methylcellulose), hydroxyethyl cellulose, hydroxymethyl cellulose, gelatin, polyethylene oxide, acacia, dextrin, starch, polyhydroxyethylmethacrylate (PHEMA), water soluble nonionic polymethacrylates and their copolymers, modified cellulose, modified polysaccharides, nonionic gums, nonionic polysaccharides and/or mixtures thereof.

The formulation may optionally comprise an enteric polymer as described above, and/or at least one excipient, such as a filler, a binder (as described above), a disintegrant, and/or a flow aid or glidant.

Exemplary fillers include but are not limited to, lactose, glucose, fructose, sucrose, dicalcium phosphate, sugar alcohols also known as "sugar polyol" such as sorbitol, manitol, lactitol, xylitol, isomalt, erythritol, and hydrogenated starch hydrolysates (a blend of several sugar alcohols), corn starch, potato starch, sodium carboxymethycellulose, ethylcellulose and cellulose acetate, enteric polymers, or a mixture thereof.

Exemplary binders, include but are not limited to, water-soluble hydrophilic polymers, such as Povidone (PVP: polyvinyl pyrrolidone), copovidone (a copolymer of polyvinyl pyrrolidone and polyvinyl acetate), low molecular weight HPC (hydroxypropyl cellulose) low molecular weight HPMC (hydroxypropyl methylcellulose), low molecular weight carboxy methyl cellulose, ethylcellulose, gelatin, polyethylene oxide, acacia, dextrin, magnesium aluminum silicate, starch, and polymethacrylates such as Eudragit NE 30D, Eudragit RL, Eudragit RS, Eudragit E, polyvinyl acetate, and enteric polymers, or mixtures thereof.

Exemplary disintegrants include but are not limited to low-substituted carboxymethyl cellulose sodium, crospovidone (cross-linked polyvinyl pyrrolidone), sodium carboxymethyl starch (sodium starch glycolate), cross-linked sodium carboxymethyl cellulose (Croscarmellose), pregelatinized starch (starch 1500), microcrystalline cellulose, water insoluble starch, calcium carboxymethyl cellulose, low substituted hydroxypropyl cellulose, and magnesium or aluminum silicate.

Exemplary glidants include but are not limited to, magnesium, silicon dioxide, talc, starch, titanium dioxide, and the like.

In yet another embodiment, the extended-release formulation is formed by coating a water soluble/dispersible drug-containing particle, such as a bead or bead population therein (as described above), with a coating material, and, optionally, a pore former and other excipients. The coating material is preferably selected from a group comprising cellulosic polymers, such as ethylcellulose (e.g., SURELEASE®), methylcellulose, hydroxypropyl cellulose, hydroxypropylmethyl cellulose, cellulose acetate, and cellulose acetate phthalate; polyvinyl alcohol; acrylic polymers such as polyacrylates, polymethacrylates and copolymers thereof, and other water-based or solvent-based coating materials. The release-controlling coating for a given bead population may be controlled by at least one parameter of the release controlling coating, such as the nature of the coating, coating level, type and concentration of a pore former, process parameters and combinations thereof. Thus, changing a parameter, such as a pore former concentration, or the conditions of the curing, allows for changes in the release of active agent(s) from any given bead population, thereby allowing for selective adjustment of the formulation to a pre-determined release profile.

Pore formers suitable for use in the release controlling coating herein can be organic or inorganic agents, and include materials that can be dissolved, extracted or leached from the coating in the environment of use. Exemplary pore forming agents include, but are not limited to, organic compounds such as mono-, oligo-, and polysaccharides including sucrose, glucose, fructose, mannitol, mannose, galactose, sorbitol, pullulan, dextran; polymers soluble in the environment of use such as water-soluble hydrophilic polymers, hydroxyalkylcelluloses, carboxyalkylcelluloses, hydroxypropylmethylcellulose, cellulose ethers, acrylic resins, polyvinylpyrrolidone, cross-linked polyvinylpyrrolidone, polyethylene oxide, Carbowaxes, Carbopol, and the like, diols, polyols, polyhydric alcohols, polyalkylene glycols, polyethylene glycols, polypropylene glycols, or block polymers thereof, polyglycols, poly($\alpha$-$\Omega$)alkylenediols; inorganic compounds such as alkali metal salts, lithium carbonate, sodium chloride, sodium bromide, potassium chloride, potassium sulfate, potassium phosphate, sodium acetate, sodium citrate, suitable calcium salts, combination thereof, and the like.

The release controlling coating can further comprise other additives known in the art, such as plasticizers, anti-adherents, glidants (or flow aids), and antifoams.

In some embodiments, the coated particles or beads may additionally include an "overcoat," to provide, e.g., moisture protection, static charge reduction, taste-masking, flavoring, coloring, and/or polish or other cosmetic appeal to the beads. Suitable coating materials for such an overcoat are known in the art, and include, but are not limited to, cellulosic polymers such as hydroxypropylmethylcellulose, hydroxypropylcellulose and microcrystalline cellulose, or combinations thereof (for example, various OPADRY® coating materials).

The coated particles or beads may additionally contain enhancers that may be exemplified by, but not limited to, solubility enhancers, dissolution enhancers, absorption enhancers, permeability enhancers, stabilizers, complexing agents, enzyme inhibitors, p-glycoprotein inhibitors, and multidrug resistance protein inhibitors. Alternatively, the formulation can also contain enhancers that are separated from the coated particles, for example in a separate population of beads or as a powder. In yet another embodiment, the enhancer(s) may be contained in a separate layer on coated particles either under or above the release controlling coating.

In other embodiments, the extended-release formulation is formulated to release the active agent(s) by an osmotic mechanism. By way of example, a capsule may be formulated with a single osmotic unit or it may incorporate 2, 3, 4, 5, or 6 push-pull units encapsulated within a hard gelatin capsule, whereby each bilayer push pull unit contains an osmotic push layer and a drug layer, both surrounded by a semi-permeable membrane. One or more orifices are drilled through the membrane next to the drug layer. This membrane may be additionally covered with a pH-dependent enteric coating to prevent release until after gastric emptying. The gelatin capsule dissolves immediately after ingestion. As the push pull unit(s) enter the small intestine, the enteric coating breaks down, which then allows fluid to flow through the semi-permeable membrane, swelling the osmotic push compartment to force to force drugs out through the orifice(s) at a rate precisely controlled by the rate of water transport through the semi-permeable membrane. Release of drugs can occur over a constant rate for up to 24 hours or more.

The osmotic push layer comprises one or more osmotic agents creating the driving force for transport of water through the semi-permeable membrane into the core of the delivery vehicle. One class of osmotic agents includes water-swellable hydrophilic polymers, also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly(acrylic) acid, poly (methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

Another class of osmotic agents includes osmogens, which are capable of imbibing water to effect an osmotic pressure gradient across the semi-permeable membrane. Exemplary osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking.

In some embodiments, the extended-release formulation may comprise a polysaccharide coating that is resistant to erosion in both the stomach and intestine. Such polymers can be only degraded in the colon, which contains a large microflora containing biodegradable enzymes breaking down, for example, the polysaccharide coatings to release the drug contents in a controlled, time-dependent manner. Exemplary polysaccharide coatings may include, for example, amylose, arabinogalactan, chitosan, chondroitin sulfate, cyclodextrin, dextran, guar gum, pectin, xylan, and combinations or derivatives therefrom.

In some embodiments, the pharmaceutical composition of the present application is formulated for delayed extended-release. As used herein, the term "delayed-release" refers to a medication that does not immediately disintegrate and release the active ingredient(s) into the body. In some embodiments, the term "delayed extended-release" is used with reference to a drug formulation having a release profile in which there is a predetermined delay in the release of the drug following administration. In some embodiments, the delayed extended-release formulation includes an extended-release formulation coated with an enteric coating, which is a barrier applied to oral medication that prevents release of medication before it reaches the small intestine. Delayed-release formulations, such as enteric coatings, prevent drugs having an irritant effect on the stomach, such as aspirin, from dissolving in the stomach. Such coatings are also used to protect acid-unstable drugs from the stomach's acidic exposure, delivering them instead to a basic pH environment (intestine's pH 5.5 and above) where they do not degrade, and give their desired action. Accordingly, a formulation that releases it component "after gastric emptying" refers to a delayed formulation that releases the active ingredient(s) after the formulation is emptied from the stomach.

The term "pulsatile release" is a type of delayed-release, which is used herein with reference to a drug formulation that provides rapid and transient release of the drug within a short time period immediately after a predetermined lag period, thereby producing a "pulsed" plasma profile of the drug after drug administration. Formulations may be designed to provide a single pulsatile release or multiple pulsatile releases at predetermined time intervals following administration, or a pulsatile release (e.g., 20-60% of the active ingredient) followed with extended release over a period of time (e.g., a continuous release of the remainder of the active ingredient).

A delayed-release or pulsatile release formulation generally comprises one or more elements covered with a barrier coating, which dissolves, erodes or ruptures following a specified lag phase. In some embodiments, the pharmaceutical composition of the present application is formulated for extended-release or delayed extended-release and comprises 100% of the total dosage of a given active agent administered in a single unit dose. In other embodiments, the pharmaceutical composition comprises an extended/delayed-release component and an immediate-release component. In some embodiments, the immediate-release component and the extended/delayed-release component contain the same active ingredient. In other embodiments, the immediate-release component and the extended/delayed-release component contain different active ingredients (e.g., an analgesic in one component and an α-blocker in another component). In some embodiments, the first and second components each comprises an α-blocker and an analgesic selected from the group consisting of aspirin, ibuprofen, naproxen sodium, indomethacin, nabumetone, and acetaminophen. In other embodiments, the first and second components each comprises a 5α-reductase inhibitor selected from the group consisting of finasteride, bexlosteride, epristeride, izonsteride, lapisteride and turosteride, and an analgesic selected from the group consisting of aspirin, ibuprofen, naproxen sodium, indomethacin, nabumetone, and acetaminophen. In other embodiments, the extended/delayed-release component is coated with an enteric coating. In other embodiments, the immediate-release component and/or the extended/delayed-release component further comprises an antimuscarinic agent selected from the group consisting of oxybutynin, solifenacin, darifenacin and atropine. In other embodiments, the immediate-release component and/or the extended/delayed-release component further comprises an antidiuretic agent, an antimuscarinic agent or both. In other embodiments, the treatment method includes administering to a subject a diuretic at least 8 or 7 hours prior to a target time, such as bedtime, and administering to the subject the pharmaceutical composition comprising the immediate-release component and/or the extended/delayed-release component within 2 hours prior to the target time.

In other embodiments, the "immediate-release" component provide about 5-50% of the total dosage of the active agent(s) and the "extended-release" component provides 50-95% of the total dosage of the active agent(s) to be delivered by the pharmaceutical formulation. For example, the immediate-release component may provide about 20-60%, or about 20%, 25%, 30%, 35%, 40%, 45%, 50%, 55%, 60% of the total dosage of the active agent(s) to be delivered by the pharmaceutical formulation. The extended-release component provides about 40%, 45%, 50%, 55%, 60%, 65%, 70%, 75% or 80% of the total dosage of the active agent(s) to be delivered by the formulation. In some embodiments, the extended-release component further comprises a barrier coating to delay the release of the active agent.

A barrier coating for delayed-release may consist of a variety of different materials, depending on the objective. In addition, a formulation may comprise a plurality of barrier coatings to facilitate release in a temporal manner. The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or a coating based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, the formulation may additionally include a time delay material such as, for example, glyceryl monostearate or glyceryl distearate.

In some embodiments, the delayed, extended-release formulation includes an enteric coating comprised one or more polymers facilitating release of active agents in proximal or distal regions of the gastrointestinal tract. As used herein, the term "enteric polymer coating" is a coating comprising of one or more polymers having a pH dependent or pH-independent release profile. Typically the coating resists dissolution in the acidic medium of the stomach, but dissolves or erodes in more distal regions of the gastrointestinal tract, such as the small intestine or colon. An enteric polymer coating typically resists releases of the active agents until sometime after a gastric emptying lag period of about 3-4 hours after administration.

pH dependent enteric coatings comprises one or more pH-dependent or pH-sensitive polymers that maintain their structural integrity at low pH, as in the stomach, but dissolve in higher pH environments in more distal regions of the gastrointestinal tract, such as the small intestine, where the drug contents are released. For purposes of the present invention, "pH dependent" is defined as having characteristics (e.g., dissolution) which vary according to environmental pH. Exemplary pH-dependent polymers include, but are not limited to, methacarylic acid copolymers, methacrylic acid-methyl methacrylate copolymers (e.g., EUDRAGIT® L100 (Type A), EUDRAGIT® S100 (Type B), Rohm GmbH, Germany; methacrylic acid-ethyl acrylate copolymers (e.g., EUDRAGIT® L100-55 (Type C) and EUDRAGIT® L30D-55 copolymer dispersion, Rohm GmbH, Germany); copolymers of methacrylic acid-methyl methacrylate and methyl methacrylate (EUDRAGIT® FS); terpolymers of methacrylic acid, methacrylate, and ethyl acrylate; cellulose acetate phthalates (CAP); hydroxypropyl methylcellulose phthalate (HPMCP) (e.g., HP-55, HP-50, HP-55S, Shinetsu Chemical, Japan); polyvinyl acetate phthalates (PVAP) (e.g., COATERIC®, OPADRY® enteric white OY-P-7171); cellulose acetate succinates (CAS); hydroxypropyl methylcellulose acetate succinate (HPM-CAS), e.g., HPMCAS LF Grade, MF Grade, HF Grade, including AQOAT® LF and AQOAT® MF (Shin-Etsu Chemical, Japan); Shinetsu Chemical, Japan); shellac (e.g., Marcoat™ 125 & Marcoat™ 125N); carboxymethyl ethylcellulose (CMEC, Freund Corporation, Japan), cellulose acetate phthalates (CAP) (e.g., AQUATERIC®); cellulose acetate trimellitates (CAT); and mixtures of two or more thereof at weight ratios between about 2:1 to about 5:1, such as, for instance, a mixture of EUDRAGIT® L 100-55 and EUDRAGIT® S 100 at a weight ratio of about 3:1 to about 2:1, or a mixture of EUDRAGIT® L 30 D-55 and EUDRAGIT® FS at a weight ratio of about 3:1 to about 5:1.

pH-dependent polymers typically exhibit a characteristic pH optimum for dissolution. In some embodiments, the pH-dependent polymer exhibits a pH optimum between about 5.0 and 5.5, between about 5.5 and 6.0, between about 6.0 and 6.5, or between about 6.5 and 7.0. In other embodiments, the pH-dependent polymer exhibits a pH optimum of $\geq 5.0$, of $\geq 5.5$, of $\geq 6.0$, of $\geq 6.5$, or of $\geq 7.0$.

In certain embodiment, the coating methodology employs the blending of one or more pH-dependent and one or more pH-independent polymers. The blending of pH-dependent and pH-independent polymers can reduce the release rate of active ingredients once the soluble polymer has reached its optimum pH of solubilization.

In some embodiments, a "time-controlled" or "time-dependent" release profile can be obtained using a water insoluble capsule body containing one or more active agents, wherein the capsule body closed at one end with an insoluble, but permeable and swellable hydrogel plug. Upon contact with gastrointestinal fluid or dissolution medium, the plug swells, pushing itself out of the capsule and releasing the drugs after a pre-determined lag time, which can be controlled by e.g., the position and dimensions of the plug. The capsule body may be further coated with an outer pH-dependent enteric coating keeping the capsule intact until it reaches the small intestine. Suitable plug materials include, for example, polymethacrylates, erodible compressed polymers (e.g., HPMC, polyvinyl alcohol), congealed melted polymer (e.g., glyceryl mono oleate) and enzymatically controlled erodible polymers (e.g., polysaccharides, such as amylose, arabinogalactan, chitosan, chondroitin sulfate, cyclodextrin, dextran, guar gum, pectin and xylan).

In other embodiments, capsules or bilayered tablets may be formulated to contain a drug-containing core, covered by a swelling layer, and an outer insoluble, but semi-permeable polymer coating or membrane. The lag time prior to rupture can be controlled by the permeation and mechanical properties of the polymer coating and the swelling behavior of the swelling layer. Typically, the swelling layer comprises one or more swelling agents, such as swellable hydrophilic polymers that swell and retain water in their structures.

Exemplary water swellable materials to be used in the delayed-release coating include, but are not limited to, polyethylene oxide (having e.g., an average molecular weight between 1,000,000 to 7,000,000, such as POLYOX®), methylcellulose, hydroxypropyl cellulose, hydroxypropyl methylcellulose; polyalkylene oxides having a weight average molecular weight of 100,000 to 6,000,000, including but not limited to poly(methylene oxide), poly (butylene oxide); poly(hydroxy alkyl methacrylate) having a molecular weight of from 25,000 to 5,000,000; poly(vinyl) alcohol, having a low acetal residue, which is cross-linked with glyoxal, formaldehyde or glutaraldehyde and having a degree of polymerization of from 200 to 30,000; mixtures of methyl cellulose, cross-linked agar and carboxymethyl cellulose; hydrogel forming copolymers produced by forming a dispersion of a finely divided copolymer of maleic anhydride with styrene, ethylene, propylene, butylene or isobutylene cross-linked with from 0.001 to 0.5 moles of saturated cross-linking agent per mole of maleic anyhydride in the copolymer; CARBOPOL® acidic carboxy polymers having a molecular weight of 450,000 to 4,000,000; CYANAMER® polyacrylamides; cross-linked water swellable indenemaleicanhydride polymers; GOODRITE® polyacrylic acid having a molecular weight of 80,000 to 200,000; starch graft copolymers; AQUA-KEEPS® acrylate polymer polysaccharides composed of condensed glucose units such as diester cross-linked polyglucan; carbomers having a viscosity of 3,000 to 60,000 mPa as a 0.5%-1% w/v aqueous solution; cellulose ethers such as hydroxypropylcellulose having a viscosity of about 1000-7000 mPa s as a 1% w/w aqueous solution (25° C.); hydroxypropyl methylcellulose having a viscosity of about 1000 or higher, preferably 2,500 or higher to a maximum of 25,000 mPa as a 2% w/v aqueous solution; polyvinylpyrrolidone having a viscosity of about 300-700 mPa s as a 10% w/v aqueous solution at 20° C.; and combinations thereof.

Alternatively, the release time of the drugs can be controlled by a disintegration lag time depending on the balance between the tolerability and thickness of a water insoluble polymer membrane (such as ethyl cellulose, EC) containing predefined micropores at the bottom of the body and the amount of a swellable excipient, such as low substituted hydroxypropyl cellulose (L-HPC) and sodium glycolate. After oral administration, GI fluids permeate through the micropores, causing swelling of the swellable excipients, which produces an inner pressure disengaging the capsular components, including a first capsule body containing the swellable materials, a second capsule body containing the drugs, and an outer cap attached to the first capsule body.

The enteric layer may further comprise anti-tackiness agents, such as talc or glyceryl monostearate and/or plasticizers. The enteric layer may further comprise one or more plasticizers including, but not limited to, triethyl citrate, acetyl triethyl citrate, acetyltributyl citrate, polyethylene glycol acetylated monoglycerides, glycerin, triacetin, propylene glycol, phthalate esters (e.g., diethyl phthalate, dibutyl phthalate), titanium dioxide, ferric oxides, castor oil, sorbitol and dibutyl sebacate.

In another embodiment, the delayed release formulation employs a water-permeable but insoluble film coating to enclose the active ingredient and an osmotic agent. As water from the gut slowly diffuses through the film into the core, the core swells until the film bursts, thereby releasing the active ingredients. The film coating may be adjusted to permit various rates of water permeation or release time.

In another embodiment, the delayed release formulation employs a water-impermeable tablet coating whereby water enters through a controlled aperture in the coating until the core bursts. When the tablet bursts, the drug contents are released immediately or over a longer period of time. These and other techniques may be modified to allow for a pre-determined lag period before release of drugs is initiated.

In another embodiment, the active agents are delivered in a formulation to provide both delayed-release and extended-release (delayed-sustained). The term "delayed-extended-release" is used herein with reference to a drug formulation providing pulsatile release of active agents at a pre-determined time or lag period following administration, which is then followed by extended-release of the active agents thereafter.

In some embodiments, immediate-release, extended-release, delayed-release, or delayed-extended-release formulations comprises an active core comprised of one or more inert particles, each in the form of a bead, pellet, pill, granular particle, microcapsule, microsphere, microgranule, nanocapsule, or nanosphere coated on its surfaces with drugs in the form of e.g., a drug-containing film-forming composition using, for example, fluid bed techniques or other methodologies known to those of skill in the art. The inert particle can be of various sizes, so long as it is large enough to remain poorly dissolved. Alternatively, the active core may be prepared by granulating and milling and/or by extrusion and spheronization of a polymer composition containing the drug substance.

The amount of drug in the core will depend on the dose that is required, and typically varies from about 5 to 90 weight %. Generally, the polymeric coating on the active core will be from about 1 to 50% based on the weight of the coated particle, depending on the lag time and type of release profile required and/or the polymers and coating solvents chosen. Those skilled in the art will be able to select an appropriate amount of drug for coating onto or incorporating into the core to achieve the desired dosage. In one embodiment, the inactive core may be a sugar sphere, or a buffer crystal or an encapsulated buffer crystal such as calcium carbonate, sodium bicarbonate, fumaric acid, tartaric acid, etc. which alters the microenvironment of the drug to facilitate its release.

In some embodiments, for example, delayed-release or delayed-extended-release compositions may formed by coating a water soluble/dispersible drug-containing particle, such as a bead, with a mixture of a water insoluble polymer and an enteric polymer, wherein the water insoluble polymer and the enteric polymer may be present at a weight ratio of from 4:1 to 1:1, and the total weight of the coatings is 10 to 60 weight % based on the total weight of the coated beads. The drug layered beads may optionally include an inner dissolution rate controlling membrane of ethylcellulose. The composition of the outer layer, as well as the individual weights of the inner and outer layers of the polymeric membrane are optimized for achieving desired circadian rhythm release profiles for a given active, which are predicted based on in vitro/in vivo correlations.

In other embodiments the formulations may comprise a mixture of immediate-release drug-containing particles without a dissolution rate controlling polymer membrane and delayed-extended-release beads exhibiting, for example, a lag time of 2-4 hours following oral administration, thus providing a two-pulse release profile.

In some embodiments, the active core is coated with one or more layers of dissolution rate-controlling polymers to obtain desired release profiles with or without a lag time. An inner layer membrane can largely control the rate of drug release following imbibition of water or body fluids into the core, while the outer layer membrane can provide for a desired lag time (the period of no or little drug release following imbibition of water or body fluids into the core). The inner layer membrane may comprise a water insoluble polymer, or a mixture of water insoluble and water soluble polymers.

The polymers suitable for the outer membrane, which largely controls the lag time of up to 6 hours, may comprise an enteric polymer, as described above, and a water insoluble polymer at 10 to 50 weight %. The ratio of water insoluble polymer to enteric polymer may vary from 4:1 to 1:2, preferably the polymers are present at a ratio of about 1:1. The water insoluble polymer typically used is ethylcellulose.

Exemplary water insoluble polymers include ethylcellulose, polyvinyl acetate (Kollicoat SR #0D from BASF), neutral copolymers based on ethyl acrylate and methylmethacrylate, copolymers of acrylic and methacrylic acid esters with quaternary ammonium groups such as EUDRAGIT® NE, RS and RS30D, RL or RL30D and the like. Exemplary water soluble polymers include low molecular weight HPMC, HPC, methylcellulose, polyethylene glycol (PEG of molecular weight>3000) at a thickness ranging from 1 weight % up to 10 weight % depending on the solubility of the active in water and the solvent or latex suspension based coating formulation used. The water insoluble polymer to water soluble polymer may typically vary from 95:5 to 60:40, preferably from 80:20 to 65:35.

In some embodiments, AMBERLITE™ IRP69 resin is used as an extended-release carrier. AMBERLITE™ IRP69 is an insoluble, strongly acidic, sodium form cation exchange resin that is suitable as carrier for cationic (basic) substances. In other embodiments, DUOLITE™ AP143/1093 resin is used as an extended-release carrier. DUOLITE™ AP143/1093 is an insoluble, strongly basic, anion exchange resin that is suitable as a carrier for anionic (acidic) substances.

When used as a drug carrier, AMBERLITE IRP69 or/and DUOLITE™ AP143/1093 resin provides a means for binding medicinal agents onto an insoluble polymeric matrix. Extended-release is achieved through the formation of resin-drug complexes (drug resinates). The drug is released from the resin in vivo as the drug reaches equilibrium with the high electrolyte concentrations, which are typical of the gastrointestinal tract. More hydrophobic drugs will usually elute from the resin at a lower rate, owing to hydrophobic interactions with the aromatic structure of the cation exchange system.

Most enteric coatings work by presenting a surface that is stable at the highly acidic pH found in the stomach, but breaks down rapidly at a less acidic (relatively more basic) pH. Therefore, an enteric coated pill will not dissolve in the acidic juices of the stomach (pH ~3), but they will in the alkaline (pH 7-9) environment present in the small intestine. Examples of enteric coating materials include, but are not limited to, methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate and stearic acid. In some embodiments, the pharmaceutical composition is formulated for oral administration. Oral dosage forms include, for example, tablets, capsules, caplets, and may also comprise a plurality of granules, beads, powders or pellets that may or may not be encapsulated. Tablets and capsules represent the most convenient oral dosage forms, in which case solid pharmaceutical carriers are employed.

In a delayed-release formulation, one or more barrier coatings may be applied to pellets, tablets, or capsules to facilitate slow dissolution and concomitant release of drugs into the intestine. Typically, the barrier coating contains one or more polymers encasing, surrounding, or forming a layer, or membrane around the therapeutic composition or active core.

In some embodiments, the active agents are delivered in a formulation to provide delayed-release at a pre-determined time following administration. The delay may be up to about 10 minutes, about 20 minutes, about 30 minutes, about 1 hour, about 2 hours, about 3 hours, about 4 hours, about 5 hours, about 6 hours, or longer.

Various coating techniques may be applied to granules, beads, powders or pellets, tablets, capsules or combinations thereof containing active agents to produce different and distinct release profiles. In some embodiments, the pharmaceutical composition is in a tablet or capsule form containing a single coating layer. In other embodiments, the pharmaceutical composition is in a tablet or capsule form containing multiple coating layers.

In some embodiments, the pharmaceutical composition comprises one or more analgesics, one or more α-blockers, and one or more other active ingredients selected from the group consisting of antimuscarinic agents, antidiuretics and spasmolytics. In some embodiments, the pharmaceutical composition comprises one or more analgesics, one or more 5α-reductase inhibitors, and one or more other active ingredients selected from the group consisting of antimuscarinic agents, antidiuretics, α-blockers and spasmolytics. Examples of antimuscarinic agents include, but are not limited to, oxybutynin, solifenacin, darifenacin and atropine. Examples of antidiuretics include, but are not limited to, antidiuretic hormone (ADH), angiotensin II, aldosterone, vasopressin, vasopressin analogs (e.g., desmopressin argipressin, lypressin, felypressin, ornipressin, terlipressin; vasopressin receptor agonists, atrial natriuretic peptide (ANP) and C-type natriuretic peptide (CNP) receptor (i.e., NPR1, NPR2, NPR3) antagonists (e.g., HS-142-1, isatin, [Asu7,23']b-ANP-(7-28)], anantin, a cyclic peptide from Streptomyces coerulescens, and 3G12 monoclonal antibody); somatostatin type 2 receptor antagonists (e.g., somatostatin), and pharmaceutically-acceptable derivatives, analogs, salts, hydrates, and solvates thereof. Examples of spasmolytics include, but are not limited to, carisoprodol, benzodiazepines, baclofen, cyclobenzaprine, metaxalone, methocarbamol, clonidine, clonidine analog, and dantrolene.

In some embodiments, the pharmaceutical composition comprises one or more analgesics and one or more α-blockers. In another embodiment, the pharmaceutical composition comprises (1) one or more analgesics, (2) one or more α-blockers, and (3) one or more antimuscarinic agents. In another embodiment, the pharmaceutical composition comprises (1) one or more analgesics, (2) one or more α-blockers and (3) one or more antidiuretics. In another embodiment, the pharmaceutical composition comprises (1) one or more analgesics, (2) one or more α-blockers, and (3) one or more spasmolytics. In another embodiment, the pharmaceutical composition comprises (1) one or two analgesics, (2) one or more α-blockers, (3) one or two antimuscarinic agents, and (4) one or two antidiuretics. In another embodiment, the pharmaceutical composition comprises (1) one or more analgesics, (2) one or more α-blockers, (3) one or more spasmolytics agents, and (4) one or more antidiuretics.

In some embodiments, the pharmaceutical composition comprises one or more analgesics and one or more 5α-reductase inhibitors. In another embodiment, the pharmaceutical composition comprises (1) one or more analgesics, (2) one or more 5α-reductase inhibitors, and (3) one or more antimuscarinic agents. In another embodiment, the pharmaceutical composition comprises (1) one or more analgesics, (2) one or more 5α-reductase inhibitors and (3) one or more antidiuretics. In another embodiment, the pharmaceutical composition comprises (1) one or more analgesics, (2) one or more 5α-reductase inhibitors, and (3) one or more spasmolytics. In another embodiment, the pharmaceutical composition comprises (1) one or two analgesics, (2) one or more 5α-reductase inhibitors, (3) one or two antimuscarinic agents, and (4) one or two antidiuretics. In another embodiment, the pharmaceutical composition comprises (1) one or more analgesics, (2) one or more 5α-reductase inhibitors, (3) one or more spasmolytics agents, and (4) one or more antidiuretics.

In another embodiment, the pharmaceutical composition comprises (1) one or more analgesics, (2) one or more 5α-reductase inhibitors, and (3) one or more α-blockers. In another embodiment, the pharmaceutical composition comprises (1) one or more analgesics, (2) one or more 5α-reductase inhibitors, (3) one or more α-blockers and (4) one or more antidiuretics. In another embodiment, the pharmaceutical composition comprises (1) one or more analgesics, (2) one or more 5α-reductase inhibitors, (3) one or more α-blockers and (4) one or more spasmolytics. In another embodiment, the pharmaceutical composition comprises (1) one or two analgesics, (2) one or more 5α-reductase inhibitors, (3) one or two antimuscarinic agents, (4) one or two antidiuretics and (5) one or more α-blockers. In another embodiment, the pharmaceutical composition comprises (1) one or more analgesics, (2) one or more 5α-reductase inhibitors, (3) one or more spasmolytics agents, (4) one or more antidiuretics, and (5) one or more α-blockers.

In one embodiment, the plurality of active ingredients are formulated for immediate-release. In other embodiment, the plurality of active ingredients are formulated for extended-release. In other embodiment, the plurality of active ingredients are formulated for both immediate-release and extended-release (e.g., a first portion of each active ingredient is formulated for immediate-release and a second portion of each active ingredient is formulated for extended-release). In yet other embodiment, some of the plurality of active ingredients are formulated for immediate-release and some of the plurality of active ingredients are formulated for extended-release (e.g., active ingredients A, B, C are formulated for immediate-release and active ingredients C and D are formulated for extended-release). In some other embodiments, the immediate-release component and/or the extended-release component is further coated with a delayed-release coating, such as an enteric coating.

In certain embodiments, the pharmaceutical composition comprises an immediate-release component and an extended-release component. The immediate-release component may comprise one or more active ingredients selected from the group consisting of analgesics, α-blockers, 5α-reductase inhibitors, antimuscarinic agents, antidiuretics and spasmolytics. The extended-release component may comprise one or more active ingredients selected from the group consisting of analgesics, α-blockers, antimuscarinic agents, antidiuretics and spasmolytics. In some embodiments, the immediate-release component and the extended-release component have exactly the same active ingredients. In other embodiments, the immediate-release component and the extended-release component have different active ingredients. In yet other embodiments, the immediate-release component and the extended-release component have one or more common active ingredients. In some other embodiments, the immediate-release component and/or the extended-release component is further coated with a delayed-release coating, such as an enteric coating.

In one embodiment, the pharmaceutical composition comprises two or more active ingredients (e.g., a mixture of one or more analgesic agents, and one or more α-blockers, one or more 5α-reductase inhibitors, one or more antimuscarinic agents or antidiuretics or spasmolytics), formulated for immediate-release at about the same time. In another embodiment, the pharmaceutical composition comprises two or more active ingredients, formulated for extended-release at about the same time. In another embodiment, the pharmaceutical composition comprises two or more active ingredients formulated as two extended-release components, each providing a different extended-release profile. For example, a first extended-release component releases a first active ingredient at a first release rate and a second extended-release component releases a second active ingredient at a second release rate. In another embodiment, the pharmaceutical composition comprises two or more active ingredients, both formulated for delayed release. In another embodiment, the pharmaceutical composition comprises two or more active ingredients formulated for delayed release. In another embodiment, the pharmaceutical composition comprises two or more active ingredients formulated as two delayed-release components, each providing a different delayed-release profile. For example, a first delayed-release component releases a first active ingredient at a first time point and a second delayed-release component releases a second active ingredient at a second time point. In another embodiment, the pharmaceutical composition comprises two or more active ingredients, one or more of which are formulated for immediate-release and the others are formulated for extended-release. In another embodiment, the pharmaceutical composition comprises two or more active ingredients, a fraction of which is formulated for immediate-release and the remainder is formulated for extended-release.

In some embodiments, the pharmaceutical composition comprises one or more analgesic agents, and one or more α-blockers, 5α-reductase inhibitors, an antidiuretic, wherein the one or more analgesic agents and one or more α-blockers are formulated for delayed release and wherein the antidiuretic is formulated for immediate release. In other embodiments, the pharmaceutical composition further comprises an additional agent selected from the group consisting of an analgesic agent, α-blocker, a 5α-reductase inhibitor, an antimuscarinic agent, an antidiuretic agent and a spasmolytic, wherein the additional agent is formulated for delayed release. In some embodiments, the delayed release formulation delays the release of the active ingredient for a period of 1, 2, 3, 4 or 5 hours.

The term "immediate-release" is used herein with reference to a drug formulation that does not contain a dissolution rate controlling material. There is substantially no delay in the release of the active agents following administration of an immediate-release formulation. An immediate-release coating may include suitable materials immediately dissolving following administration so as to release the drug contents therein. Exemplary immediate-release coating materials include gelatin, polyvinyl alcohol polyethylene glycol (PVA-PEG) copolymers (e.g., KOLLICOAT®) and various others materials known to those skilled in the art.

An immediate-release composition may comprise 100% of the total dosage of a given active agent administered in a single unit dose. Alternatively, an immediate-release component may be included as a component in a combined release profile formulation that may provide about 1% to about 60% of the total dosage of the active agent(s) to be delivered by the pharmaceutical formulation. For example, the immediate-release component may provide about 5%-60%, about 10% to about 60%, about 10% to about 50%, about 10% to about 40%, about 10% to about 30%, about 10% to about 20%, about 20% to about 60%, about 20% to about 50%, about 20% to about 30%, about 30% to about 60%, about 30% to about 50%, about 40% to about 60%, about 40% to about 50%, about 45% to about 60% or about 45% to about 50% of the total dosage of the active agent(s) to be delivered by the formulation. In alternate embodiments, the immediate-release component provides about 2, 4, 5, 10, 15, 20, 25, 30, 35, 40, 45, 50, 55 or 60% of the total dosage of the active agent(s) to be delivered by the formulation.

In some embodiments, the immediate-release or delayed-release formulation comprises an active core comprised of one or more inert particles, each in the form of a bead, pellet, pill, granular particle, microcapsule, microsphere, microgranule, nanocapsule, or nanosphere coated on its surfaces with drugs in the form of e.g., a drug-containing film-forming composition using, for example, fluid bed techniques or other methodologies known to those of skill in the art. The inert particle can be of various sizes, so long as it is large enough to remain poorly dissolved. Alternatively, the active core may be prepared by granulating and milling and/or by extrusion and spheronization of a polymer composition containing the drug substance.

The amount of drug in the core will depend on the dose that is required, and typically varies from about 5 to 90 weight %. Generally, the polymeric coating on the active core will be from about 1 to 50% based on the weight of the coated particle, depending on the lag time and type of release profile required and/or the polymers and coating solvents chosen. Those skilled in the art will be able to select an appropriate amount of drug for coating onto or incorporating into the core to achieve the desired dosage. In one embodiment, the inactive core may be a sugar sphere or a buffer crystal or an encapsulated buffer crystal such as calcium carbonate, sodium bicarbonate, fumaric acid, tartaric acid, etc. which alters the microenvironment of the drug to facilitate its release.

In some embodiments, the delayed-release formulation is formed by coating a water soluble/dispersible drug-containing particle, such as a bead, with a mixture of a water insoluble polymer and an enteric polymer, wherein the water insoluble polymer and the enteric polymer may be present at a weight ratio of from 4:1 to 1:1, and the total weight of the coatings is 10 to 60 weight % based on the total weight of the coated beads. The drug layered beads may optionally include an inner dissolution rate controlling membrane of ethylcellulose. The composition of the outer layer, as well as the individual weights of the inner and outer layers of the polymeric membrane are optimized for achieving desired circadian rhythm release profiles for a given active, which are predicted based on in vitro/in vivo correlations.

In other embodiments the formulations comprise a mixture of immediate-release drug-containing particles without a dissolution rate controlling polymer membrane and delayed-release beads exhibiting, for example, a lag time of 2-4 hours following oral administration, thus providing a two-pulse release profile. In yet other embodiments the formulations comprise a mixture of two types of delayed-release beads: a first type that exhibits a lag time of 1-3 hours and a second type that exhibits a lag time of 4-6 hours.

Preferably, the formulations are designed with release profiles to limit interference with restful sleep, wherein the formulation releases the medicine when the individual would normally be awakened by an urge to urinate. For example, consider an individual who begins sleeping at 11 PM and is normally awakened at 12:30 AM, 3:00 AM, and 6:00 AM to urinate. A delayed, extended-release vehicle could be taken at 10 PM and start delivering the medicine at 12 AM and gradually release the medicine over a period of 5-8 hours, thereby delaying or eliminating the need to urinate. In other embodiments, the formulations are designed with a release profile that a fraction of the medicine (e.g., 20-60%) is released immediately or within 2 hours of administration and the rest is released over an extended period of time. The pharmaceutical composition may be administered daily or administered on an as needed basis. In certain embodiments, the pharmaceutical composition is administered to the subject prior to bedtime. In some embodiments, the pharmaceutical composition is administered immediately before bedtime. In some embodiments, the pharmaceutical composition is administered within about two hours before bedtime, preferably within about one hour before bedtime. In another embodiment, the pharmaceutical composition is administered about two hours before bedtime. In a further embodiment, the pharmaceutical composition is administered at least two hours before bedtime. In another embodiment, the pharmaceutical composition is administered about one hour before bedtime. In a further embodiment, the pharmaceutical composition is administered at least one hour before bedtime. In a still further embodiment, the pharmaceutical composition is administered less than one hour before bedtime. In still another embodiment, the pharmaceutical composition is administered immediately before bedtime. Preferably, the pharmaceutical composition is administered orally. Suitable compositions for oral administration include, but are not limited to: tablets, coated tablets, dragees, capsules, powders, granulates and soluble tablets, and liquid forms, for example, suspensions, dispersions or solutions.

The appropriate dosage ("therapeutically effective amount") of the active agent(s) in the immediate-release component or the extended-release component will depend, for example, on the severity and course of the condition, the mode of administration, the bioavailability of the particular agent(s), the age and weight of the patient, the patient's clinical history and response to the active agent(s), discretion of the physician, etc.

As a general proposition, the therapeutically effective amount of the active agent(s) in the immediate-release component, the extended-release component or the delayed-extended-release component is administered in the range of about 100 µg/kg body weight/day to about 100 mg/kg body weight/day whether by one or more administrations. In some embodiments, the range of each active agent administered daily in a single dose or in multiple does is from about 100 µg/kg body weight/day to about 50 mg/kg body weight/day, 100 µg/kg body weight/day to about 10 mg/kg body weight/day, 100 µg/kg body weight/day to about 1 mg/kg body weight/day, 100 µg/kg body weight/day to about 10 mg/kg body weight/day, 500 µg/kg body weight/day to about 100 mg/kg body weight/day, 500 µg/kg body weight/day to about 50 mg/kg body weight/day, 500 µg/kg body weight/day to about 5 mg/kg body weight/day, 1 mg/kg body weight/day to about 100 mg/kg body weight/day, 1 mg/kg body weight/day to about 50 mg/kg body weight/day, 1 mg/kg body weight/day to about 10 mg/kg body weight/day, 5 mg/kg body weight/dose to about 100 mg/kg body weight/day, 5 mg/kg body weight/dose to about 50 mg/kg body weight/day, 10 mg/kg body weight/day to about 100 mg/kg body weight/day, and 10 mg/kg body weight/day to about 50 mg/kg body weight/day.

The active agent(s) described herein may be included in an immediate-release component or an extended-release component, a delayed-extended-release component or combinations thereof for daily oral administration at a single dose or combined dose range of 1 mg to 2000 mg, 5 mg to 2000 mg, 10 mg to 2000 mg, 50 mg to 2000 mg, 100 mg to 2000 mg, 200 mg to 2000 mg, 500 mg to 2000 mg, 5 mg to 1800 mg, 10 mg to 1600 mg, 50 mg to 1600 mg, 100 mg to 1500 mg, 150 mg to 1200 mg, 200 mg to 1000 mg, 300 mg to 800 mg, 325 mg to 500 mg, 1 mg to 1000 mg, 1 mg to 500 mg, 1 mg to 200 mg, 5 mg to 1000 mg, 5 mg to 500 mg, 5 mg to 200 mg, 10 mg to 1000 mg, 10 mg to 500 mg, 10 mg to 200 mg, 50 mg to 1000 mg, 50 mg to 500 mg, 50 mg to 200 mg, 250 mg to 1000 mg, 250 mg to 500 mg, 500 mg to 1000 mg, 500 mg to 2000 mg. As expected, the dosage will be dependent on the weight, size, age and condition of the patient.

In some embodiments, the pharmaceutical composition comprises a single analgesic agent, and one or more α-blockers or one or more 5α-reductase inhibitors. In one embodiment, the single analgesic agent is aspirin. In another embodiment, the single analgesic agent is ibuprofen. In another embodiment, the single analgesic agent is naproxen or naproxen sodium. In another embodiment, the single analgesic agent is indomethacin. In another embodiment, the single analgesic agent is nabumetone. In another embodiment, the single analgesic agent is acetaminophen. In another embodiment, the single analgesic agent is acetaminophen and the one or more α-blockers comprise tamsulosin. In another embodiment, the single analgesic agent is acetaminophen and the one or more 5α-reductase inhibitors comprise finasteride.

In some embodiments, the single analgesic agent is given at a daily dose of 1 mg to 2000 mg, 5 mg to 2000 mg, 20 mg to 2000 mg, 5 mg to 1000 mg, 20 mg to 1000 mg, 50 mg to 500 mg, 100 mg to 500 mg, 250 mg to 500 mg, 250 mg to 1000 mg or 500 mg to 1000 mg. In certain embodiments, the pharmaceutical composition comprises acetylsalicylic acid, ibuprofen, naproxen, naproxen sodium, indomethancin, nabumetone or acetaminophen as a single analgesic agent and the analgesic agent is administered orally at a daily dose in the range of 5 mg to 2000 mg, 20 mg to 2000 mg, 5 mg to 1000 mg, 20 mg to 1000 mg, 50 mg to 500 mg, 100 mg to 500 mg, 250 mg to 500 mg, 250 mg to 1000 mg or 500 mg to 1000 mg. In some embodiments, a second analgesic agent is given at a daily dose of 1 mg to 2000 mg, 5 mg to 2000 mg, 20 mg to 2000 mg, 5 mg to 1000 mg, 20 mg to 1000 mg, 50 mg to 500 mg, 100 mg to 500 mg, 250 mg to 500 mg, 250 mg to 1000 mg or 500 mg to 1000 mg.

In other embodiments, the pharmaceutical composition comprises a pair of analgesic agents and one or more α-blockers. Examples of such paired analgesic agents include, but are not limited to, acetylsalicylic acid and ibuprofen, acetylsalicylic acid and naproxen sodium, acetylsalicylic acid and nabumetone, acetylsalicylic acid and acetaminophen, acetylsalicylic acid and indomethancin, ibuprofen and naproxen sodium, ibuprofen and nabumetone, ibuprofen and acetaminophen, ibuprofen and indomethancin, naproxen, naproxen sodium and nabumetone, naproxen sodium and acetaminophen, naproxen sodium and indomethancin, nabumetone and acetaminophen, nabumetone and indomethancin, and acetaminophen and indomethancin. The paired analgesic agents are mixed at a weight ratio in the range of 0.1:1 to 10:1, 0.2:1 to 5:1 or 0.3:1 to 3:1, with a combined dose in the range of 5 mg to 2000 mg, 20 mg to 2000 mg, 100 mg to 2000 mg, 200 mg to 2000 mg, 500 mg to 2000 mg, 5 mg to 1500 mg, 20 mg to 1500 mg, 100 mg to 1500 mg, 200 mg to 1500 mg, 500 mg to 1500 mg, 5 mg to 1000 mg, 20 mg to 1000 mg, 100 mg to 1000 mg, 250 mg to 500 mg, 250 mg to 1000 mg, 250 mg to 1500 mg, 500 mg to 1000 mg, 500 mg to 1500 mg, 1000 mg to 1500 mg, and 1000 mg to 2000 mg. In one embodiment, the paired analgesic agents are mixed at a weight ratio of 1:1.

In some other embodiments, the pharmaceutical composition of the present application further comprises one or more antimuscarinic agents. Examples of the antimuscarinic agents include, but are not limited to, oxybutynin, solifenacin, darifenacin, fesoterodine, tolterodine, trospium and atropine. The daily dose of antimuscarinic agent is in the range of 0.01 mg to 100 mg, 0.1 mg to 100 mg, 1 mg to 100 mg, 10 mg to 100 mg, 0.01 mg to 25 mg, 0.1 mg to 25 mg, 1 mg to 25 mg, 10 mg to 25 mg, 0.01 mg to 10 mg, 0.1 mg to 10 mg, 1 mg to 10 mg, 10 mg to 100 mg and 10 mg to 25 mg.

In certain embodiments, the pharmaceutical composition comprises one or more α-blockers, an analgesic agent selected from the group consisting of cetylsalicylic acid, ibuprofen, naproxen, naproxen sodium, nabumetone, acetaminophen and indomethancin, and an antimuscarinic agent selected from the group consisting of oxybutynin, solifenacin, darifenacin and atropine.

Another aspect of the present application relates to a method for reducing the frequency of urination by administering to a person in need thereof a pharmaceutical composition formulated in an immediate-release formulation. The pharmaceutical composition comprises one or more analgesic agents and one or more additional active ingredients selected from the group consisting of 5α-reductase inhibitors, α-blockers, antimuscarinic agents, antidiuretic agents and spasmolytics. The pharmaceutical composition may be formulated into a tablet, capsule, dragee, powder, granulate, liquid, gel or emulsion form. Said liquid, gel or emulsion may be ingested by the subject in naked form or contained within a capsule.

In certain embodiments, the analgesic agent is selected from the group consisting of salicylates, aspirin, salicylic acid, methyl salicylate, diflunisal, salsalate, olsalazine, sulfasalazine, para-aminophenol derivatives, acetanilide, acetaminophen, phenacetin, fenamates, mefenamic acid, meclofenamate, sodium meclofenamate, heteroaryl acetic acid derivatives, tolmetin, ketorolac, diclofenac, propionic acid derivatives, ibuprofen, naproxen sodium, naproxen, fenoprofen, ketoprofen, flurbiprofen, oxaprozin; enolic acids, oxicam derivatives, piroxicam, meloxicam, tenoxicam, ampiroxicam, droxicam, pivoxicam, pyrazolon derivatives, phenylbutazone, oxyphenbutazone, antipyrine, aminopyrine, dipyrone, coxibs, celecoxib, rofecoxib, nabumetone, apazone, nimesulide, indomethacin, sulindac, etodolac, diflunisal and isobutylphenyl propionic acid. The antimuscarinic agent is selected from the group consisting of oxybutynin, solifenacin, darifenacin and atropine.

In some embodiments, the pharmaceutical composition comprises a single analgesic agent, a single α-blocker and a single antimuscarinic agent. In some embodiments, the pharmaceutical composition comprises a single analgesic agent, a single 5α-reductase inhibitor and a single antimuscarinic agent. In one embodiment, the single analgesic agent is aspirin. In another embodiment, the single analgesic agent is ibuprofen. In another embodiment, the single analgesic agent is naproxen or naproxen sodium. In another embodiment, the single analgesic agent is indomethacin. In another embodiment, the single analgesic agent is nabumetone. In another embodiment, the single analgesic agent is acetaminophen. In another embodiment, the single α-blocker is tamsulosin. The analgesic agent, α-blocker, 5α-reductase inhibitor and antimuscarinic agent may be given at doses in the ranges described above. In some embodiments, the pharmaceutical composition further comprises an antidiuretic agent or a spasmolytic.

In some embodiments, the pharmaceutical composition comprises one or more analgesic agents, individually or in combination, in an amount between 50-2000 mg, 50-1500 mg, 50-1200 mg, 50-1000 mg, 50-800 mg, 50-600 mg, 50-500 mg, 50-400 mg, 50-300 mg, 50-250 mg, 50-200 mg, 50-150 mg, 50-100 mg, 100-2000 mg, 100-1500 mg, 100-1200 mg, 100-1000 mg, 100-800 mg, 100-600 mg, 100-400 mg, 100-250 mg, 250-2000 mg, 250-1500 mg, 250-1200 mg, 250-1000 mg, 250-800 mg, 250-600 mg, 250-400 mg, 400-2000 mg, 400-1500 mg, 400-1200 mg, 400-1000 mg, 400-800 mg, 400-600 mg, 600-2000 mg, 600-1500 mg, 600-1200 mg, 600-1000 mg, 600-800 mg, 800-2000 mg, 800-1500 mg, 800-1200 mg, 800-1000 mg, 1000-2000 mg, 1000-1500 mg, 1000-1200 mg, 1200-2000 mg, 1200-1500 mg or 1500-2000 mg, wherein the composition is formulated for extended release with a release profile in which the one or more analgesic agents are released continuously over a period of 5-24 hours, 5-8, 8-16 hours or 16-24 hours.

In some embodiments, the composition is formulated for extended release with a release profile in which at least 90% of the active ingredients are released continuously over a period of 5-24 hours, 5-8, 8-16 hours or 16-24 hours.

In some embodiments, the composition is formulated for extended release with a release profile in which the active ingredients are released continuously over a period of 5, 6, 7, 8, 10, 12, 14, 16, 18, 20, 22 or 24 hours.

In other embodiments, the composition is formulated for extended release with a release profile in which the active ingredients and are released at a steady rate over a period of 5-24 hours, 5-8, 8-16 hours or 16-24 hours. In other embodiments, the composition is formulated for extended release with a release profile in which the active ingredients are released at a steady rate over a period of 5, 6, 7, 8, 10, 12, 14, 16, 18, 20, 22 or 24 hours. As used herein, "a steady rate over a period of time" is defined as a release profile in which the release rate at any point during a given period of time is within 30%-300% of the average release rate over that given period of time. For example, if 80 mg of aspirin is released at a steady rate over a period of 8 hours, the average release rate is 10 mg/hr during this period of time and the actual release rate at any time during this period is within the range of 3 mg/hr to 30 mg/hr (i.e., within 30%-300% of the average release rate of 10 mg/hr during the 8 hour period).

In some embodiments, the analgesic agent is selected from the group consisting of aspirin, ibuprofen, naproxen sodium, naproxen, indomethacin, nabumetone and acetaminophen. The pharmaceutical composition is formulated to provide a steady release of small amount of the analgesic agent to maintain an effective drug concentration in the blood such that the overall amount of the drug in a single dosage is reduced compared to the immediate release formulation. The other active ingredients may be released immediately after administration or released with the analgesic agent.

In some embodiments, the pharmaceutical composition comprises 50-400 mg, 50-250 mg, 250-400 mg or 400-600 mg of an analgesic agent formulated for extended release with a release profile in which at least 90% of the analgesic agent is released continuously, or at a steady rate, over a period of 5-8, 8-16 or 16-24 hours. The other active ingredients may be released immediately after administration or released with the analgesic agent.

In one particular embodiment, the pharmaceutical composition comprises 50-250 mg of acetaminophen formulated for extended release with a release profile in which at least 90% of acetaminophen is released continuously, or at a steady rate, over a period of 5-8, 8-16 or 16-24 hours. The other active ingredients may be released immediately after administration or released with the analgesic agent.

In another particular embodiment, the pharmaceutical composition comprises 250-400 mg of acetaminophen formulated for extended release with a release profile in which 90% of acetaminophen is released continuously, or at a steady rate over a period of 5-8, 8-16 or 16-24 hours. The other active ingredients may be released immediately after administration or released with the analgesic agent.

In another particular embodiment, the pharmaceutical composition comprises 400-600 mg of acetaminophen formulated for extended release with a release profile in which 90% of acetaminophen is released continuously, or at a steady rate over a period of 5-8, 8-16 or 16-24 hours. The other active ingredients may be released immediately after administration or released with the analgesic agent.

In another particular embodiment, the pharmaceutical composition comprises 600-800 mg of acetaminophen formulated for extended release with a release profile in which 90% of acetaminophen is released continuously, or at a steady rate over a period of 5-8, 8-16 or 16-24 hours. The other active ingredients may be released immediately after administration or released with the analgesic agent.

In yet another embodiment, the pharmaceutical composition comprises 800-1000 mg of acetaminophen formulated for extended release with a release profile in which at least 90% of acetaminophen is released continuously, or at a steady rate over a period of 5-8, 8-16 or 16-24 hours. The other active ingredients may be released immediately after administration or released with the analgesic agent.

In some other embodiments, the pharmaceutical composition comprises one or more analgesic agent(s), individually or in combination, in an amount between 50-2000 mg, 50-1500 mg, 50-1200 mg, 50-1000 mg, 50-800 mg, 50-600 mg, 50-500 mg, 50-400 mg, 50-300 mg, 50-250 mg, 50-200 mg, 100-2000 mg, 100-1500 mg, 100-1200 mg, 100-1000 mg, 100-800 mg, 100-600 mg, 100-500 mg, 100-400 mg, 100-300 mg, 100-200 mg, 200-2000 mg, 200-1500 mg, 200-1200 mg, 200-1000 mg, 200-800 mg, 200-600 mg, 200-400 mg, 400-2000 mg, 400-1500 mg, 400-1200 mg, 400-1000 mg, 400-800 mg, 400-600 mg, 600-2000 mg, 600-1500 mg, 600-1200 mg, 600-1000 mg, 600-800 mg, 800-2000 mg, 800-1500 mg, 800-1200 mg, 800-1000 mg, 1000-2000 mg, 1000-1500 mg, 1000-1200 mg, 1200-2000 mg, 1200-1500 mg or 1500-2000 mg, wherein the analgesic agent(s) are formulated for extended release, characterized by a two-phase release profile in which 20-50% of the analgesic agent(s) are released within 2 hours of administration and the remainder are released continuously, or at a steady rate, over a period of 5-24 hours. The other active ingredients may be released immediately after administration or released with the analgesic agent.

In yet another embodiment, the analgesic agent(s) is formulated for extended release with a two-phase release profile in which 20, 30, 40 or 50% of the analgesic agent(s) are released within 2 hours of administration and the remainder are released continuously, or at a steady rate, over a period of 5-8, 8-16 or 16-24 hours. In one embodiment, the analgesic agent(s) are selected from the group consisting of aspirin, ibuprofen, naproxen sodium, naproxen, indomethacin, nabumetone and acetaminophen. In another embodiment, the analgesic agent is acetaminophen. In some embodiments, the pharmaceutical composition further comprises an antimuscarinic agent, an antidiuretic agent or a spasmolytic. The other active ingredients may be released immediately after administration or released with the analgesic agent.

In another embodiment, the pharmaceutical composition comprises 50-400 mg of acetaminophen formulated for extended release with a two-phase release profile in which 20%, 30%, 40% or 50% of the acetaminophen is released within 2 hours of administration and the remainder is released continuously, or at a steady rate, over a period of 5-8, 8-16 or 16-24 hours. The other active ingredients may be released immediately after administration or released with the analgesic agent.

In another embodiment, the pharmaceutical composition comprises 100-300 mg of acetaminophen formulated for extended release with a two-phase release profile in which 20%, 30%, 40% or 50% of the acetaminophen is released within 2 hours of administration and the remainder is released at a steady rate over a period of 5-8, 8-16 or 16-24 hours. The other active ingredients may be released immediately after administration or released with the analgesic agent.

In another embodiment, the pharmaceutical composition comprises 400-600 mg of acetaminophen formulated for extended release with a two-phase release profile in which 20%, 30%, 40% or 50% of the acetaminophen is released within 2 hours of administration and the remainder is released continuously, or at a steady rate, in a period of 5-8, 8-16 or 16-24 hours. The other active ingredients may be released immediately after administration or released with the analgesic agent.

In another embodiment, the pharmaceutical composition comprises 600-800 mg of acetaminophen formulated for extended release with a two-phase release profile in which 20%, 30%, 40% or 50% of the acetaminophen is released within 2 hours of administration and the remainder is released continuously, or at a steady rate, in a period of 5-8, 8-16 or 16-24 hours. The other active ingredients may be released immediately after administration or released with the analgesic agent.

In another embodiment, the pharmaceutical composition comprises 800-1000 mg of acetaminophen formulated for extended release with a two-phase release profile in which 20%, 30%, 40% or 50% of the acetaminophen is released within 2 hours of administration and the remainder is released continuously, or at a steady rate, in a period of 5-8, 8-16 or 16-24 hours. The other active ingredients may be released immediately after administration or released with the analgesic agent.

In another embodiment, the pharmaceutical composition comprises 1000-1200 mg of acetaminophen formulated for extended release with a two-phase release profile in which 20%, 30%, 40% or 50% of the acetaminophen is released within 2 hours of administration and the remainder is released continuously, or at a steady rate, in a period of 5-8, 8-16 or 16-24 hours. The other active ingredients may be released immediately after administration or released with the analgesic agent.

Another aspect of the present application relates to a method for treating nocturia by administering to a subject in need thereof (1) one or more analgesic agents, (2) an α-blocker or a 5α-reductase inhibitor or both, and (3) one or more antidiuretic agents. In certain embodiments, the antidiuretic agent(s) act to: (1) increase vasopressin secretion; (2) increase vasopressin receptor activation; (3) reduce secretion of atrial natriuretic peptide (ANP) or C-type natriuretic peptide (CNP); or (4) reduce ANP and/or CNP receptor activation.

Exemplary antidiuretic agents include, but are not limited to, antidiuretic hormone (ADH), angiotensin II, aldosterone, vasopressin, vasopressin analogs (e.g., desmopressin argipressin, lypressin, felypressin, ornipressin, terlipressin); vasopressin receptor agonists, atrial natriuretic peptide (ANP) and C-type natriuretic peptide (CNP) receptor (i.e., NPR1, NPR2, NPR3) antagonists (e.g., HS-142-1, isatin, [Asu7,23']b-ANP-(7-28)], anantin, a cyclic peptide from *Streptomyces coerulescens*, and 3G12 monoclonal antibody); somatostatin type 2 receptor antagonists (e.g., somatostatin), and pharmaceutically-acceptable derivatives, analogs, salts, hydrates, and solvates thereof.

In certain embodiments, the one or more analgesic agents, the α-blocker and/or the 5α-reductase inhibitor are formulated for extended release, and the one or more antidiuretic agents are formulated for immediate release. In other embodiments, the one or more analgesic agents, the α-blocker and/or the 5α-reductase inhibitor are formulated for delayed release and the antidiuretic is formulated for immediate release. In some embodiments, the delayed release formulation delays the release of the active ingredient (e.g., the analgesic agent, antimuscarinic agent, antidiuretic agent and spasmolytic) for a period of 1, 2, 3, 4 or 5 hours.

Another aspect of the present application relates to a method for reducing the frequency of urination by administering to a person in need thereof a first pharmaceutical composition comprising a diuretic, followed with a second pharmaceutical composition comprising (1) one or more analgesic agents and (1) one or more α-blockers, one or more 5α-reductase inhibitors, or both. The first pharmaceutical composition is dosed and formulated to have a diuretic effect within 6 hours of administration and is administered at least 8 or 7 hours prior to bedtime. The second pharmaceutical composition is administered within 2 hours prior to bedtime. The first pharmaceutical composition is formulated for immediate-release and the second pharmaceutical composition is formulated for extended-release or delayed, extended-release.

Examples of diuretics include, but are not limited to, acidifying salts, such as $CaCl_2$ and $NH_4Cl$; arginine vasopressin receptor 2 antagonists, such as amphotericin B and lithium citrate; aquaretics, such as Goldenrod and Junipe; Na—H exchanger antagonists, such as dopamine; carbonic anhydrase inhibitors, such as acetazolamide and dorzolamide; loop diuretics, such as bumetanide, ethacrynic acid, furosemide and torsemide; osmotic diuretics, such as glucose and mannitol; potassium-sparing diuretics, such as amiloride, spironolactone, triamterene, potassium canrenoate; thiazides, such as bendroflumethiazide and hydrochlorothiazide; and xanthines, such as caffeine, theophylline and theobromine.

In some embodiments, the second pharmaceutical composition further comprises one or more antimuscarinic agents. Examples of the antimuscarinic agents include, but are not limited to, oxybutynin, solifenacin, darifenacin, fesoterodine, tolterodine, trospium and atropine. The second pharmaceutical composition may be formulated in immediate-release formulation or delayed-release formulation or extended-release formulation. In some other embodiments, the second pharmaceutical composition further comprises one or more antidiuretic agents. In some other embodiments, the second pharmaceutical composition further comprises one or more spasmolytics. Another aspect of the present application relates to a method for reducing the frequency of urination by administering to a subject in need thereof, two or more analgesic agents alternatively to prevent the development of drug resistance. In one embodiment, the method comprises administering a first analgesic agent for a first period of time and then administering a second analgesic agent for a second period of time. In another embodiment, the method further comprises administering a third analgesic agent for a third period of time. The first, second and third analgesic agents are different from each other and at least one of which is formulated for extended-release or delayed, extended-release. In one embodiment, the first analgesic agent is acetaminophen, the second analgesic agent is ibuprofen and the third analgesic agent is naproxen sodium. The length of each period may vary depending on the subject's response to each analgesic agent. In some embodiments, each period lasts from 3 days to three weeks. In another embodiment, the first, second and third analgesic are all formulated for extended-release or delayed, extended-release.

Another aspect of the present application relates to a pharmaceutical composition comprising a plurality of active ingredients and a pharmaceutically acceptable carrier, wherein at least one of the plurality of active ingredients is formulated for extended-release or delayed, extended-release. In some embodiments, the plurality of active ingredients comprises one or more analgesics and one or more antidiuretic agents. In other embodiments, the plurality of active ingredients comprises one or more analgesics, one or more α-blockers, one or more 5α-reductase inhibitors and one or more antimuscarinic agents. In other embodiments, the plurality of active ingredients comprises one or more analgesics, one or more α-blockers, one or more antidiuretic agents and one or more antimuscarinic agent. In other embodiments, the pharmaceutical composition comprises two different analgesics selected from the group consisting of cetylsalicylic acid, ibuprofen, naproxen sodium, naproxen, nabumetone, acetaminophen and indomethancin. In yet other embodiments, the pharmaceutical composition comprises one analgesic selected from the group consisting of cetylsalicylic acid, ibuprofen, naproxen sodium, nabumetone, acetaminophen and indomethancin; one or more α-blockers and an antimuscarinic agent selected from the group consisting of oxybutynin, solifenacin, darifenacin and atropine.

In other embodiments, the pharmaceutical composition of the present application further comprises one or more spasmolytics and/or one or more antidiuretics. Examples of spasmolytics include, but are not limited to, carisoprodol, benzodiazepines, baclofen, cyclobenzaprine, metaxalone, methocarbamol, clonidine, clonidine analog, and dantrolene. In some embodiments, the spasmolytics is used at a daily dose of 1 mg to 1000 mg, 1 mg to 100 mg, 10 mg to 1000 mg, 10 mg to 100 mg, 20 mg to 1000 mg, 20 mg to 800 mg, 20 mg to 500 mg, 20 mg to 200 mg, 50 mg to 1000 mg, 50 mg to 800 mg, 50 mg to 200 mg, 100 mg to 800 mg, 100 mg to 500 mg, 200 mg to 800 mg, and 200 mg to 500 mg. The spasmolytics may be formulated, alone or together with other active ingredient(s) in the pharmaceutical composition, for immediate-release, extended-release, delayed-extended-release or combinations thereof.

In some embodiments, the pharmaceutical composition comprises one or more analgesic agents selected from the group consisting of aspirin, ibuprofen, naproxen, naproxen sodium, indomethacin, nabumetone and acetaminophen in a total amount of 50-400 mg per agent, one or more α-blockers and one or more antimuscarinic agents selected from the group consisting of oxybutynin, solifenacin, darifenacin and atropine in a total amount of 1-25 mg, wherein the pharmaceutical composition is formulated for extended release with a two-phase release profile in which 20-60% of the active ingredients are released within 2 hours of administration, and the remainder of the active ingredients are released continuously, or at a steady rate, in a period of 5-24 hours, 5-8 hours, 8-16 hours or 16-24 hours.

In some embodiments, the pharmaceutical composition comprises one or more analgesic agents selected from the group consisting of aspirin, ibuprofen, naproxen, naproxen sodium, indomethacin, nabumetone and acetaminophen in an amount of 50-400 mg per agent, one or more α-blockers and one or more antidiuretic agents selected from the group consisting of antidiuretic hormone (ADH), angiotensin II, aldosterone, vasopressin, vasopressin analogs (e.g., desmopressin argipressin, lypressin, felypressin, ornipressin, terlipressin); vasopressin receptor agonists, atrial natriuretic peptide (ANP) and C-type natriuretic peptide (CNP) receptor (i.e., NPR1, NPR2, NPR3) antagonists (e.g., HS-142-1, isatin, [Asu7,23']b-ANP-(7-28)], anantin, a cyclic peptide from *Streptomyces coerulescens*, and 3G12 monoclonal antibody); somatostatin type 2 receptor antagonists (e.g., somatostatin), and pharmaceutically-acceptable derivatives, analogs, salts, hydrates, and solvates thereof, wherein the pharmaceutical composition is formulated for extended release with a two-phase release profile in which 20-60% of the active ingredients are released within 2 hours of administration, and the remainder are released continuously, or at a steady rate, in a period of 5-24 hours, 5-8 hours, 8-16 hours or 16-24 hours.

In some embodiments, the pharmaceutical composition comprises (1) one or more analgesic agents selected from the group consisting of aspirin, ibuprofen, naproxen, naproxen sodium, indomethacin, nabumetone and acetaminophen in an amount of 50-400 mg per agent, (2) one or more α-blockers, or one or more 5α-reductase inhibitors, or both, and (3) one or more spasmolytics selected from the group consisting of carisoprodol, benzodiazepines, baclofen, cyclobenzaprine, metaxalone, methocarbamol, clonidine, clonidine analog, and dantrolene in a total amount of 50-500 mg, wherein the pharmaceutical composition is formulated for extended release with a two-phase release profile in which 20-60% of the active ingredients are released within 2 hours of administration, and the remainder are released continuously, or at a steady rate, in a period of 5-24 hours, 5-8 hours, 8-16 hours or 16-24 hours.

As used herein, "pharmaceutically acceptable carrier" includes any and all solvents, dispersion media, coatings, antibacterial and antifungal agents, isotonic and absorption delaying agents, sweeteners and the like. The pharmaceutically acceptable carriers may be prepared from a wide range of materials including, but not limited to, flavoring agents, sweetening agents and miscellaneous materials such as buffers and absorbents that may be needed in order to prepare a particular therapeutic composition. The use of such media and agents with pharmaceutically active substances is well known in the art. Except insofar as any conventional media or agent is incompatible with the active ingredient, its use in the therapeutic compositions is contemplated.

Another aspect of the present application relates to a pharmaceutical composition that comprises a first component having an immediate-release subcomponent and an extended-release subcomponent, wherein the first component is formulated to release the subcomponents immediately after administration; and a second component comprising an immediate-release subcomponent and an extended-release subcomponent, wherein the second component is formulated for a delayed-release of the subcomponents. In some embodiments, at least one of the subcomponents in the first component or the second component comprises an active ingredient comprising one or more analgesic agents, and at least one of the subcomponents in the first component or the second component comprises an active ingredient comprising an α-blocker, a 5α-reductase inhibitor or both.

In some embodiments, each of the subcomponents in the first component or the second component comprises an active ingredient comprising one or more analgesic agents and/or an α-blocker, and/or a 5α-reductase inhibitor.

In some embodiments, the one or more analgesic agents are selected from the group consisting of aspirin, ibuprofen, naproxen, naproxen sodium, indomethacin, nabumetone, and acetaminophen.

In some related embodiments, the immediate-release subcomponent and the extended-release subcomponent in the first component each comprises an active ingredient comprising one or more analgesic agents, and/or an α-blocker, and/or a 5α-reductase inhibitor. In other embodiments, the immediate-release subcomponent and the extended-release subcomponent in the second component each comprises an active ingredient comprising one or more analgesic agents, and/or an α-blocker, and/or a 5α-reductase inhibitor.

In some embodiments, the one or more analgesic agents comprise acetaminophen. In yet other embodiments, at least one of the subcomponents in the first component or the second component comprises an active ingredient comprising one or more analgesic agents and an α-blocker. In yet other embodiments, at least one of the subcomponents in the first component or the second component comprises an active ingredient comprising one or more analgesic agents and an 5α-reductase inhibitor. In yet other embodiments, at least one of the subcomponents in the first component or the second component comprises an active ingredient comprising one or more analgesic agents, and an α-blocker and a 5α-reductase inhibitor.

In some related embodiments, the second component is coated with an enteric coating.

In some related embodiments, the second component is formulated to release the subcomponents after a lag time of 0.1-12 hours, 0.5-12 hours, 1-12 hours, 2-12 hours, 1-4 hours, 2-4 hours, 4-6 hours, 4-8 hours or 4-12 hours following oral administration.

In some related embodiments, the extended-release subcomponent in the first component is formulated to release its active ingredient over a time interval of about 2-10 hours.

In some related embodiments, the extended-release subcomponent in the second component is formulated to release its active ingredient over a time interval of about 2-10 hours.

In some related embodiments, the active ingredient in the immediate-release subcomponent and the extended-release subcomponent in the first component further comprises an antimuscarinic agent. In some embodiments, the active ingredient in the immediate-release subcomponent and the extended-release subcomponent in the second component further comprises an antimuscarinic agent. In some embodiments, the active ingredient in the immediate-release subcomponent and the extended-release subcomponent in both the first and the second component further comprises an antimuscarinic agent.

In some related embodiments, the active ingredient in the immediate-release subcomponent and the extended-release subcomponent in the first component further comprises an antidiuretic agent. In some embodiments, the active ingredient in the immediate-release subcomponent and the extended-release subcomponent in the second component further comprises an antidiuretic agent. In some embodiments, the active ingredient in the immediate-release subcomponent and the extended-release subcomponent in both the first and the second component further comprises an antidiuretic agent.

In some related embodiments, the active ingredient in the immediate-release subcomponent and the extended-release subcomponent in the first component further comprises a spasmolytic. In some embodiments, the active ingredient in the immediate-release subcomponent and the extended-release subcomponent in the second component further comprises a spasmolytic. In some embodiments, the active ingredient in the immediate-release subcomponent and the extended-release subcomponent in both the first and the second component further comprises a spasmolytic.

In some related embodiments, the immediate-release subcomponent and the extended-release subcomponent in the first component each comprises an analgesic agent, such as acetaminophen, in an amount of 5-2000 mg. In some embodiments, the immediate-release subcomponent and the extended-release subcomponent in the second component each comprises an analgesic agent, such as acetaminophen, in an amount of 5-2000 mg. In some embodiments, the active ingredient in the immediate-release subcomponent and the extended-release subcomponent in both the first and the second component each comprises an analgesic agent, such as acetaminophen, in an amount of 5-2000 mg.

In some related embodiments, the immediate-release subcomponent and the extended-release subcomponent in the first component each comprises tamsulosin. In some related embodiments, the immediate-release subcomponent and the extended-release subcomponent in the first component each comprises finasteride. In some related embodiments, the immediate-release subcomponent and the extended-release subcomponent in the first component each comprises tamsulosin and finasteride.

In some related embodiments, the active ingredient in the immediate-release subcomponent of the first component and the active ingredient in the immediate-release subcomponent of the second component both comprise an analgesic agent, such as acetaminophen. In some embodiments, the active ingredient in the immediate-release subcomponent of the first component and the active ingredient in the immediate-release subcomponent of the second component comprise different analgesic agents.

Another aspect of the present application relates to a pharmaceutical composition that comprises a first component comprising an immediate-release subcomponent, wherein the immediate-release subcomponent comprises an active ingredient comprising one or more agents selected from the group consisting of analgesic agents, α-blockers and 5α-reductase inhibitors, wherein the first component is formulated to release its subcomponent immediately after oral administration; and a second component comprising an immediate-release subcomponent and an extended-release subcomponent, wherein the second component is formulated to release its subcomponent after gastric emptying, wherein the immediate-release subcomponent and the extended-release subcomponent in the second component each comprises an active ingredient comprising one or more agents selected from the group consisting of analgesic agents, α-blockers and 5α-reductase inhibitors.

In some related embodiments, the second component is formulated to release the subcomponents after a lag time of 2-12 hours, 2-4 hours, 2-6 hours, 2-8 hours or 4-8 hours following oral administration.

In some related embodiments, the active ingredient in the immediate-release subcomponent and the extended-release subcomponent of the second component comprises one or more analgesic agents.

In some related embodiments, the first component further comprises an extended-release subcomponent, wherein the extended-release subcomponent comprises an active ingredient comprising one or more agents selected from the group consisting of analgesic agents, α-blockers and 5α-reductase inhibitors. In some embodiments, the one or more agents comprise an analgesic agent selected from the group consisting of aspirin, ibuprofen, naproxen, naproxen sodium, indomethacin, nabumetone, and acetaminophen.

In some embodiments, the immediate-release subcomponent and the extended-release subcomponent in the second component each comprises tamsulosin. In some related embodiments, the immediate-release subcomponent and the extended-release subcomponent in the second component each comprises finasteride. In some related embodiments, the immediate-release subcomponent and the extended-release subcomponent in the second component each comprises tamsulosin and finasteride.

In some related embodiments, at least one of the active ingredients in the immediate-release subcomponent and/or the extended-release subcomponent of the first and the second components further comprises an agent selected from the group consisting of antimuscarinic agents, antidiuretic agents and spasmolytics.

In some related embodiments, the active ingredient in the immediate-release subcomponent and/or the extended-release subcomponent of the first component further comprises an agent selected from the group consisting of antimuscarinic agents, antidiuretic agents and spasmolytics.

In some related embodiments, the active ingredient in the immediate-release subcomponent and/or the extended-release subcomponent of the second component further comprises an agent selected from the group consisting of antimuscarinic agents, antidiuretic agents and spasmolytics.

Another aspect of the present application relates to a pharmaceutical composition the comprises a first component comprising an immediate-release subcomponent and an extended-release subcomponent, wherein the first component is formulated to release the subcomponents immediately after administration; and a second component comprising an immediate-release subcomponent and an extended-release subcomponent, wherein the second component is formulated for a delayed-release of the subcomponents, wherein the immediate-release subcomponent and the extended-release subcomponent in the first component each comprises an active ingredient comprising (1) one or more analgesic agents, and (2) an α-blocker, a 5α-reductase inhibitor or both, and wherein the immediate-release subcomponent and the extended-release subcomponent in the second component each comprises an active ingredient comprising (1) one or more analgesic agents, and (2) an α-blocker, a 5α-reductase inhibitor or both, wherein the pharmaceutical composition reduces the frequency of urination in patients in need thereof. In some embodiments, the one or more analgesic agents are selected from the group consisting of aspirin, ibuprofen, naproxen, naproxen sodium, indomethacin, nabumetone, and acetaminophen. In some embodiments, the one or more analgesic agents comprise acetaminophen, the α-blocker is tamsulosin and the 5α-reductase inhibitor is finasteride.

In other embodiments, the pharmaceutical composition comprises a pair of analgesic agents. Examples of such paired analgesic agents include, but are not limited to, acetaminophen and an NSAID, acetylsalicylic acid and ibuprofen, acetylsalicylic acid and naproxen sodium, acetylsalicylic acid and nabumetone, acetylsalicylic acid and acetaminophen, acetylsalicylic acid and indomethancin, ibuprofen and naproxen sodium, ibuprofen and nabumetone, ibuprofen and acetaminophen, ibuprofen and indomethancin, naproxen sodium and nabumetone, naproxen sodium and acetaminophen, naproxen sodium and indomethancin, nabumetone and acetaminophen, nabumetone and indomethancin, and acetaminophen and indomethancin. The paired analgesic agents are mixed at a weight ratio in the range of 0.1:1 to 10:1, 0.2:1 to 5:1 or 0.3:1 to 3:1 with a combined dose or single dose (i.e., the dose for each analgesic) in the range of 5 mg to 2000 mg, 20 mg to 2000 mg, 100 mg to 2000 mg, 200 mg to 2000 mg, 500 mg to 2000 mg, 5 mg to 1500 mg, 20 mg to 1500 mg, 100 mg to 1500 mg, 200 mg to 1500 mg, 500 mg to 1500 mg, 5 mg to 1000 mg, 20 mg to 1000 mg, 100 mg to 1000 mg, 250 mg to 500 mg, 250 mg to 1000 mg, 250 mg to 1500 mg, 500 mg to 1000 mg, 500 mg to 1500 mg, 1000 mg to 1500 mg, and 1000 mg to 2000 mg. In one embodiment, the paired analgesic agents are mixed at a weight ratio of 1:1.

Another aspect of the present application relates to a pharmaceutical composition that comprises an immediate-release component and an extended-release component. Each component comprises a pair of analgesic agents as described above and at least one of the components comprises an agent selected from the group consisting of α-blockers and 5α-reductase inhibitors. In some embodiments, the immediate-release component and the extended-release component comprise different pairs of analgesic agents. In some embodiments, the immediate-release component and the extended-release component comprise the same pair of analgesic agents. In some embodiments, the immediate-release component and the extended-release component each comprises acetaminophen and an NSAID. In some embodiments, the immediate-release component and the extended-release component each comprises acetaminophen and ibuprofen. In some embodiments, the immediate-release component and the extended-release component each consists of acetaminophen, ibuprofen and an agent selected from the group consisting of α-blockers and 5α-reductase inhibitors. In some embodiments, the agent is tamsulosin. In other embodiments, the agent is finasteride.

In some embodiments, the extended-release component is formulated for extended release over a period of 0.5-24, 2-6, 6-10, 10-14 or 14-18 hours. In some embodiments, the extended-release component is formulated for extended release over a period of about 8 hours. In some embodiments, the extended-release component is coated with a delayed-release coating. In some embodiments, the delayed-release coating delays the release of the extended-release component for a period of 0.1-12, 0.5-12, 1-12, 1-4, 2-4, 4-8 or 8-12 hours. In some embodiments, the delayed-release coating is an enteric coating. In some embodiment, the pharmaceutical composition with an immediate-release component and an extended-release component is formulated into an orally disintegrating tablet.

As used herein, the term "orally disintegrating tablet" or "orally disintegrating formulation" refers to drug tablet or formulation that rapidly disintegrates or dissolves in the oral cavity. Orally disintegrating formulations differ from traditional tablets in that they are designed to be dissolved on the tongue rather than swallowed whole. In some embodiments, the orally disintegrating formulations are designed to completely disintegrate or dissolve in the oral cavity without the aid of additional water (i.e., in saliva only) in 5, 10, 20, 30, 60, 90, 120, 180, 240 or 300 seconds.

In some embodiment, the pharmaceutical composition with an immediate-release component and an extended-release component is formulated into a liquid form for oral administration. Examples of the liquid form formulation include, but are not limited to, gels, emulsions and particle suspensions. For example, the extended-release component may be formulated into a gel form that solidified in stomach. In some embodiment, the pharmaceutical composition with an immediate-release component and an extended-release component is formulated into a pixie pack of powder that can quickly melt on the tongue. In some embodiments, the immediate-release component or the extended release component or both further comprise one or more additional agents selected from the group consisting of antimuscarinic agents, spasmolytics and antidiuretic agents.

Method of Manufacture

Another aspect of the present application relates to methods of manufacturing extended-release pharmaceutical compositions for reducing the frequency of urination. In some embodiments, the method comprises the steps of forming a first mixture having a first active ingredient formulated for immediate release and a second active ingredient formulated for extended release; coating the first mixture with a delayed release coating to form a core structure; and then coating the core structure with a second mixture comprising a third active ingredient formulated for immediate release and a fourth active ingredient formulated for extended release. In one embodiment, at least one of the first, second, third and fourth active ingredients comprises an analgesic agent and at least one of the first, second, third and fourth active ingredients comprises an α-blocker, a 5α-reductase inhibitor or both.

In some embodiments, the analgesic agent is selected from the group consisting of aspirin, ibuprofen, naproxen, naproxen sodium, indomethacin, nabumetone and acetaminophen, and wherein at least one of the first, second, third and fourth active ingredients comprises 5 mg to 2000 mg of the analgesic agent.

In some embodiments, at least one of the first, second, third and fourth active ingredients comprises (1) an analgesic agent selected from the group consisting of aspirin, ibuprofen, naproxen, naproxen sodium, indomethacin, nabumetone, and acetaminophen, and (2) an α-blocker. In some embodiments, the analgesic agent is acetaminophen and the α-blocker is tamsulosin.

In some embodiments, the at least one of the first, second, third and fourth active ingredients comprises (1) an analgesic agent selected from the group consisting of aspirin, ibuprofen, naproxen, naproxen sodium, indomethacin, nabumetone, and acetaminophen, and (2) an 5α-reductase inhibitor. In some embodiments, the analgesic agent is acetaminophen and the 5α-reductase inhibitor is finasteride.

In some embodiments, the at least one of the first, second, third and fourth active ingredients comprises (1) an analgesic agent selected from the group consisting of aspirin, ibuprofen, naproxen, naproxen sodium, indomethacin, nabumetone, and acetaminophen, (2) an α-blocker and (3) a 5α-reductase inhibitor.

In some embodiments, the at least one of the first, second, third and fourth active ingredients comprises an agent selected from the group consisting antimuscarinic agents, antidiuretic agents and spasmolytics.

In some embodiments, the delayed release coating is an enteric coating. In some embodiments, the enteric coating comprises a pH-dependent polymer.

In some embodiments, the delayed release coating comprises a swelling layer covered by an outer semi-permeable polymer layer.

In some embodiments, the delayed release coating is formulated to release the coated material after a lag time of 0.1-12 hours, 0.5-12 hours, 1-12 hours, 2-12 hours, 1-4 hours, 2-4 hours, 2-6 hours, 2-8 hours, 4-6 hours or 4-8 hours after oral administration.

In some embodiments, the second active ingredient, or the fourth active ingredient or both comprise an active core comprising an extended-release coating or a polymeric matrix effecting diffusion controlled release.

In some embodiments, the first mixture is prepared by mixing the first active ingredient in liquid or powder form with the second active ingredient, which is formulated for extended release. As described above, the second active ingredient may be formulated in an extended release formulation having an active core comprised of one or more inert particles, each in the form of a bead, pellet, pill, granular particle, microcapsule, microsphere, microgranule, nanocapsule, or nanosphere coated on its surfaces with drugs in the form of e.g., a drug-containing coating or film-forming composition using, for example, fluid bed techniques or other methodologies known to those of skill in the art. The inert particle can be of various sizes, so long as it is large enough to remain poorly dissolved. Alternatively, the active core may be prepared by granulating and milling and/or by extrusion and spheronization of a polymer composition containing the drug substance. In some embodiments, the active core comprises a extended-release coating or a polymeric matrix effecting diffusion controlled release, as described in more detail earlier. In some embodiments, the polymeric matrix is a water soluble or water-swellable matrix. In some embodiments, the second active ingredient is simply mixed with the first active ingredient. Either ingredient or both ingredients may be in the form of bead, pellet, granular particle, pill, microcapsule, microsphere, microgranule, nanocapsule or nanosphere as a powder or as a liquid suspension. In other embodiments, the second active ingredient forms an active core that is coated with the first active ingredient. In some embodiments, the second active ingredient in the first mixture is formulated to release the active ingredient over a period of 2-4 hours, 2-6 hours, 2-8 hours or 2-10 hours.

In some embodiments, the second active ingredient is kept in a compartment partially or completely separated from the first active ingredient. In other embodiments, the first mixture is formed by keeping the second active ingredient in a compartment partially or completely separated from the first active ingredient.

The first mixture is then coated with a delayed release coating to form a core structure. In some embodiments, the delayed release coating is an enteric coating. In some embodiments, the enteric coating comprises a pH-dependent polymer that maintains its structure integrity at low pH, such as the pH in the stomach (normally in the range of 1.5-3.5). In some embodiments, the term "low pH" refers to a pH value of 4.0, 3.5, 3.0, 2.5, 2.0, 1.5, 1.0 or lower. In some embodiments, the enteric coating comprises one or more pH-dependent polymers and one or more polysaccharides that are resistant to erosion in both the stomach and intestine, thus allowing the release of the first mixture only in colon. In some embodiment, the delayed release coating comprises two or more layers of coating. In some embodiment, the delayed release coating comprises a swelling layer and an outer semi-permeable polymer layer that covers the swelling layer.

In the next step, the coated core structure is re-coated with a second mixture that comprises a third active ingredient formulated for immediate release and a fourth active ingredient formulated for extended release. In some embodiments, the second mixture is prepared by mixing the third active ingredient in liquid or powder form with the fourth active ingredient, which is formulated for extended release. The fourth active ingredient may be formulated in an extended release formulation having an active core comprised of one or more inert particles, each in the form of a bead, pellet, pill, granular particle, microcapsule, microsphere, microgranule, nanocapsule, or nanosphere coated on its surfaces with drugs in the form of e.g., a drug-containing coating or film-forming composition using, for example, fluid bed techniques or other methodologies known to those of skill in the art. The inert particle can be of various sizes, so long as it is large enough to remain poorly dissolved. Alternatively, the active core may be prepared by granulating and milling and/or by extrusion and spheronization of a polymer composition containing the drug substance. In some embodiments, the active core comprises an extended-release coating or a polymeric matrix effecting diffusion controlled release, as described in more detail earlier. In some embodiments, the polymeric matrix is a water soluble or water-swellable matrix. In some embodiments, the fourth active ingredient is simply mixed with the third active ingredient. Either ingredient or both ingredients may be in the form of bead, pellet, granular particle, pill, microcapsule, microsphere, microgranule, nanocapsule or nanosphere as a powder or as a liquid suspension.

In other embodiments, the coated core structure is re-coated first with the fourth active ingredient, and then coated with the third active ingredient. In some embodiments, the fourth active ingredient is formulated to release the active ingredient over a period of 2-4 hours, 2-6 hours, 2-8 hours or 2-10 hours.

In some embodiments, the fourth active ingredient is kept in a compartment partially or completely separated from the third active ingredient. In other embodiments, the second mixture is formed by keeping the fourth active ingredient in a compartment partially or completely separated from the third active ingredient.

In other embodiments, the method comprises the steps of forming a core structure comprising a first active ingredient formulated for immediate release and a second active ingredient formulated for extended release, coating the core structure with a delayed release coating to form a coated core structure, and mixing the coated core structure with a third active ingredient formulated for immediate release and a fourth active ingredient formulated for extended release to form a final mixture. The first, second, third and fourth active ingredients can be the active ingredients described above. In one embodiment, the first, second, third and fourth active ingredients each comprises an analgesic agent. In some embodiments, the analgesic agent is selected from the group consisting of aspirin, ibuprofen, naproxen, naproxen sodium, indomethacin, nabumetone and acetaminophen. In some embodiments, the method further comprises the step of preparing a dosage form with the final mixture. In some embodiments, the dosage form is in a tablet form. In some embodiments, the dosage form is in an orally disintegrating form, e.g., orally disintegrating tablet form. In some embodiments, the dosage form is in a beads-in-a-capsule form. In some embodiments, the dosage form is in a liquid (e.g., emulsion) form.

In other embodiments, the method comprises the steps of forming a core structure comprising a first active ingredient formulated for immediate release and a second active ingredient formulated for extended release, coating the core structure with a delayed release coating to form a coated core structure, mixing the coated core structure with a third ingredient formulated for immediate release and a fourth ingredient formulated for extended release.

Another aspect of the present application relates to a method for manufacturing a pharmaceutical composition for reducing the frequency of urination. The method comprises the step of forming a core structure comprising a first active ingredient formulated for immediate release and a second active ingredient formulated for extended release; coating the core structure with a delayed release coating to form a coated core structure; mixing the coated core structure with a third active ingredient formulated for immediate release and a fourth active ingredient formulated for extended release to form a final mixture, and compressing the final mixture into a tablet. In some embodiments, at least one of the first, second, third and fourth active ingredients comprises an analgesic agent and at least one of the first, second, third and fourth active ingredients comprises an α-blocker, a 5α-reductase inhibitor or both.

In some embodiments, the analgesic agent is selected from the group consisting of aspirin, ibuprofen, naproxen, naproxen sodium, indomethacin, nabumetone and acetaminophen and wherein at least one of the first, second, third and fourth active ingredients comprises 5-2000 mg of the analgesic agent.

In some embodiments, the at least one of the first, second, third and fourth active ingredients comprises: (1) acetaminophen; and (2) an α-blocker, a 5α-reductase inhibitor or both.

In some embodiments, the at least one of the first, second, third and fourth active ingredients comprises an agent selected from the group consisting antimuscarinic agents, antidiuretic agents and spasmolytics.

Another aspect of the present application relates to a method for manufacturing a pharmaceutical composition for reducing the frequency of urination. The method comprises the steps of forming a core structure comprising a first active ingredient formulated for immediate release and a second active ingredient formulated for extended release; coating the core structure with a delayed release coating to form a coated core structure; coating the coated core structure with a third active ingredient formulated for immediate release to form a double-coated core structure. In some embodiments, wherein at least one of the first, second and third active ingredients comprises an analgesic agent and at least one of the first, second and third active ingredients comprises an α-blocker, a 5α-reductase inhibitor or both.

In some embodiments, the analgesic agent is selected from the group consisting of aspirin, ibuprofen, naproxen, naproxen sodium, indomethacin, nabumetone and acetaminophen and wherein at least one of the first, second and third active ingredients comprises 5-2000 mg of the analgesic agent.

In some embodiments, at least one of the first, second and third active ingredients comprises: (1) acetaminophen; and (2) an α-blocker, a 5α-reductase inhibitor or both.

In some embodiments, the at least one of the first, second and third active ingredients comprises an agent selected from the group consisting antimuscarinic agents, antidiuretic agents and spasmolytics.

Another aspect of the present application relates to a method for manufacturing a pharmaceutical composition for reducing the frequency of urination. The method comprises the steps of forming a core structure comprising a first pair of analgesic agents formulated for extended-release, and coating the core structure with a coating layer comprising a second pair of analgesics, wherein the second pair of analgesics is formulated for immediate release and wherein either the core structure or the coating layer or both further comprise an agent selected from the group consisting of α-blockers and 5α-reductase inhibitors.

In some embodiments, the core structure is first coated with a delayed-release coating and then coated with a coating layer comprising a second pair of analgesics, wherein the second pair of analgesics is formulated for immediate release.

In some embodiments, the method comprises the steps of forming a first mixture comprising a first pair of analgesic agents formulated for extended-release, forming a second mixture comprising a second pair of analgesic agents formulated for immediate-release, and combining the first mixture and the second mixture to form a final mixture, wherein either the first mixture or the second mixture or both further comprise an agent selected from the group consisting of α-blockers and 5α-reductase inhibitors.

In some embodiments, the first mixture, the second mixture and the final mixture are mixtures of solid materials. In some embodiments, the final mixture is in a powder or granulate form. In some embodiments, the method further comprises the step of pressing the final mixture into a tablet form. In some embodiments, the final mixture is in a liquid, gel or emulsion form.

Examples of paired analgesic agents include, but are not limited to, acetaminophen and an NSAID, acetylsalicylic acid and ibuprofen, acetylsalicylic acid and naproxen sodium, acetylsalicylic acid and nabumetone, acetylsalicylic acid and acetaminophen, acetylsalicylic acid and indomethancin, ibuprofen and naproxen sodium, ibuprofen and nabumetone, ibuprofen and acetaminophen, ibuprofen and indomethancin, naproxen sodium and nabumetone, naproxen sodium and acetaminophen, naproxen sodium and indomethancin, nabumetone and acetaminophen, nabumetone and indomethancin, and acetaminophen and indomethancin. In some embodiments, the first pair of analgesic agents is different from the second pair of analgesic agents. In other embodiments, the first pair of analgesic agents is the same as the second pair of analgesic agents. In one embodiment, the first pair of analgesic agents and the second pair of analgesic agents are both acetaminophen and ibuprofen.

For example, the extended-release component may be formulated into a gel form that solidified in stomach. In some embodiment, the pharmaceutical composition with an immediate-release component and an extended-release component is formulated into a pixie pack of powder that can quickly melt on the tongue. In some embodiments, the pharmaceutical composition with an immediate-release component and an extended-release component is formulated into an orally disintegrating tablet using loose compression tableting. In loose compression, orally disintegrating formulation is compressed at much lower forces (4-20 kN) than traditional tablets. In some embodiments, the orally disintegrating formulation contains some form of sugar, such as mannitol, to improve mouth feel. In some embodiments, the orally disintegrating tablet is produced using lyophilized orally disintegrating formulation.

The present invention is further illustrated by the following example which should not be construed as limiting. The contents of all references, patents and published patent applications cited throughout this application are incorporated herein by reference.

Example 1: Inhibition of the Urge to Urinate

Twenty volunteer subjects, both male and female were enrolled, each of which experienced premature urge or desire to urinate, interfering with their ability to sleep for a sufficient period of time to feel adequately rested. Each subject ingested 400-800 mg of ibuprofen as a single dose prior to bedtime. At least 14 subjects reported that they were able to rest better because they were not being awakened as frequently by the urge to urinate.

Several subjects reported that after several weeks of nightly use of ibuprofen, the benefit of less frequent urges to urinate was no longer being realized. However, all of these subjects further reported the return of the benefit after several days of abstaining from taking the dosages.

Example 2: Effect of Analgesic Agents, Botulinum Neurotoxin and Antimuscarinic Agents on Macrophage Responses to Inflammatory and Non-Inflammatory Stimuli Experimental Design This study is designed to determine the dose and in vitro efficacy of analgesics and antimuscarinic agents in controlling macrophage response to inflammatory and non-inflammatory stimuli mediated by COX1 and/or COX2 and prostaglandins (PGE, PGH, etc.). It establishes baseline (dose and kinetic) responses to inflammatory and non-inflammatory effectors in bladder cells. Briefly, cultured cells are exposed to analgesic agents and/or antimuscarinic agents in the absence or presence of various effectors.

The effectors include: lipopolysaccharide (LPS), an inflammatory agent and COX1/2 inducer, as inflammatory stimuli; carbachol or acetylcholine, a stimulator of smooth muscle contraction, as non-inflammatory stimuli; botulinum neurotoxin A, a known inhibitor of acetylcholine release, as positive control; and arachidonic acid (AA), gamma linolenic acid (DGLA) or eicosapentaenoic acid (EPA) as precursors of prostaglandins, which are produced following the sequential oxidation of AA, DGLA or EPA inside the cell by cyclooxygenases (COX1 and COX2) and terminal prostaglandin synthases.

The analgesic agents include: Salicylates such as aspirin, iso-butyl-propanoic-phenolic acid derivative (ibuprofen) such as Advil, Motrin, Nuprin, and Medipren, naproxen sodium such as Aleve, Anaprox, Antalgin, Feminax Ultra, Flanax, Inza, Midol Extended Relief, Nalgesin, Naposin, Naprelan, Naprogesic, Naprosyn, Naprosyn suspension, EC-Naprosyn, Narocin, Proxen, Synflex and Xenobid, acetic acid derivative such as indomethacin (Indocin), 1-naphthaleneacetic acid derivative such as nabumetone or relafen, N-acetyl-para-aminophenol (APAP) derivative such as acetaminophen or paracetamol (Tylenol) and Celecoxib.

The antimuscarinic agents include: oxybutynin, solifenacin, darifenacin and atropine.

Macrophages are subjected to short term (1-2 hrs) or long term (24-48 hrs) stimulation with:

1) Each analgesic agent alone at various doses.

(2) Each analgesic agent at various doses in the presence of LPS.

(3) Each analgesic agent at various doses in the presence of carbachol or acetylcholine.

(4) Each analgesic agent at various doses in the presence of AA, DGLA, or EPA.

(5) Botulinum neurotoxin A alone at various doses.

(6) Botulinum neurotoxin A at various doses in the presence of LPS.

(7) Botulinum neurotoxin A at various doses in the presence of carbachol or acetylcholine.

(8) Botulinum neurotoxin A at various doses in the presence of AA, DGLA, or EPA.

(9) Each antimuscarinic agent alone at various doses.

(10) Each antimuscarinic agent at various doses in the presence of LPS.

(11) Each antimuscarinic agent at various doses in the presence of carbachol or acetylcholine.

(12) Each antimuscarinic agent at various doses in the presence of AA, DGLA, or EPA.

The cells are then analyzed for the release of $PGH_2$, PGE, $PGE_2$, Prostacydin, Thromboxane, IL-1β, IL-6, TNF-α, the COX2 activity, the production of cAMP and cGMP, the production of IL-1β, IL-6, TNF-α and COX2 mRNA, and surface expression of CD80, CD86 and MHC class II molecules.

Materials and Methods

Macrophage Cells

Murine RAW264.7 or J774 macrophage cells (obtained from ATCC) were used in this study. Cells were maintained in a culture medium containing RPMI 1640 supplemented with 10% fetal bovine serum (FBS), 15 mM HEPES, 2 mM L-glutamine, 100 U/ml penicillin, and 100 μg/ml of streptomycin. Cells were cultured at 37° C. in a 5% $CO_2$ atmosphere and split (passages) once a week.

In Vitro Treatment of Macrophage Cells with Analgesics

RAW264.7 macrophage cells were seeded in 96-well plates at a cell density of $1.5\times10^5$ cells per well in 100 μl of the culture medium. The cells were treated with (1) various concentrations of analgesic (acetaminophen, aspirin, ibuprofen or naproxen), (2) various concentrations of lipopolysaccharide (LPS), which is an effector of inflammatory stimuli to macrophage cells, (3) various concentrations of carbachol or acetylcholine, which are effectors of non-inflammatory stimuli, (4) analgesic and LPS or (5) analgesic and carbachol or acetylcholine. Briefly, the analgesics were dissolved in FBS-free culture medium (i.e., RPMI 1640 supplemented with 15 mM HEPES, 2 mM L-glutamine, 100 U/ml penicillin, and 100 μg/ml of streptomycin), and diluted to desired concentrations by serial dilution with the same medium. For cells treated with analgesic in the absence of LPS, 50 μl of analgesic solution and 50 μl of FBS-free culture medium were added to each well. For cells treated with analgesic in the presence of LPS, 50 μl of analgesic solution and 50 μl of LPS (from *Salmonella typhimurium*) in FBS-free culture medium were added to each well. All conditions were tested in duplicates.

After 24 or 48 hours of culture, 150 μl of culture supernatants were collected, spun down for 2 min at 8,000 rpm at 4° C. to remove cells and debris and stored at −70° C. for analysis of cytokine responses by ELISA. The cells were collected and washed by centrifugation (5 min at 1,500 rpm at 4° C.) in 500 μl of Phosphate buffer (PBS). Half of the cells were then snap frozen in liquid nitrogen and stored at −70° C. The remaining cells were stained with fluorescent monoclonal antibodies and analyzed by flow cytometry.

Flow Cytometry Analysis of Co-Stimulatory Molecule Expression

For flow cytometry analysis, macrophages were diluted in 100 µl of FACS buffer (phosphate buffered saline (PBS) with 2% bovine serum albumin (BSA) and 0.01% $NaN_3$) and stained 30 min at 4° C. by addition of FITC-conjugated anti-CD40, PE-conjugated anti-CD80, PE-conjugated anti-CD86 antibody, anti MHC class II (I-A$^d$) PE (BD Bioscience). Cells were then washed by centrifugation (5 min at 1,500 rpm at 4° C.) in 300 µl of FACS buffer. After a second wash, cells were re-suspended in 200 µl of FACS buffer and the percentage of cells expressing a given marker (single positive), or a combination of markers (double positive) were analyzed with the aid of an Accuri C6 flow cytometer (BD Biosciences).

Analysis of Cytokine Responses by ELISA

Culture supernatants were subjected to cytokine-specific ELISA to determine IL-1β, IL-6 and TNF-α responses in cultures of macrophages treated with analgesic, LPS alone or a combination of LPS and analgesic. The assays were performed on Nunc MaxiSorp Immunoplates (Nunc) coated overnight with 100 µl of anti-mouse IL-6, TNF-α mAbs (BD Biosciences) or IL-1β mAb (R&D Systems) in 0.1 M sodium bicarbonate buffer (pH 9.5). After two washes with PBS (200 µl per well), 200 µl of PBS 3% BSA were added in each well (blocking) and the plates incubated for 2 hours at room temperature. Plates were washed again two times by addition of 200 µl per well, 100 µl of cytokine standards and serial dilutions of culture supernatants were added in duplicate and the plates were incubated overnight at 4° C. Finally, the plates were washed twice and incubated with 100 µl of secondary biotinylated anti-mouse IL-6, TNFα mAbs (BD Biosciences) or IL-1β (R&D Systems) followed by peroxidase-labelled goat anti-biotin mAb (Vector Laboratories). The colorimetric reaction was developed by the addition of 2,2'-azino-bis(3)-ethylbenzylthiazoline-6-sulfonic acid (ABTS) substrate and $H_2O_2$ (Sigma) and the absorbance measured at 415 nm with a Victor® V multilabel plate reader (PerkinElmer).

Determination of COX2 Activity and the Production of cAMP and cGMP

The COX2 activity in the cultured macrophages is determined by sequential competitive ELISA (R&D Systems). The production of cAMP and cGMP is determined by the cAMP assay and cGMP assay. These assays are performed routinely in the art.

Results

Table 1 summarizes the experiments performed with Raw 264 macrophage cell line and main findings in terms of the effects of analgesics on cell surface expression of costimulatory molecules CD40 and CD80. Expression of these molecules is stimulated by COX1/2 and inflammatory signals and thus, was evaluated to determine functional consequences of inhibition of COX1/2.

Figure 1B:
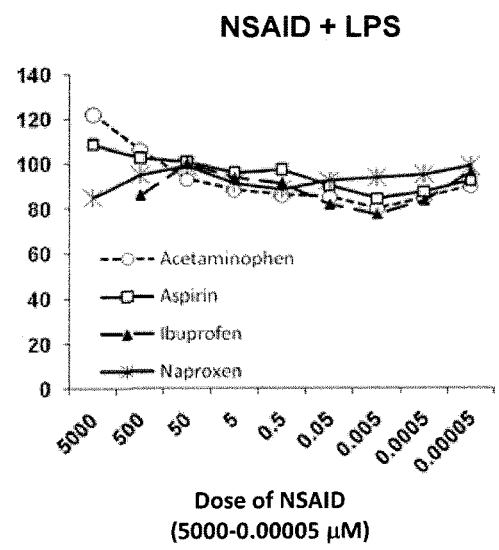

As shown in Table 2, acetaminophen, aspirin, ibuprofen and naproxen inhibit basal expression of co-stimulatory molecules CD40 and CD80 by macrophages at all the tested doses (i.e., $5×10^5$ nM, $5×10^4$ nM, $5×10^3$ nM, $5×10^2$ nM, 50 nM and 5 nM), except for the highest dose (i.e., $5×10^6$ nM), which appears to enhance, rather than inhibit, expression of the co-stimulatory molecules. As shown in FIGS. 1A and 1B, such inhibitory effect on CD40 and CD50 expression was observed at analgesic doses as low as 0.05 nM (i.e., 0.00005 µM). This finding supports the notion that a controlled release of small doses of analgesic may be preferable to acute delivery of large doses. The experiment also revealed that acetaminophen, aspirin, ibuprofen and naproxen have a similar inhibitory effect on LPS induced expression of CD40 and CD80.

TABLE 1

Summary of experiments

| | | LPS *Salmonella* | | | | |
|---|---|---|---|---|---|---|
| | Control | *typhimurium* | Acetaminophen | Aspirin | Ibuprophen | Naproxen |
| TESTS | | | | | | |
| 1 | X | | | | | |
| 2 | X | Dose responses (0, 5, 50, 1000) ng/mL | | | | |
| 3 | X | | Dose responses (0, 5, 50, 500, $5 × 10^3$, $5 × 10^4$, $5 × 10^5$, $5 × 10^6$) nM | | | |
| 4 | X | X (5 ng/mL) X (50 ng/mL) X (1000 ng/mL) | Dose responses (0, 5, 50, 500, $5 × 10^3$, $5 × 10^4$, $5 × 10^5$, $5 × 10^6$) nM | | | |
| ANALYSIS | | | | | | |
| a | | Characterization of activation/stimulatory status: Flow cytometry analysis of CD40, CD80, CD86 and MHC class II | | | | |
| b | | Mediators of inflammatory responses: ELISA analysis of IL-1β, IL-6, TNF-α | | | | |

TABLE 2

Summary of main findings

| Effectors | % Positive | Negative Control | LPS 5 ng/ml | $5 \times 10^6$ | $5 \times 10^5$ | $5 \times 10^4$ | $5 \times 10^3$ | 500 | 50 | 5 |
|---|---|---|---|---|---|---|---|---|---|---|
| | | | | Dose analgesic (nM) | | | | | | |
| | CD40+CD80+ | 20.6 | 77.8 | | | | | | | |
| | CD40+CD80+ | 20.6 | 77.8 | | | | | | | |
| Acetaminophen | CD40+CD80+ | | | 63 | 18 | 12 | 9.8 | 8.3 | 9.5 | 7.5 |
| Aspirin | CD40+CD80+ | | | 44 | 11 | 10.3 | 8.3 | 8 | 10.5 | 7.5 |
| Ibuprophen | CD40+CD80+ | | | ND* | 6.4 | 7.7 | 7.9 | 6.0 | 4.9 | 5.8 |
| Naproxen | CD40+CD80+ | | | 37 | 9.6 | 7.7 | 6.9 | 7.2 | 6.8 | 5.2 |
| | | | | Analgesic plus LPS | | | | | | |
| Acetaminophen | CD40+CD80+ | | | 95.1 | 82.7 | 72.4 | 68.8 | 66.8 | 66.2 | 62.1 |
| Aspirin | CD40+CD80+ | | | 84.5 | 80 | 78.7 | 74.7 | 75.8 | 70.1 | 65.7 |
| Ibuprophen | CD40+CD80+ | | | ND | 67 | 77.9 | 72.9 | 71.1 | 63.7 | 60.3 |
| Naproxen | CD40+CD80+ | | | 66.0 | 74.1 | 77.1 | 71.0 | 68.8 | 72 | 73 |

*ND: not done (toxicity)

Table 3 summarizes the results of several studies that measured serum levels of analgesic after oral therapeutic doses in adult humans. As shown in Table 3, the maximum serum levels of analgesic after an oral therapeutic dose are in the range of $10^4$ to $10^5$ nM. Therefore, the doses of analgesic tested in vitro in Table 2 cover the range of concentrations achievable in vivo in humans.

TABLE 3

Serum levels of analgesic in human blood after oral therapeutic doses

| Analgesic drug | Molecular weight | Maximum serum levels after oral therapeutic doses | | References |
|---|---|---|---|---|
| | | mg/L | nM | |
| Acetaminophen (Tylenol) | 151.16 | 11-18 | $7.2 \times 10^4$- $1.19 \times 10^5$ | BMC Clinical Pharmacology. 2010, 10: 10 Anaesth Intensive Care. 2011, 39: 242 |
| Aspirin (Acetylsalicylic acid) | 181.66 | 30-100 | $1.65 \times 10^5$- $5.5 \times 10^5$ | Disposition of Toxic Drugs and Chemicals in Man, 8th Edition, Biomedical Public, Foster City, CA, 2008, pp. 22-25 J Lab Clin Med. 1984 June; 103: 869 |
| Ibuprofen (Advil, Motrin) | 206.29 | 24-32 | $1.16 \times 10^5$- $1.55 \times 10^5$ | BMC Clinical Pharmacology 2010, 10: 10 J Clin Pharmacol. 2001, 41: 330 |
| Naproxen (Aleve) | 230.26 | Up to 60 | Up to $2.6 \times 10^5$ | J Clin Pharmacol. 2001, 41: 330 |

Example 3: Effect of Analgesic Agents, Botulinum Neurotoxin and Antimuscarinic Agents on Mouse Bladder Smooth Muscle Cell Responses to Inflammatory and Non-Inflammatory Stimuli Experimental Design This study is designed to characterize how the optimal doses of analgesics determined in Example 2 affect bladder smooth muscle cells in cell culture or tissue cultures, and to address whether different classes of analgesics can synergize to more efficiently inhibit COX2 and PGE2 responses.

The effectors, analgesic agents and antimuscarinic agents are described in Example 2.

Primary culture of mouse bladder smooth muscle cells are subjected to short term (1-2 hrs) or long term (24-48 hrs) stimulation with:

(1) Each analgesic agent alone at various doses.

(2) Each analgesic agent at various doses in the presence of LPS.

(3) Each analgesic agent at various doses in the presence of carbachol or acetylcholine.

(4) Each analgesic agent at various doses in the presence of AA, DGLA, or EPA.

(5) Botulinum neurotoxin A alone at various doses.

(6) Botulinum neurotoxin A at various doses in the presence of LPS.

(7) Botulinum neurotoxin A at various doses in the presence of carbachol or acetylcholine.

(8) Botulinum neurotoxin A at various doses in the presence of AA, DGLA, or EPA.

(9) Each antimuscarinic agent alone at various doses.

(10) Each antimuscarinic agent at various doses in the presence of LPS.

(11) Each antimuscarinic agent at various doses in the presence of carbachol or acetylcholine.

(12) Each antimuscarinic agent at various doses in the presence of AA, DGLA, or EPA.

The cells are then analyzed for the release of $PGH_2$, PGE, $PGE_2$, Prostacydin, Thromboxane, IL-1β, IL-6, TNF-α, the COX2 activity, the production of cAMP and cGMP, the production of IL-1β, IL-6, TNF-α and COX2 mRNA, and surface expression of CD80, CD86 and MHC class II molecules.

Materials and Methods

Isolation and Purification of Mouse Bladder Cells

Bladder cells were removed from euthanized animals C57BL/6 mice (8-12 weeks old) and cells were isolated by enzymatic digestion followed by purification on a Percoll gradient. Briefly, bladders from 10 mice were minced with scissors to fine slurry in 10 ml of digestion buffer (RPMI 1640, 2% fetal bovine serum, 0.5 mg/ml collagenase, 30 µg/ml DNase). Bladder slurries were enzymatically digested for 30 minutes at 37° C. Undigested fragments were further dispersed through a cell-trainer. The cell suspension was pelleted and added to a discontinue 20%, 40% and 75% Percoll gradient for purification on mononuclear cells. Each experiment used 50-60 bladders.

After washes in RPMI 1640, bladder cells were resuspended RPMI 1640 supplemented with 10% fetal bovine serum, 15 mM HEPES, 2 mM L-glutamine, 100 U/ml penicillin, and 100 µg/ml of streptomycin and seeded in clear-bottom black 96-well cell culture microculture plates at a cell density of $3 \times 10^4$ cells per well in 100 µl. Cells were cultured at 37° C. in a 5% $CO_2$ atmosphere.

In Vitro Treatment of Cells with Analgesics

Bladder cells were treated with analgesic solutions (50 well) either alone or together with carbachol (10-Molar, 50 µl/well), as an example of non-inflammatory stimuli, or lipopolysaccharide (LPS) of *Salmonella typhimurium* (1 µg/ml, 50 µl/well), as an example of non-inflammatory stimuli. When no other effectors were added to the cells, 50 µl of RPMI 1640 without fetal bovine serum were added to the wells to adjust the final volume to 200 µl.

After 24 hours of culture, 150 µl of culture supernatants were collected, spun down for 2 min at 8,000 rpm at 4° C. to remove cells and debris and stored at −70° C. for analysis of Prostaglandin E2 ($PGE_2$) responses by ELISA. Cells were fixed, permeabilized and blocked for detection of Cyclooxygenase-2 (COX2) using a fluorogenic substrate. In selected experiment cells were stimulated 12 hours in vitro for analysis of COX2 responses Analysis of COX2 Responses COX2 responses were analyzed by a Cell-Based ELISA using Human/mouse total COX2 immunoassay (R&D Systems), following the instructions of the manufacturer. Briefly, after cells fixation and permeabilization, a mouse anti-total COX2 and a rabbit anti-total GAPDH were added to the wells of the clear-bottom black 96-well cell culture microculture plates. After incubation and washes, an HRP-conjugated anti-mouse IgG and an AP-conjugated anti-rabbit IgG were added to the wells. Following another incubation and set of washes, the HRP- and AP-fluorogenic substrates were added. Finally, a Victor® V multilabel plate reader (PerkinElmer) was used to read the fluorescence emitted at 600 nm (COX2 fluorescence) and 450 nm (GAPDH fluorescence). Results are expressed as relative levels of total COX2 as determined by relative fluorescence unit (RFUs) and normalized to the housekeeping protein GAPDH.

Analysis of PGE2 Responses

Prostaglandin E2 responses were analyzed by a sequential competitive ELISA (R&D Systems). More specifically, culture supernatants or PGE2 standards were added to the wells of a 96-well polystyrene microplate coated with a goat anti-mouse polyclonal antibody. After one hour incubation on a microplate shaker, an HRP-conjugated PGE2 was added and plates incubated for an additional two hours at room temperature. The plates were then washed and HRP substrate solution added to each well. The color was allowed to develop for 30 min and the reaction stopped by addition sulfuric acid before reading the plate at 450 nm with wavelength correction at 570 nm. Results are expressed as mean pg/ml of PGE2.

Other Assays

The release of $PGH_2$, PGE, Prostacydin, Thromboxane, IL-1β, IL-6, and TNF-α, the production of cAMP and cGMP, the production of IL-1β, IL-6, TNF-α and COX2 mRNA, and surface expression of CD80, CD86 and MHC class II molecules are determined as described in Example 2.

Analgesics Inhibit COX2 Responses of Mouse Bladder Cells to an Inflammatory Stimulus Several analgesics (acetaminophen, aspirin, ibuprofen and naproxen) were tested on mouse bladder cells at the concentration of 5 µM or 50 µM to determine whether the analgesics could induce COX2 responses. Analysis of 24-hour cultures showed that none of the analgesics tested induced COX2 responses in mouse bladder cells in vitro.

The effect of these analgesics on the COX2 responses of mouse bladder cells to carbachol or LPS stimulation in vitro was also tested. As indicated in Table 1, the dose of carbachol tested has no significant effect on COX2 levels in mouse bladder cells. On the other hand, LPS significantly increased total COX2 levels. Interestingly, acetaminophen, aspirin, ibuprofen and naproxen could all suppress the effect of LPS on COX2 levels. The suppressive effect of the analgesic was seen when these drugs were tested at either 5 µM or 50 µM (Table 4).

TABLE 4

COX2 expression by mouse bladder cells after in vitro stimulation and treatment with analgesic

| Stimulus | Analgesic | Total COX2 levels (Normalized RFUs) |
|---|---|---|
| None | None | 158 ± 18 |
| Carbachol (mM) | None | 149 ± 21 |
| LPS (1 µg/ml) | None | 420 ± 26 |
| LPS (1 µg/ml) | Acetaminophen (5 µM) | 275 ± 12 |
| LPS (1 µg/ml) | Aspirin (5 µM) | 240 ± 17 |
| LPS (1 µg/ml) | Ibuprofen (5 µM)) | 253 ± 32 |
| LPS (1 µg/ml) | Naproxen (5 µM) | 284 ± 11 |
| LPS (1 µg/ml) | Acetaminophen (50 µM) | 243 ± 15 |
| LPS (1 µg/ml) | Aspirin (50 µM) | 258 ± 21 |
| LPS (1 µg/ml) | Ibuprofen (50 µM) | 266 ± 19 |
| LPS (1 µg/ml) | Naproxen (50 µM) | 279 ± 23 |

Analgesics Inhibit PGE2 Responses of Mouse Bladder Cells to an Inflammatory Stimulus The secretion of PGE2 in culture supernatants of mouse bladder cells was measured to determine the biological significance of the alteration of mouse bladder cell COX2 levels by analgesics. As shown in Table 5, PGE2 was not detected in the culture supernatants of unstimulated bladder cells or bladder cells cultured in the presence of carbachol. Consistent with COX2 responses described above, stimulation of mouse bladder cells with LPS induced the secretion of high levels of PGE2. Addition of the analgesics acetaminophen, aspirin, ibuprofen and naproxen suppressed the effect of LPS on PGE2 secretion and no difference was seen between the responses of cells treated with the 5 or 50 µM dose of analgesic.

TABLE 5

PGE2 secretion by mouse bladder cells after in vitro stimulation and treatment with analgesic.

| Stimulus | Analgesic | PGE2 levels (pg/ml) |
|---|---|---|
| None | None | <20.5 |
| Carbachol (mM) | None | <20.5 |

TABLE 5-continued

PGE2 secretion by mouse bladder cells after in vitro stimulation and treatment with analgesic.

| Stimulus | Analgesic | PGE2 levels (pg/ml) |
|---|---|---|
| LPS (1 µg/ml) | None | 925 ± 55 |
| LPS (1 µg/ml) | Acetaminophen (5 µM) | 619 ± 32 |
| LPS (1 µg/ml) | Aspirin (5 µM) | 588 ± 21 |
| LPS (1 µg/ml) | Ibuprofen (5 µM)) | 593 ± 46 |
| LPS (1 µg/ml) | Naproxen (5 µM) | 597 ± 19 |
| LPS (1 µg/ml) | Acetaminophen (50 µM) | 600 ± 45 |
| LPS (1 µg/ml) | Aspirin (50 µM) | 571 ± 53 |
| LPS (1 µg/ml) | Ibuprofen (50 µM) | 568 ± 32 |
| LPS (1 µg/ml) | Naproxen (50 µM) | 588 ± 37 |

In summary, these data show that the analgesics alone at 5 µM or 50 µM do not induce COX2 and PGE2 responses in mouse bladder cells. The analgesics at 5 µM or 50 µM, however, significantly inhibit COX2 and PGE2 responses of mouse bladder cells stimulated in vitro with LPS (1 µg/ml). No significant effect of analgesics was observed on COX2 and PGE2 responses of mouse bladder cells stimulated with carbachol (1 mM).

Example 4: Effect of Analgesic Agents, Botulinum Neurotoxin and Antimuscarinic Agents on Mouse Bladder Smooth Muscle Cell Contraction Experimental Design Cultured mouse or rat bladder smooth muscle cells and mouse or rat bladder smooth muscle tissue are exposed to inflammatory stimuli and non-inflammatory stimuli in the presence of analgesic agent and/or antimuscarinic agent at various concentrations. The stimuli-induced muscle contraction is measured to evaluate the inhibitory effect of the analgesic agent and/or antimuscarinic agent.

The effectors, analgesic agents and antimuscarinic agents are described in Example 2.

Primary cultures of mouse bladder smooth muscle cells are subjected to short term (1-2 hrs) or long term (24-48 hrs) stimulation with:

(1) Each analgesic agent alone at various doses.
(2) Each analgesic agent at various doses in the presence of LPS.
(3) Each analgesic agent at various doses in the presence of carbachol or acetylcholine.
(4) Each analgesic agent at various doses in the presence of AA, DGLA, or EPA.
(5) Botulinum neurotoxin A alone at various doses.
(6) Botulinum neurotoxin A at various doses in the presence of LPS.
(7) Botulinum neurotoxin A at various doses in the presence of carbachol or acetylcholine.
(8) Botulinum neurotoxin A at various doses in the presence of AA, DGLA, or EPA.
(9) Each antimuscarinic agent alone at various doses.
(10) Each antimuscarinic agent at various doses in the presence of LPS.
(11) Each antimuscarinic agent at various doses in the presence of carbachol or acetylcholine.
(12) Each antimuscarinic agent at various doses in the presence of AA, DGLA, or EPA.

Materials and Methods

Primary mouse bladder cells are isolated as described in Example 3. In selected experiments, cultures of bladder tissue are used. Bladder smooth muscle cell contractions are recorded with a Grass polygraph (Quincy Mass., USA).

Example 5: Effect of Oral Analgesic Agents and Antimuscarinic Agents on COX2 and PGE2 Responses of Mouse Bladder Smooth Muscle Cells Experimental Design:

Normal mice and mice with over active bladder syndrome are given oral doses of aspirin, naproxen sodium, ibuprofen, Indocin, nabumetone, Tylenol, Celecoxib, oxybutynin, solifenacin, darifenacin, atropine and combinations thereof. Control groups include untreated normal mice and untreated OAB mice with over active bladder syndrome. Thirty (30) minutes after last doses, the bladders are collected and stimulated ex vivo with carbachol or acetylcholine. In selected experiments, the bladders are treated with botulinum neurotoxin A before stimulation with carbachol. Animals are maintained in metabolic cages and frequency (and volume) of urination are evaluated. Bladder outputs are determined by monitoring water intake and cage litter weight. Serum $PGH_2$, PGE, $PGE_2$, Prostacydin, Thromboxane, IL-1β, IL-6, TNF-α, cAMP, and cGMP levels are determined by ELISA. CD80, CD86, MHC class II expression in whole blood cells are determined by flow cytometry.

At the end of the experiment, animals are euthanized and ex vivo bladder contractions are recorded with a Grass polygraph. Portions of bladders are fixed in formalin, and COX2 responses are analyzed by immunohistochemistry.

Example 6: Effect of Analgesic Agents, Botulinum Neurotoxin and Antimuscarinic Agents on Human Bladder Smooth Muscle Cell Responses to Inflammatory and Non-Inflammatory Stimuli Experimental Design This study is designed to characterize how the optimal doses of analgesic determined in Examples 1-5 affect human bladder smooth muscle cells in cell culture or tissue cultures, and to address whether different classes of analgesics can synergize to more efficiently inhibit COX2 and PGE2 responses.

The effectors, analgesic agents and antimuscarinic agents are described in Example 2.

Human bladder smooth muscle cells are subjected to short term (1-2 hrs) or long term (24-48 hrs) stimulation with:

(1) Each analgesic agent alone at various doses.
(2) Each analgesic agent at various doses in the presence of LPS.
(3) Each analgesic agent at various doses in the presence of carbachol or acetylcholine.
(4) Each analgesic agent at various doses in the presence of AA, DGLA, or EPA.
(5) Botulinum neurotoxin A alone at various doses.
(6) Botulinum neurotoxin A at various doses in the presence of LPS.
(7) Botulinum neurotoxin A at various doses in the presence of carbachol or acetylcholine.
(8) Botulinum neurotoxin A at various doses in the presence of AA, DGLA, or EPA.
(9) Each antimuscarinic agent alone at various doses.
(10) Each antimuscarinic agent at various doses in the presence of LPS.
(11) Each antimuscarinic agent at various doses in the presence of carbachol or acetylcholine.
(12) Each antimuscarinic agent at various doses in the presence of AA, DGLA, or EPA.

The cells are then analyzed for the release of $PGH_2$, PGE, $PGE_2$, Prostacydin, Thromboxane, IL-1β, IL-6, TNF-α, the COX2 activity, the production of cAMP and cGMP, the production of IL-1β, IL-6, TNF-α and COX2 mRNA, and surface expression of CD80, CD86 and MHC class II molecules.

Example 7: Effect of Analgesic Agents, Botulinum Neurotoxin and Antimuscarinic Agents on Human Bladder Smooth Muscle Cell Contraction Experimental Design Cultured human bladder smooth muscle cells are exposed to inflammatory stimuli and non-inflammatory stimuli in the presence of an analgesic agent and/or antimuscarinic agent at various concentrations. The stimulus-induced muscle contraction is measured to evaluate the inhibitory effect of the analgesic agent and/or antimuscarinic agent.

The effectors, analgesic agents and antimuscarinic agents are described in Example 2.

Human bladder smooth muscle cells are subjected to short term (1-2 hrs) or long term (24-48 hrs) stimulation with:
  (1) Each analgesic agent alone at various doses.
  (2) Each analgesic agent at various doses in the presence of LPS.
  (3) Each analgesic agent at various doses in the presence of carbachol or acetylcholine.
  (4) Each analgesic agent at various doses in the presence of AA, DGLA, or EPA.
  (5) Botulinum neurotoxin A alone at various doses.
  (6) Botulinum neurotoxin A at various doses in the presence of LPS.
  (7) Botulinum neurotoxin A at various doses in the presence of carbachol or acetylcholine.
  (8) Botulinum neurotoxin A at various doses in the presence of AA, DGLA, or EPA.
  (9) Each antimuscarinic agent alone at various doses.
  (10) Each antimuscarinic agent at various doses in the presence of LPS.
  (11) Each antimuscarinic agent at various doses in the presence of carbachol or acetylcholine.
  (12) Each antimuscarinic agent at various doses in the presence of AA, DGLA, or EPA.

Bladder smooth muscle cell contractions are recorded with a Grass polygraph (Quincy Mass., USA).

Example 8: Effect of Analgesic Agents on Normal Human Bladder Smooth Muscle Cell Responses to Inflammatory and Non Inflammatory Signals Experimental Design
Culture of Normal Human Bladder Smooth Muscle Cells Normal human bladder smooth muscle cells were isolated by enzymatic digestion from macroscopically normal pieces of human bladder. Cells were expended in vitro by culture at 37° C. in a 5% $CO_2$ atmosphere in RPMI 1640 supplemented with 10% fetal bovine serum, 15 mM HEPES, 2 mM L-glutamine, 100 U/ml penicillin, and 100 mg/ml of streptomycin and passage once a week by treatment with trypsin to detach cells followed by reseeding in a new culture flask. The first week of culture, the culture medium was supplemented with 0.5 ng/ml epidermal growth factor, 2 ng/ml fibroblast growth factor, and 5 µg/ml insulin.
Treatment of Normal Human Bladder Smooth Muscle Cells with Analgesics In Vitro Bladder smooth muscle cells trypsinized and seeded in microculture plates at a cell density of $3 \times 10^4$ cells per well in 100 µl were treated with analgesic solutions (50 µl/well) either alone or together carbachol (10-Molar, 50 µl/well), as an example of non-inflammatory stimuli, or lipopolysaccharide (LPS) of *Salmonella typhimurium* (1 µg/ml, 50 µl/well), as an example of non-inflammatory stimuli. When no other effectors were added to the cells, 50 µl of RPMI 1640 without fetal bovine serum were added to the wells to adjust the final volume to 200 µl.

After 24 hours of culture, 150 µl of culture supernatants were collected, spun down for 2 min at 8,000 rpm at 4° C. to remove cells and debris and stored at −70° C. for analysis of Prostaglandin E2 ($PGE_2$) responses by ELISA. Cells were fixed, permeabilized and blocked for detection of COX2 using a fluorogenic substrate. In selected experiment cells were stimulated 12 hours in vitro for analysis of COX2, PGE2 and cytokine responses.
Analysis of COX2, PGE2 and Cytokine Responses COX2 and PGE2 responses were analyzed as described in Example 3. Cytokine responses were analyzed as described in Example 2.
Results Analgesics Inhibit COX2 Responses of Normal Human Bladder Smooth Muscle Cells to Inflammatory and Non-Inflammatory Stimuli—

Analysis of cells and culture supernatants after 24 hours of cultures showed that none of the analgesics tested alone induced COX2 responses in normal human bladder smooth muscle cells. However, as summarized in Table 6, carbachol induced low, but significant COX2 responses in normal human bladder smooth muscle cells. On the other hand, LPS treatment resulted in higher levels of COX2 responses in normal human bladder smooth muscle cells. Acetaminophen, aspirin, ibuprofen and naproxen could all suppress the effect of carbachol and LPS on COX2 levels. The suppressive effect of the analgesics was seen on LPS-induced responses when these drugs were tested at either 5 µM or 50 µM.

TABLE 6

COX2 expression by normal human bladder smooth muscle cells after in vitro stimulation with inflammatory and non- inflammatory stimuli and treatment with analgesic

| Stimulus | Analgesic | Total COX2 levels[#] (Normalized RFUs) subject 1 | Total COX2 levels (Normalized RFUs) subject 2 |
| --- | --- | --- | --- |
| None | None | 230 | 199 |
| Carbachol $10^{-3}$ M | None (50 µM) | 437 | 462 |
| Carbachol $10^{-3}$ M | Acetaminophen (50 µM) | 298 | 310 |
| Carbachol $10^{-3}$ M | Aspirin (50 µM) | 312 | 297 |
| Carbachol $10^{-3}$ M | Ibuprofen (50 µM) | 309 | 330 |
| Carbachol $10^{-3}$ M | Naproxen (50 µM) | 296 | 354 |
| LPS (10 µg/ml) | None | 672 | 633 |
| LPS (10 µg/ml) | Acetaminophen (5 µM) | 428 | 457 |
| LPS (10 µg/ml) | Aspirin (5 µM) | 472 | 491 |
| LPS (10 µg/ml) | Ibuprofen (5 µM) | 417 | 456 |
| LPS (10 µg/ml) | Naproxen (5 µM | 458 | 501 |
| LPS (10 µg/ml) | Acetaminophen (50 µM) | 399 | 509 |
| LPS (10 µg/ml) | Aspirin (50 µM) | 413 | 484 |
| LPS (10 µg/ml) | Ibuprofen (50 µM) | 427 | 466 |
| LPS (10 µg/ml) | Naproxen (50 µM) | 409 | 458 |

[#]Data are expressed as mean of duplicates

Analgesics Inhibit PGE2 Responses of Normal Human Bladder Smooth Muscle Cells to Inflammatory and Non-Inflammatory Stimuli—

Consistent with the induction of COX2 responses described above, both carbachol and LPS induced production of PGE2 by normal human bladder smooth muscle cells. Acetaminophen, aspirin, ibuprofen and naproxen were also found to suppress the LPS-induced PGE2 responses at either 5 µM or 50 µM (Table 7).

TABLE 7

PGE2 secretion by normal human bladder smooth muscle cells after in vitro stimulation with inflammatory and non-inflammatory stimuli and treatment with analgesic

| Stimulus | Analgesic | PGE2 levels[#] (pg/ml) Subject 1 | PGE2 levels (pg/ml) Subject 2 |
|---|---|---|---|
| None | None | <20.5 | <20.5 |
| Carbachol $10^{-3}$ M | None | 129 | 104 |
| Carbachol $10^{-3}$ M | Acetaminophen (50 µM) | 76 | 62 |
| Carbachol $10^{-3}$ M | Aspirin (50 µM) | 89 | 59 |
| Carbachol $10^{-3}$ M | Ibuprofen (50 µM) | 84 | 73 |
| Carbachol $10^{-3}$ M | Naproxen (50 µM) | 77 | 66 |
| LPS (10 µg/ml) | None | 1125 | 998 |
| LPS (10 µg/ml) | Acetaminophen (5 µM) | 817 | 542 |
| LPS (10 µg/ml) | Aspirin (5 µM) | 838 | 598 |
| LPS (10 µg/ml) | Ibuprofen (5 µM) | 824 | 527 |
| LPS (10 µg/ml) | Naproxen (5 µM | 859 | 506 |
| LPS (10 µg/ml) | Acetaminophen (50 µM) | 803 | 540 |
| LPS (10 µg/ml) | Aspirin (50 µM) | 812 | 534 |
| LPS (10 µg/ml) | Ibuprofen (50 µM) | 821 | 501 |
| LPS (10 µg/ml) | Naproxen (50 µM) | 819 | 523 |

[#]Data are expressed as mean of duplicates

Analgesics Inhibit Cytokine Responses of Normal Human Bladder Cells to Inflammatory Stimuli—

Analysis of cells and culture supernatants after 24 hours of culture showed that none of the analgesics tested alone induced IL-6 or TNFα secretion in normal human bladder smooth muscle cells. As shown in Tables 8 and 9, the doses of carbachol tested induced low, but significant TNFα and IL-6 responses in normal human bladder smooth muscle cells. On the other hand, LPS treatment resulted in massive induction of these proinflammatory cytokines. Acetaminophen, aspirin, ibuprofen and naproxen suppress the effect of carbachol and LPS on TNFα and IL-6 responses. The suppressive effect of the analgesics on LPS-induced responses was seen when these drugs were tested at either 5 µM or 50 µM.

TABLE 8

TNFα secretion by normal human bladder smooth muscle cells after in vitro stimulation with inflammatory and non-inflammatory stimuli and treatment with analgesic

| Stimulus | Analgesic | TNFα (pg/ml)[#] Subject 1 | TNFα (pg/ml) Subject 2 |
|---|---|---|---|
| None | None | <5 | <5 |
| Carbachol $10^{-3}$ M | None | 350 | 286 |
| Carbachol $10^{-3}$ M | Acetaminophen (50 µM) | 138 | 164 |
| Carbachol $10^{-3}$ M | Aspirin (50 µM) | 110 | 142 |
| Carbachol $10^{-3}$ M | Ibuprofen (50 µM) | 146 | 121 |
| Carbachol $10^{-3}$ M | Naproxen (50 µM) | 129 | 137 |
| LPS (10 µg/ml) | None | 5725 | 4107 |
| LPS (10 µg/ml) | Acetaminophen (5 µM) | 2338 | 2267 |
| LPS (10 µg/ml) | Aspirin (5 µM) | 2479 | 2187 |
| LPS (10 µg/ml) | Ibuprofen (5 µM) | 2733 | 2288 |
| LPS (10 µg/ml) | Naproxen (5 µM | 2591 | 2215 |
| LPS (10 µg/ml) | Acetaminophen (50 µM) | 2184 | 2056 |
| LPS (10 µg/ml) | Aspirin (50 µM) | 2266 | 2089 |
| LPS (10 µg/ml) | Ibuprofen (50 µM) | 2603 | 1997 |
| LPS (10 µg/ml) | Naproxen (50 µM) | 2427 | 2192 |

[#]Data are expressed as mean of duplicates.

TABLE 9

IL-6 secretion by normal human bladder smooth muscle cells after in vitro stimulation with inflammatory and non-inflammatory stimuli and treatment with analgesic

| Stimulus | Analgesic | IL-6 (pg/ml)[#] Subject 1 | IL-6 (pg/ml) Subject 2 |
|---|---|---|---|
| None | None | <5 | <5 |
| Carbachol $10^{-3}$ M | None | 232 | 278 |
| Carbachol $10^{-3}$ M | Acetaminophen (50 µM) | 119 | 135 |
| Carbachol $10^{-3}$ M | Aspirin (50 µM) | 95 | 146 |
| Carbachol $10^{-3}$ M | Ibuprofen (50 µM) | 107 | 118 |
| Carbachol $10^{-3}$ M | Naproxen (50 µM) | 114 | 127 |
| LPS (10 µg/ml) | None | 4838 | 4383 |
| LPS (10 µg/ml) | Acetaminophen (5 µM) | 2012 | 2308 |
| LPS (10 µg/ml) | Aspirin (5 µM) | 2199 | 2089 |
| LPS (10 µg/ml) | Ibuprofen (5 µM) | 2063 | 2173 |
| LPS (10 µg/ml) | Naproxen (5 µM | 2077 | 2229 |
| LPS (10 µg/ml) | Acetaminophen (50 µM) | 2018 | 1983 |
| LPS (10 µg/ml) | Aspirin (50 µM) | 1987 | 2010 |
| LPS (10 µg/ml) | Ibuprofen (50 µM) | 2021 | 1991 |
| LPS (10 µg/ml) | Naproxen (50 µM) | 2102 | 2028 |

[#]Data are expressed as mean of duplicates.

Primary normal human bladder smooth muscle cells were isolated, cultured and evaluated for their responses to analgesics in the presence of non-inflammatory (carbachol) and inflammatory (LPS) stimuli. The goal of this study was to determine whether or not normal human bladder smooth muscle cells recapitulate the observations previously made with murine bladder cells.

The above-described experiment will be repeated with analgesic agents and/or antimuscarinic agents in delayed-release, or extended-release formulation or delayed-and-extended-release formulations.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for manufacturing a pharmaceutical composition for reducing the frequency of urination, comprising:
   forming a first mixture comprising a first active ingredient formulated for immediate release and a second active ingredient formulated for extended release;
   coating the first mixture with a delayed release coating to form a core structure;
   coating the core structure with a second mixture comprising a third active ingredient formulated for immediate release and a fourth active ingredient formulated for extended release,
   wherein at least one of the first, second, third and fourth active ingredients comprises acetaminophen and at least one of the first, second, third and fourth active ingredients comprises ibuprofen, and further wherein at least one of the first, second, third and fourth active ingredients comprises an α-blocker, a 5α-reductase inhibitor or both.

2. The method of claim 1, wherein at least one of the first, second, third and fourth active ingredients comprises 5 mg to 2000 mg per agent of acetaminophen and at least one of the first, second, third and fourth active ingredients comprises 5 mg to 2000 mg per agent of ibuprofen.

3. The method of claim 1, wherein at least one of the first, second, third and fourth active ingredients comprises (1) ibuprofen, (2) acetaminophen, and (3) an α-blocker.

4. The method of claim 3, wherein the α-blocker is tamsulosin.

5. The method of claim 1, wherein at least one of the first, second, third and fourth active ingredients comprises (1) ibuprofen, (2) acetaminophen, and (3) an 5α-reductase inhibitor.

6. The method of claim 5, wherein the 5α-reductase inhibitor is finasteride.

7. The method of claim 1, wherein at least one of the first, second, third and fourth active ingredients comprises (1) ibuprofen, (2) acetaminophen, (3) an α-blocker and (4) a 5α-reductase inhibitor.

8. The method of claim 1, wherein at least one of the first, second, third and fourth active ingredients comprises an agent selected from the group consisting antimuscarinic agents, antidiuretic agents and spasmolytics.

9. The method of claim 1, wherein the delayed release coating is an enteric coating.

10. The method of claim 9, wherein the enteric coating comprises a pH-dependent polymer.

11. The method of claim 1, wherein the delayed release coating comprises a swelling layer covered by an outer semi-permeable polymer layer.

12. The method of claim 1, wherein the second active ingredient, or the fourth active ingredient or both comprise an active core comprising an extended-release coating or a polymeric matrix effective diffusion controlled release.

13. A method for manufacturing a pharmaceutical composition for reducing the frequency of urination, comprising:
    forming a core structure comprising a first active ingredient formulated for immediate release and a second active ingredient formulated for extended release;
    coating the core structure with a delayed release coating to form a coated core structure;
    mixing the coated core structure with a third active ingredient formulated for immediate release and a fourth active ingredient formulated for extended release to form a final mixture, and
    preparing a dosage form with the final mixture,
    wherein at least one of the first, second, third and fourth active ingredients comprises acetaminophen and at least one of the first, second, third and fourth active ingredients comprises ibuprofen, and at least one of the first, second, third and fourth active ingredients comprises an α-blocker, a 5α-reductase inhibitor or both.

14. The method of claim 13, wherein at least one of the first, second, third and fourth active ingredients comprises 5-2000 mg per agent of acetaminophen and at least one of the first, second, third and fourth active ingredients comprises 5 mg to 2000 mg per agent of ibuprofen.

15. The method of claim 13, wherein at least one of the first, second, third and fourth active ingredients comprises:
    (1) acetaminophen; and
    (2) ibuprofen; and
    (3) an α-blocker, a 5α-reductase inhibitor or both.

16. The method of claim 13, wherein at least one of the first, second, third and fourth active ingredients further comprises an agent selected from the group consisting antimuscarinic agents, antidiuretic agents and spasmolytics.

17. A method for manufacturing a pharmaceutical composition for reducing the frequency of urination, comprising:
    forming a core structure comprising a first active ingredient formulated for immediate release and a second active ingredient formulated for extended release;
    coating the core structure with a delayed release coating to form a coated core structure;
    coating the coated core structure with a third active ingredient formulated for immediate release to form double-coated core structure,
    wherein at least one of the first, second and third active ingredients comprises acetaminophen and at least one of the first, second and third active ingredients comprises ibuprofen and at least one of the first, second and third active ingredients comprises an α-blocker, or a 5α-reductase inhibitor.

18. The method of claim 17, wherein at least one of the first, second and third active ingredients-comprises 5-2000 mg per agent of acetaminophen and at least one of the first, second, and third active ingredients comprises 5 mg to 2000 mg per agent of ibuprofen.

19. The method of claim 17, wherein at least one of the first, second, and third active ingredients comprises:
    (1) acetaminophen; and
    (2) ibuprofen; and
    (3) an α-blocker, or a 5α-reductase inhibitor.

20. The method of claim 17, wherein at least one of the first, second, and third active ingredients further comprises an agent selected from the group consisting antimuscarinic agents, antidiuretic agents and spasmolytics.

* * * * *